United States Patent
Ravn et al.

(10) Patent No.: US 11,261,209 B2
(45) Date of Patent: Mar. 1, 2022

(54) ENHANCED COUPLING OF STEREODEFINED OXAZAPHOSPHOLIDINE PHOSPHORAMIDITE MONOMERS TO NUCLEOSIDE OR OLIGONUCLEOTIDE

(71) Applicant: Roche Innovation Center Copenhagen A/S, Horsholm (DK)

(72) Inventors: Jacob Ravn, Hørsholm (DK); Erik Daa Funder, Hørsholm (DK)

(73) Assignee: Roche Innovation Center Copenhagen A/S, Basel (CH)

( * ) Notice: Subject to any disclaimer, the term of this patent is extended or adjusted under 35 U.S.C. 154(b) by 0 days.

(21) Appl. No.: 16/300,309

(22) PCT Filed: May 9, 2017

(86) PCT No.: PCT/EP2017/060985
§ 371 (c)(1),
(2) Date: Nov. 9, 2018

(87) PCT Pub. No.: WO2017/194498
PCT Pub. Date: Nov. 16, 2017

(65) Prior Publication Data
US 2019/0153012 A1    May 23, 2019

Related U.S. Application Data

(63) Continuation of application No. PCT/EP2017/060985, filed on May 9, 2017.

(30) Foreign Application Priority Data

May 12, 2016 (EP) .................................. 16169429
Mar. 29, 2017 (EP) .................................. 17163513
Mar. 29, 2017 (EP) .................................. 17163604

(51) Int. Cl.
C07H 1/00 (2006.01)
C07H 21/00 (2006.01)
C07H 19/16 (2006.01)
C07H 19/06 (2006.01)
C07H 19/10 (2006.01)
C07H 19/20 (2006.01)

(52) U.S. Cl.
CPC ............... C07H 1/00 (2013.01); C07H 19/06 (2013.01); C07H 19/10 (2013.01); C07H 19/16 (2013.01); C07H 19/20 (2013.01); C07H 21/00 (2013.01)

(58) Field of Classification Search
CPC .......... C07H 1/00; C07H 19/06; C07H 19/20; C07H 21/00; C07H 19/10; C07H 19/16
See application file for complete search history.

(56) References Cited

U.S. PATENT DOCUMENTS

| | | | |
|---|---|---|---|
| 7,399,845 B2 * | 7/2008 | Seth ....................... | C07H 19/00 536/22.1 |
| 8,288,356 B2 * | 10/2012 | Obad .................... | C12N 15/113 514/44 A |
| 9,045,754 B2 * | 6/2015 | Bhanot ....................... | A61P 5/50 |
| 9,376,460 B2 * | 6/2016 | Chmielewski ......... | C07H 19/10 |
| 9,982,257 B2 * | 5/2018 | Butler .................. | C12Q 1/6876 |
| 10,449,210 B2 * | 10/2019 | Zhi ....................... | C07D 317/20 |

FOREIGN PATENT DOCUMENTS

| EP | 1984381 | 10/2008 |
|---|---|---|
| WO | WO 2007/090071 | 8/2007 |
| WO | WO 2007/112754 | 10/2007 |
| WO | WO 2009/043353 | 4/2009 |
| WO | WO 2009/124238 | 10/2009 |
| WO | WO 2010/036698 | 4/2010 |
| WO | WO 2014/010250 | 1/2014 |

OTHER PUBLICATIONS

Ratajczak et al., Oxidation of H-Phosphonates with Iodine By Intramolecular Support of a 2-Pyridyl Thermolabile Protecting Group, Journal of Organic Chemistry, 77(18), 7866-7872 (Aug. 12, 2012).*
Bergstrom, "Unnatural Nucleosides with Unusual Base Pairing Properties," Current protocols in Nucleic Acid Chemistry, Jun. 2009, Suppl. 37:1.4.4-1.4.32.
Hirao et al., "Natural versus artificial creation of base pairs in DNA: origin of nucleobases from the perspectives of unnatural base pair studies.," Acc Chem Res., Dec. 18, 2012, 45(12):2055-2065.
International Search Report and Written Opinion in Application No. PCT/EP2017/06985, dated Jul. 26, 2017, 11 pages.
Nukaga et al., "Stereocontrolled Solid-Phase Synthesis of Phosphorothioate Oligoribonucleoties Using 2'-0-(2-Cyanoethoxymethyl)-nucleoside 3'-0-Oxazaphospholidine Monomers," J Org Chem., 77(18):7913-7922, (Aug. 29, 2012).

(Continued)

Primary Examiner — Lawrence E Crane
(74) Attorney, Agent, or Firm — Smith Gambrell & Russell LLP

(57) ABSTRACT

The present invention relates to the synthesis of stereodefined phosphorothioate oligonucleotides of formula I:

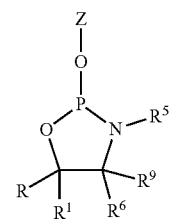

Figure 3A:
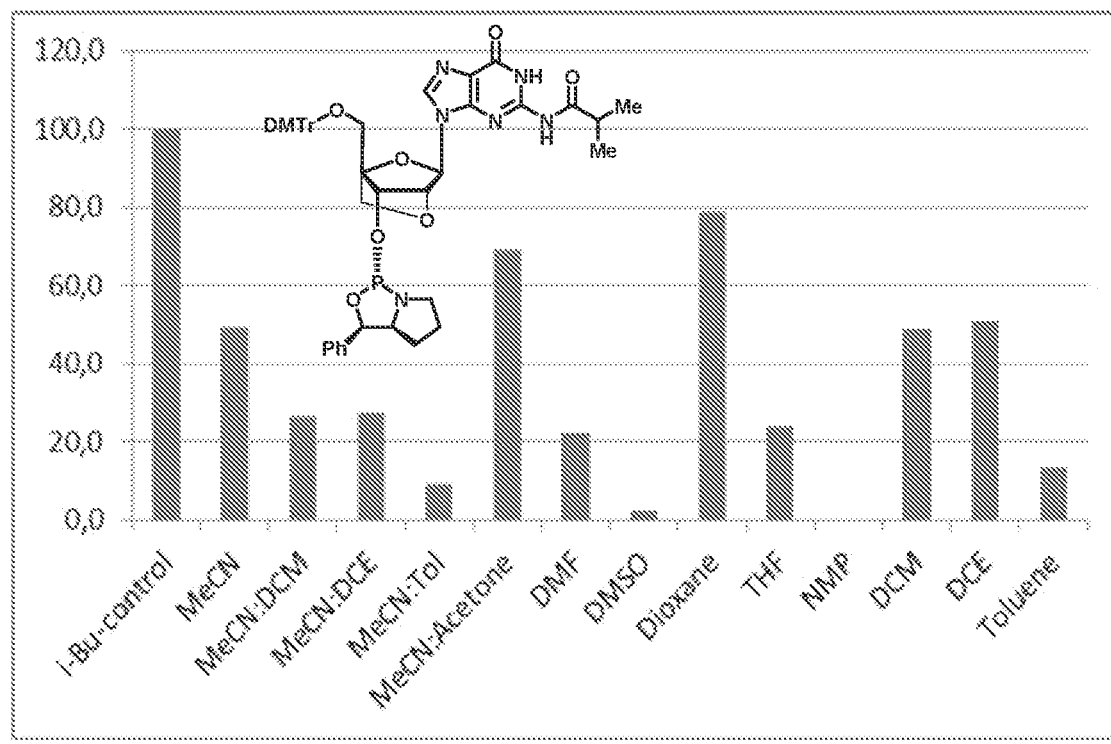

Wherein Z, $R^1$, $R^5$, $R^6$ and $R^9$ are as defined herein. Phosphorothioate oligonucleotides are useful as therapeutics.

12 Claims, 18 Drawing Sheets

Specification includes a Sequence Listing.

(56) References Cited

OTHER PUBLICATIONS

Oka et al., "Solid-phase synthesis of stereoregular oligodeoxyribonucleoside phosphorothioates using bicyclic oxazaphospholidine derivatives as monomer units," J. Am. Chem. Soc., Nov. 26, 2008, 130(47):16031-16037.
Seth et al., "Synthesis and Biophysical Evaluation of 2',4'-Constrained 2'O-Methoxyethyl and 2',4'-Constrained 2'O-Ethyl Nucleic Acid Analogues," J Org Chem., Dec. 2, 2010, 75(5):1569-1581.
Wan et al., "Synthesis, Biophysical Properties and Biological activity of Second Generation Antisense Oligonucleotides Containing Chiral Phosphorothioate Linkages," Nucleic Acids Research, Nov. 14, 2014, 42(22):13456-13468.
Wan et al., "Supplementary Information Synthesis, Biophysical Properties and Biological activity of Second Generation Antisense Oligonucleotides Containing Chiral Phosphorothioate Linkages," Nucleic Acids Research, Nov. 14, 2014, 42(22):S1-S14.

* cited by examiner

Figure 1

| Stability at 24 hours | MeCN | MeCN: DCM (1:1) | MeCN: DCE (1:1) | MeCN: Toluene (1:1) | MeCN: Acetone (1:1) | DMF | DMSO | Dioxane | THF | NMP | DCM | DCE | Toluene |
|---|---|---|---|---|---|---|---|---|---|---|---|---|---|
| D-LNA A-DMF | 2 | 3 | 3 | 3 | 2 | 3 | 3 | 2 | 1 | 3 | 1 | 1 | 3 |
| L-LNA A-DMF | 3 | 3 | 3 | 3 | 2 | 3 | 3 | 1 | 1 | 3 | 1 | 1 | 3 |
| D-LNA T-DMF | 1 | 1 | 1 | 3 | 2 | 2 | 3 | 1 | 1 | 3 | 1 | 1 | 3 |
| L-LNA T-DMF | 1 | 1 | 3 | 3 | 2 | 3 | 2 | 1 | 2 | 2 | 1 | 1 | 3 |
| D-LNA C-DMF | 3 | 3 | 3 | 3 | 3 | 3 | 3 | 1 | 1 | 3 | 2 | 2 | 3 |
| L-LNA C-DMF | 2 | 2 | 2 | 3 | 2 | 3 | 3 | 1 | 2 | 3 | 1 | 1 | 3 |
| D-LNA G-DMF | 1 | 1 | 1 | 3 | 2 | 1 | 1 | 1 | 1 | 3 | 1 | 1 | 3 |
| L-LNA G-DMF | Not soluble | 3 | Not soluble | Not soluble | Not soluble | 3 | 3 | Not soluble | Not soluble | 3 | 3 | 3 | Not soluble |
| L-LNA G-iBu | 2 | 2 | 2 | 3 | 2 | 3 | 3 | 1 | 2 | n/a | 2 | 2 | 3 |
| D-DNA A-DMF | 3 | 3 | 3 | 3 | 3 | 3 | 3 | 2 | 1 | 3 | 2 | 2 | 3 |
| L-DNA A-DMF | 3 | 3 | 3 | 3 | 3 | 3 | 3 | 1 | 2 | 3 | 2 | 2 | 3 |
| D-DNA T-DMF | 3 | 3 | 3 | 3 | 3 | 3 | 3 | 1 | 1 | 3 | 1 | 1 | 3 |
| L-DNA T-DMF | 3 | 1 | 1 | 1 | 1 | 1 | 1 | 1 | 1 | 3 | 1 | 1 | 3 |
| D-DNA C-DMF | 3 | 2 | 2 | 3 | 2 | 3 | 3 | 1 | 1 | 3 | 1 | 1 | 3 |
| L-DNA C-DMF | 2 | 2 | 2 | 3 | 2 | 3 | 3 | 2 | 1 | 3 | 1 | 1 | 3 |
| D-DNA G-DMF | 3 | 3 | 3 | 3 | 3 | 3 | 3 | 1 | 1 | n/a | n/a | n/a | 3 |
| L-DNA G-DMF | 2 | 3 | 3 | 3 | 3 | 3 | 3 | 3 | 3 | n/a | n/a | n/a | 3 |

Figure 2

Solubility 0 h

| | MeCN | MeCN:DCM (1:1) | MeCN:DCE (1:1) | MeCN:Tol. (1:1) | MeCN:Acetone (1:1) | DMF | DMSO | Dioxane | THF | NMP | DCM | DCE | Toluene |
|---|---|---|---|---|---|---|---|---|---|---|---|---|---|
| D-LNA G-DMF | yes | yes | yes | yes | yes | yes | yes | yes | yes | yes | yes | yes | yes |
| L-LNA G-DMF | no | yes | no | no | no | yes | yes | no | no | yes | yes | no | no |
| L-LNA G-i-Bu | yes | yes | yes | yes | yes | yes | yes | yes | yes | n/a | yes | yes | yes |

Solubility 24 h

| | MeCN | MeCN:DCM (1:1) | MeCN:DCE (1:1) | MeCN:Tol. (1:1) | MeCN:Acetone (1:1) | DMF | DMSO | Dioxane | THF | NMP | DCM | DCE | Toluene |
|---|---|---|---|---|---|---|---|---|---|---|---|---|---|
| D-LNA G-DMF | yes | yes | yes | yes | yes | yes | yes | yes | yes | yes | yes | yes | yes |
| L-LNA G-DMF | no | yes | yes | no | no | yes | yes | no | no | yes | yes | yes | no |
| L-LNA G-i-Bu | no | no | no | no | yes | yes | no | yes | yes | n/a | yes | yes | yes |

Figure 8

Figure 17
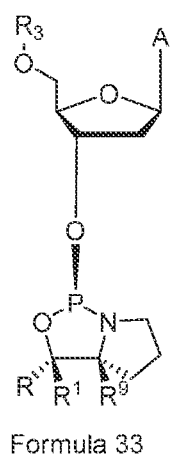
Formula 33
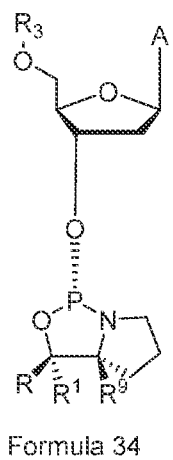
Formula 34
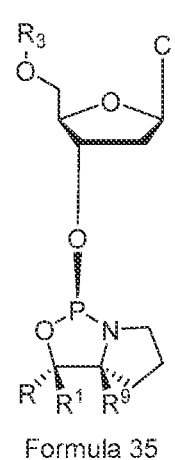
Formula 35
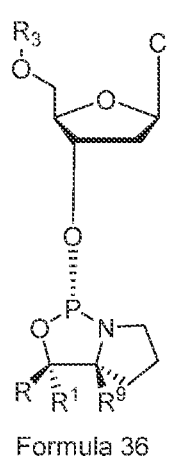
Formula 36
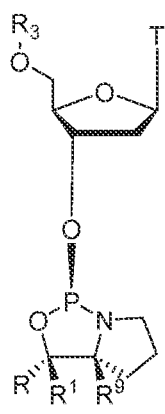
Formula 37
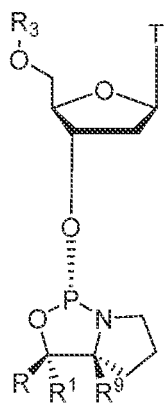
Formula 38
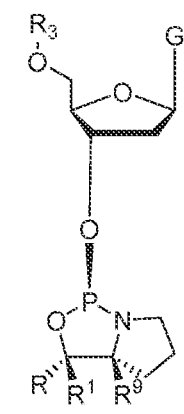
Formula 39
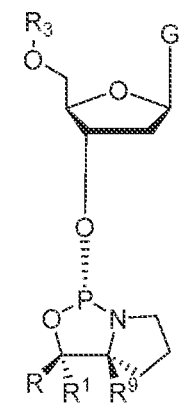
Formula 40

Figure 18
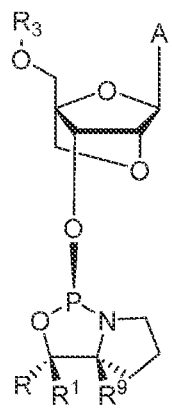
Formula 41
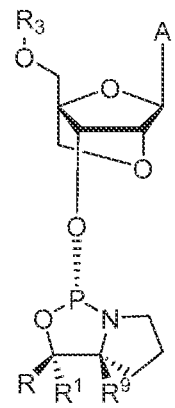
Formula 42
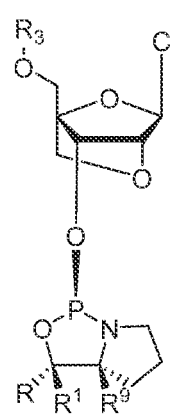
Formula 43
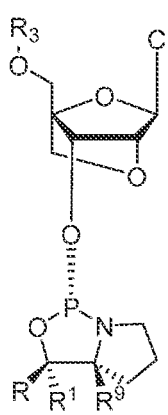
Formula 44
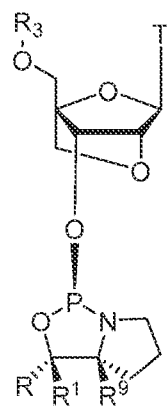
Formula 45
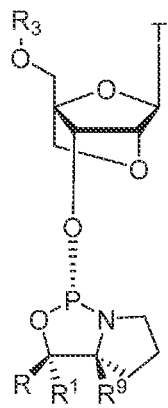
Formula 46
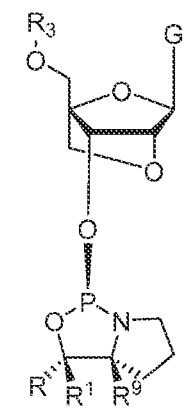
Formula 47
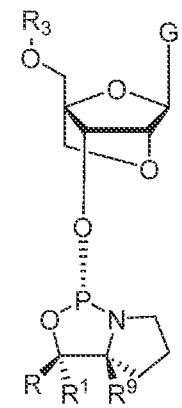
Formula 48

ENHANCED COUPLING OF STEREODEFINED OXAZAPHOSPHOLIDINE PHOSPHORAMIDITE MONOMERS TO NUCLEOSIDE OR OLIGONUCLEOTIDE

CLAIM OF PRIORITY

This application is a national phase application under 35 U.S.C. § 371 of PCT International Application No. PCT/EP2017/060985 filed May 9, 2017, which claims priority to EP Patent Application No. 17163513.9 filed Mar. 29, 2017, EP Patent Application No. 17163604.6 filed Mar. 29, 2017 and EP Patent Application No. 16169429.4 filed May 12, 2016. The entire contents of the foregoing applications are hereby incorporated by reference.

FIELD OF THE INVENTION

The present invention relates to the field of stereodefined phosphorothioate oligonucleotides and to stereodefining nucleoside monomers and methods of synthesis of stereodefined oligonucleotides using said monomer. Herein are disclosed solvent compositions which provide enhanced solubility and stability of stereodefining nucleoside monomers, and can be used to improve the coupling efficacy of such monomers in oligonucleotide synthesis.

BACKGROUND TO THE INVENTION

Recently it has become apparent that the use of stereodefined phosphorothioate internucleoside linkages in oligonucleotides allow for the optimisation of the pharmacological profile of therapeutic oligonucleotides. However, the manufacture of stereodefined phosphorothioate oligonucleotides is at present comparatively inefficient as compared to non stereodefined phosphorothioate oligonucleotides. There is therefore a need to improve the efficiency of synthesis of stereodefined oligonucleotides.

Wan et al., Nucleic Acids Research (Advance Access published Nov. 14, 2014) discloses the synthesis of (S)cET gapmer antisense oligonucleotides containing chiral phosphorothioate linkages within the DNA gap region. The oligonucleotides made by Wan et al. incorporated oxazaphospholidine DNA monomers into (S)cET gapmers. The DNA amidites were prepared as 0.2M concentration in acetonitrile/toluene (1:1 v/v), and were coupled using a double coupling step. The (S)cET monomers were standard (not stereodefining) amidites.

WO2014/010250 discloses nucleoside monomers which when incorporated into an oligonucleotide provide a chirally defined stereocenter at the corresponding phosphorothioate internucleoside linkage position. The coupling step reported in WO WO2014/010250 is performed in acetonitrile.

In some embodiments, the invention is based upon the observation that oxazaphospholidine phosphoramidite monomers can be difficult to solubilize in many solvents, and even when solubilized can be so unstable as to limit the ability to make stereodefined oligonucleotides to a commercially relevant scale.

In addition to being able to provide a suitable stable solution of oxazaphospholidine phosphoramidite monomers, the invention is also based upon the finding that oxazaphospholidine phosphoramidite monomer solutions can result in a relatively inefficient coupling during oligonucleotide synthesis.

By use of an aromatic heterocylic solvent in acetonitrile, the present inventors have found that the solubility, stability and/or reactivity of oxazaphospholidine phosphoramidite monomers may be improved.

STATEMENT OF INVENTION

The invention provides for method for coupling an oxazaphospholidine phosphoramidite monomer to a 5'-terminus of a nucleoside or oligonucleotide, comprising the step of reacting the nucleoside or oligonucleotide, with an oxazaphospholidine phosphoramidite monomer, wherein said reaction takes place in an acetonitrile solvent composition comprising acetonitrile and an aromatic heterocyclic solvent. The method for coupling of the invention, may be incorporated into a method for oligonucleotide synthesis.

The invention provides for a method for the synthesis of a stereodefined phosphorothioate oligonucleotide, comprising the step of:
  a) deprotect a protected 5'-hydroxy terminus of a nucleoside, or oligonucleotide, attached to a solid support,
  b) coupling an oxazaphospholidine phosphoramidite monomer to the deprotected 5'-hydroxy terminus of a nucleoside or oligonucleotide, wherein said coupling reaction takes place in an acetonitrile solvent composition comprising acetonitrile and an aromatic heterocyclic solvent, to form a phosphite triester intermediate and
  c) oxidizing the phosphite triester intermediate with a sulfurizing reagent.
  d) optionally repeating steps a)-c) for one or more further elongation cycles,
  e) deprotection and cleavage of the oligonucleotide from the solid support.

The method of the invention may comprise multiple further elongation cycles d), such as 2, 3, 4, 5, 6, 7, 8, 9, 10, 11, 12, 13, 14, 15, 16, 17, 18, 19, 20 or more further elongation cycles.

The invention provides for a method for coupling an oxazaphospholidine phosphoramidite monomer to a 5'-terminus of a nucleoside or oligonucleotide, or a hydroxyl group attached to a solid support (e.g. unilinker), comprising the step of reacting the nucleoside, the oligonucleotide or solid support, with the oxazaphospholidine phosphoramidite monomer, wherein said reaction takes place in an acetonitrile solvent composition comprising acetonitrile and an aromatic heterocyclic solvent.

The invention provides for a method for coupling an oxazaphospholidine phosphoramidite monomer to a 5'-terminus of a nucleoside or oligonucleotide, or a hydroxyl group attached to a solid support (e.g. unilinker), comprising the step of reacting the nucleoside, the oligonucleotide or solid support, with the oxazaphospholidine phosphoramidite monomer, wherein said reaction takes place in an acetonitrile solvent composition comprising acetonitrile and an aromatic heterocyclic solvent, and an activator.

The invention provides for a method for oligonucleotide synthesis comprising the method for coupling an oxazaphospholidine phosphoramidite monomer to a 5'-terminus of a nucleoside or oligonucleotide of the invention.

The invention provides for an acetonitrile solution composition comprising an oxazaphospholidine phosphoramidite monomer, acetonitrile and an aromatic heterocyclic solvent.

The invention provides for a method for dissolving oxazaphospholidine phosphoramidite monomer said method comprising adding the monomer to a solvent composition comprising acetonitrile and an aromatic heterocyclic solvent, and optionally an activator.

The invention provides for the use of an aromatic heterocyclic solvent to enhance the stability and/or solubility of a oxazaphospholidine phosphoramidite in acetonitrile.

The invention provides for the use of an aromatic heterocyclic solvent to enhance the reactivity, e.g. the reactivity in an oligonucleotide synthesis coupling step, of an oxazaphospholidine phosphoramidite in acetonitrile.

As is illustrated in the examples, the use of solvent composition of the invention (also referred to as the acetonitrile and aromatic heterocyclic solvent composition), enhances the solubility and stability of oxazaphospholidine phosphoramidite monomers and this may result in an enhanced utility in oligonucleotide synthesis. In some embodiments the oxazaphospholidine phosphoramidite monomers are soluble in the solvent composition for a period of at least 24 hours. The invention further provides for a solution of an oxazaphospholidine phosphoramidite monomer comprising the monomer and an acetonitrile solvent composition of the invention (acetonitrile and an aromatic heterocyclic solvent composition). In some embodiments, the solution of oxazaphospholidine phosphoramidite monomer is stable for at least 24 hours.

FIGURES

FIG. 1: Stability of various L and D nucleoside monomers in a selection of solvents. 3=Comparatively unstable, 2=intermediate stability, 1=Comparatively stable.

FIG. 2: Solubility of various L and D nucleoside monomers in a selection of solvents FIG. 3: Stability of L-LNA-G-iBu monomer (3a) and L-LNA-G-DMF monomer as measured after 24 hours in various solvents (see example 6).

Figure 4:
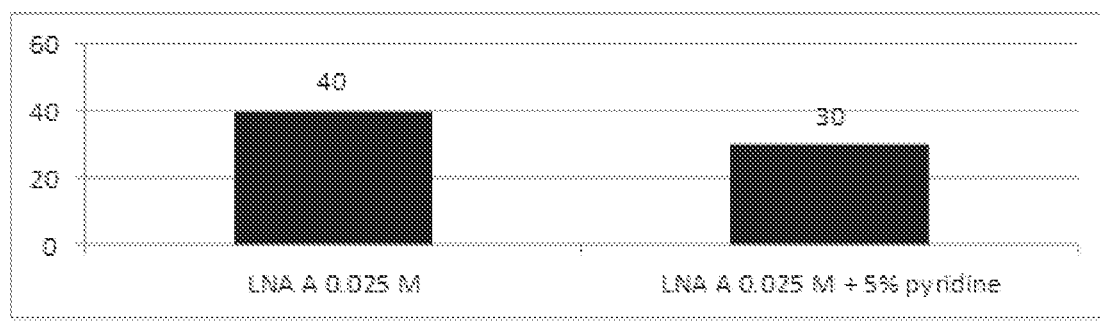

FIG. 4: Addition of 5% pyridine to the acetonitrile solvent decreases the coupling efficacy of conventional phosphoramidites.

Figure 5:
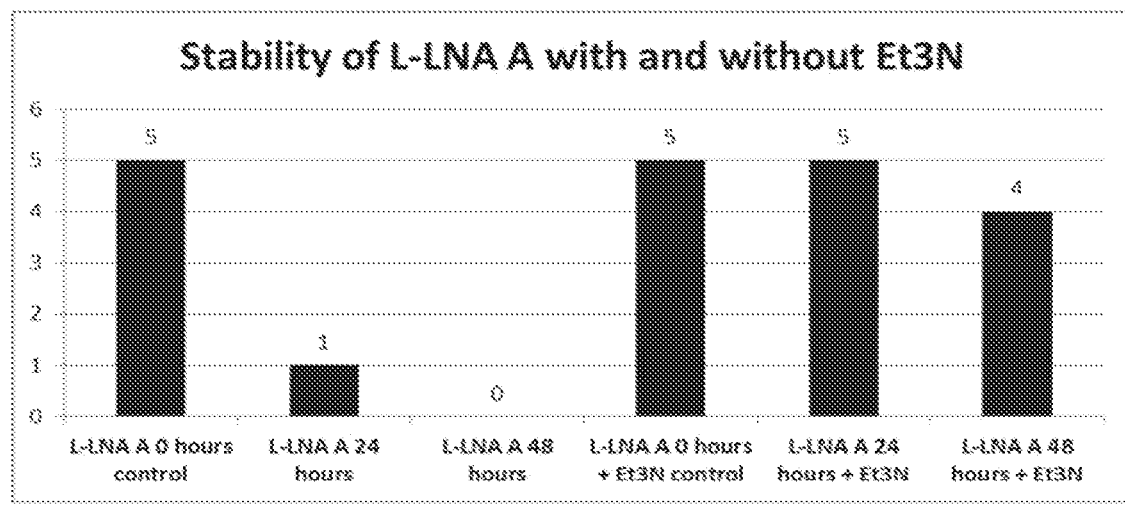

FIG. 5: Stability of L-LNA-A with and without triethylamine. Triethylamine stabilises L-LNA A monomers.

Figure 6:
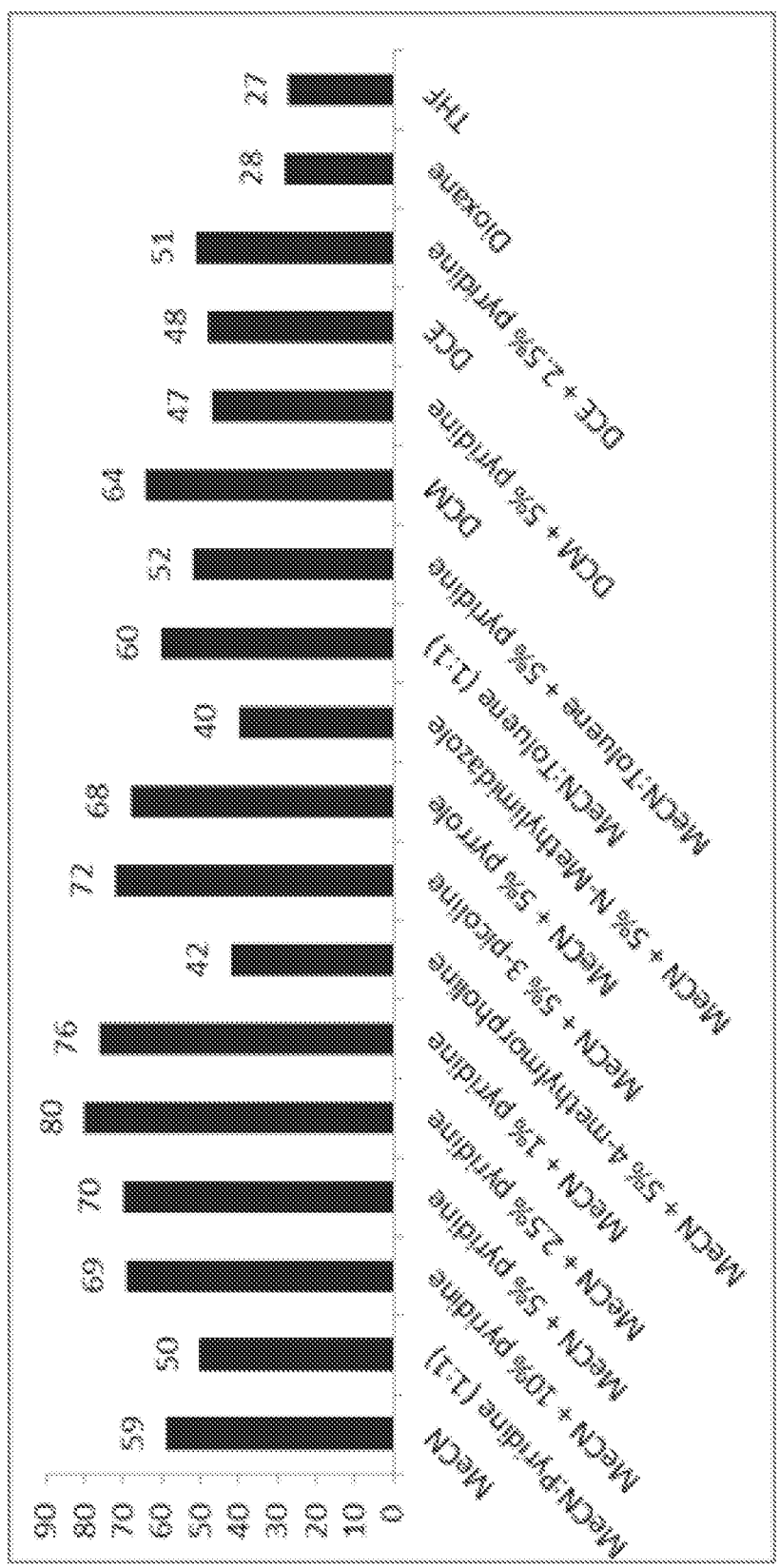

FIG. 6: Relative coupling efficiency in the model system using stereodefined L-LNA-A oxazaphospholidine phosphoramidite monomers and a variety of different amine bases.

Figure 7:
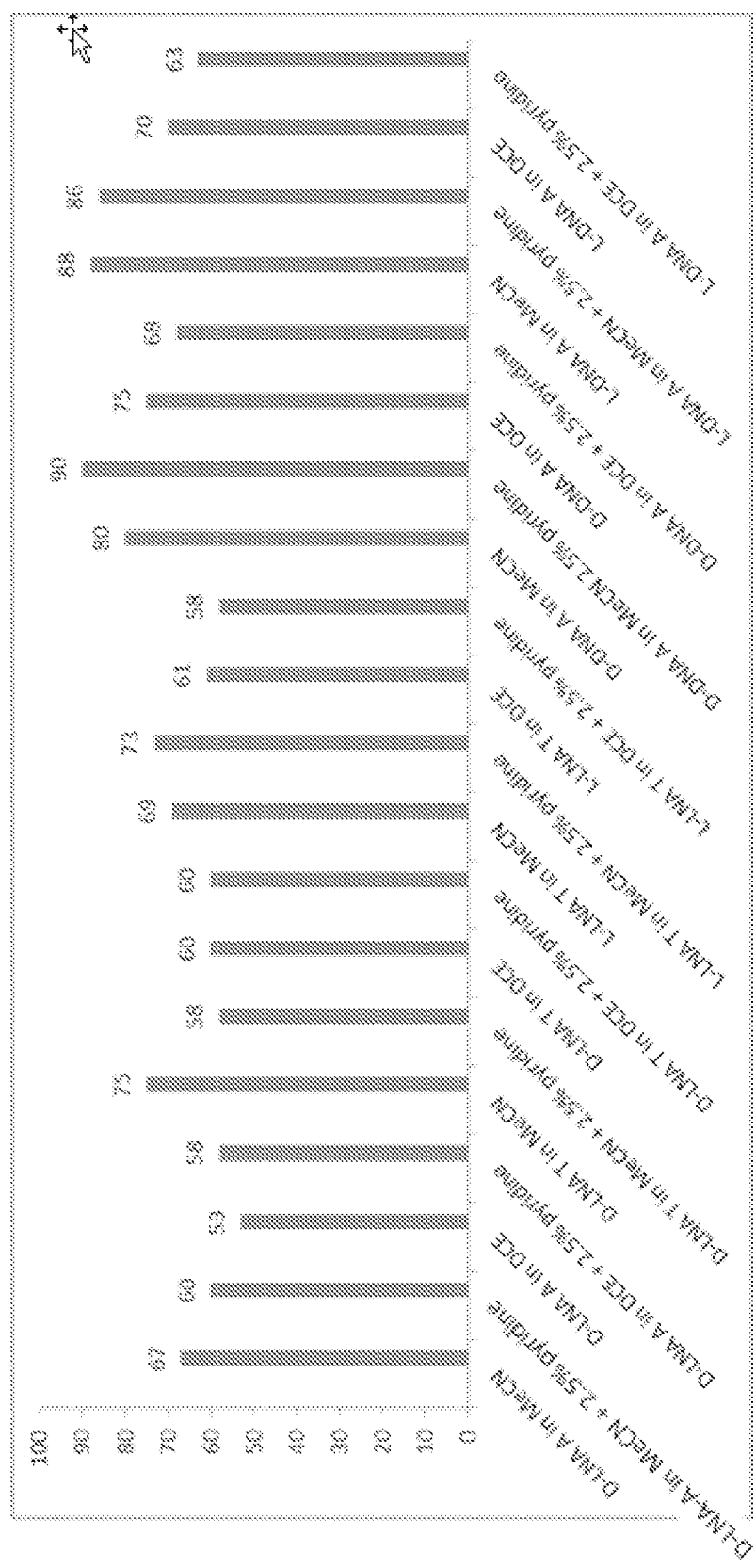

FIG. 7: Relative coupling efficiency in the model system using various oxazaphospholidine phosphoramidite monomers in a variety of solvents. Further testing additional monomers reveals that the solubility enhancing effect of the addition of pyridine is general across the series of monomers. As in the case of D-LNA A, D-DNA A and, L-DNA A these monomers are not soluble after 24 hours in MeCN. However with the addition of pyridine the solubility of the monomer is preserved. The enhancement in reactivity is also seen for D-DNA A and L-LNA T while L-DNA A and D-LNA A reacts in a comparable manner.

Figure 8:
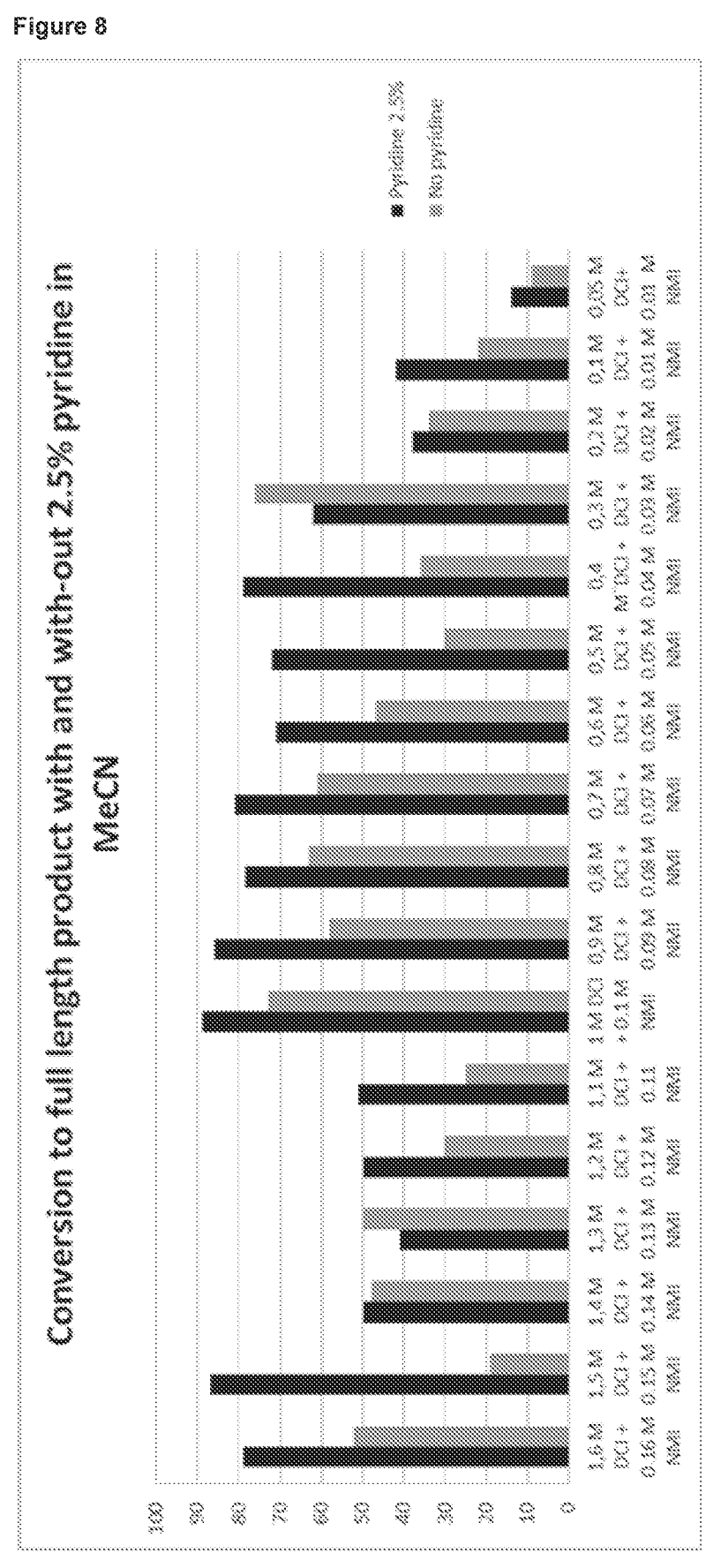

FIG. 8: Conversion of full length product with and without 2.5% pyridine.

Figure 9:
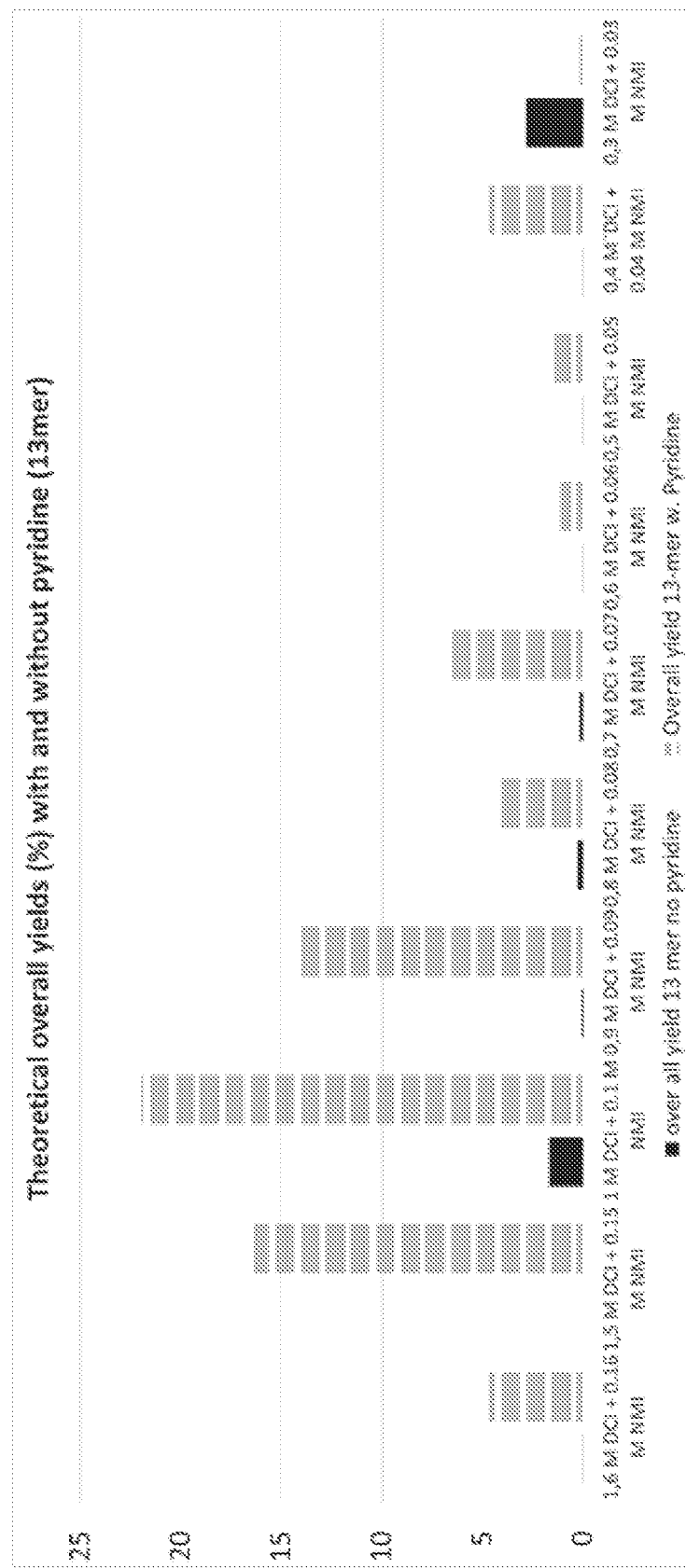

FIG. 9: Theoretical yields (%) with and without pyridine—a 13mer.

Figure 10:
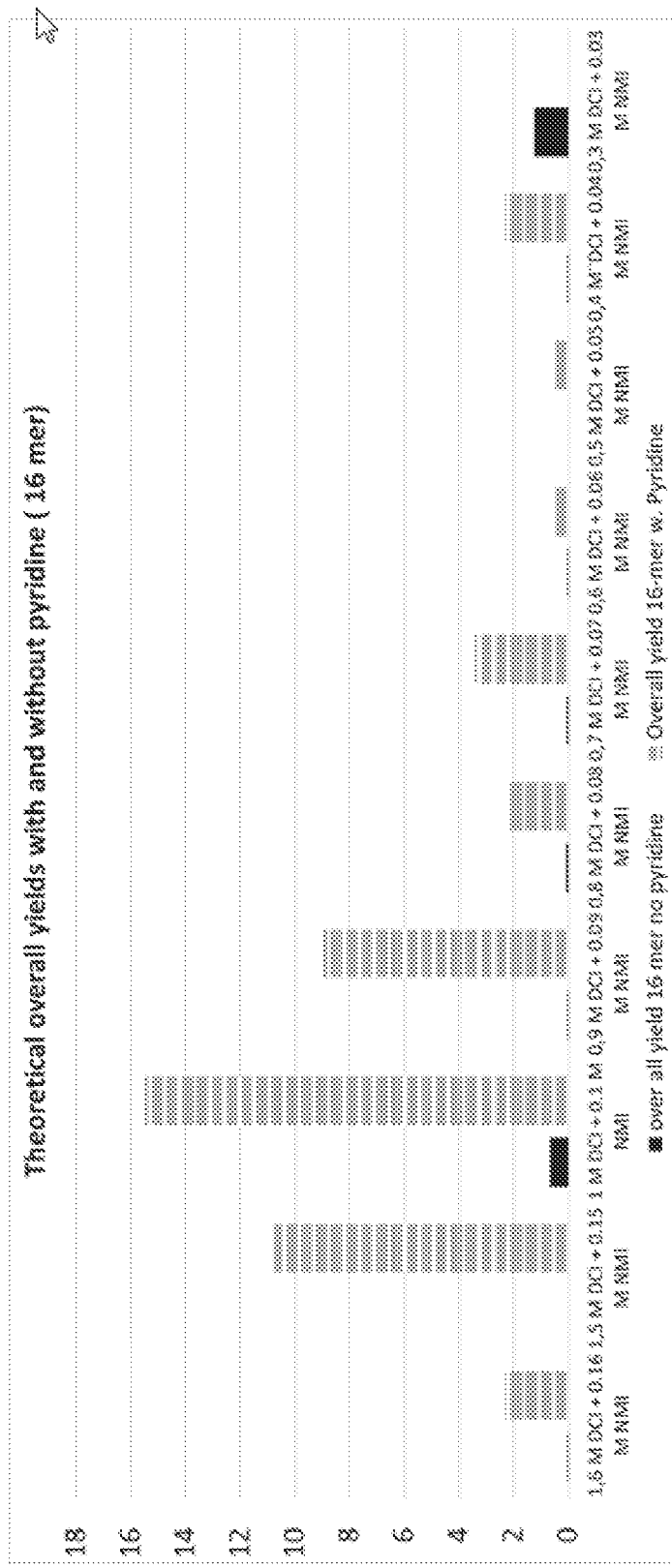

FIG. 10: Theoretical yields (%) with and without pyridine—a 16mer.

Figure 11:
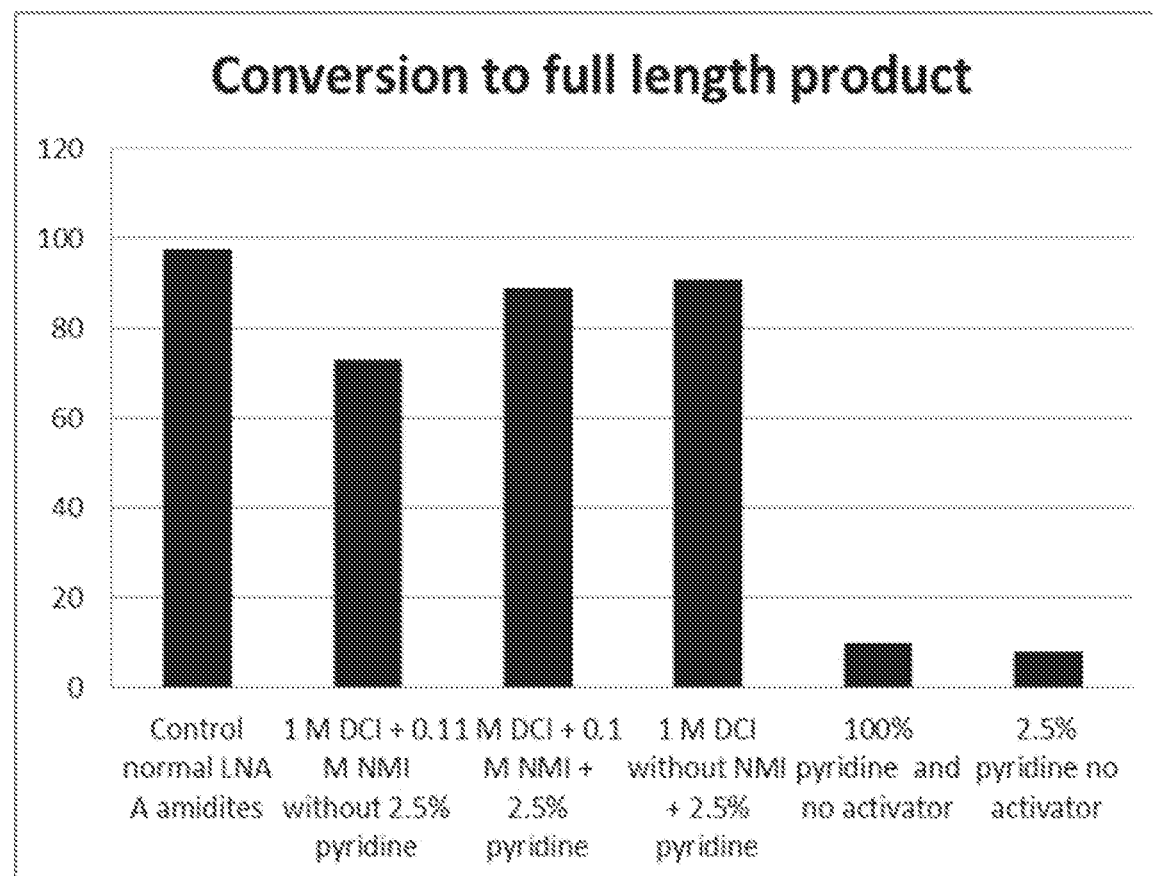

FIG. 11: Conversion to full length product in the presence of no pyridine, 100% pyridine solvent, and 2.5% pyridine, illustrating that 2.5% pyridine results in a conversion rate which is approaching that achieved with non-stereodefined phosphoamidite coupling.

Figure 12:
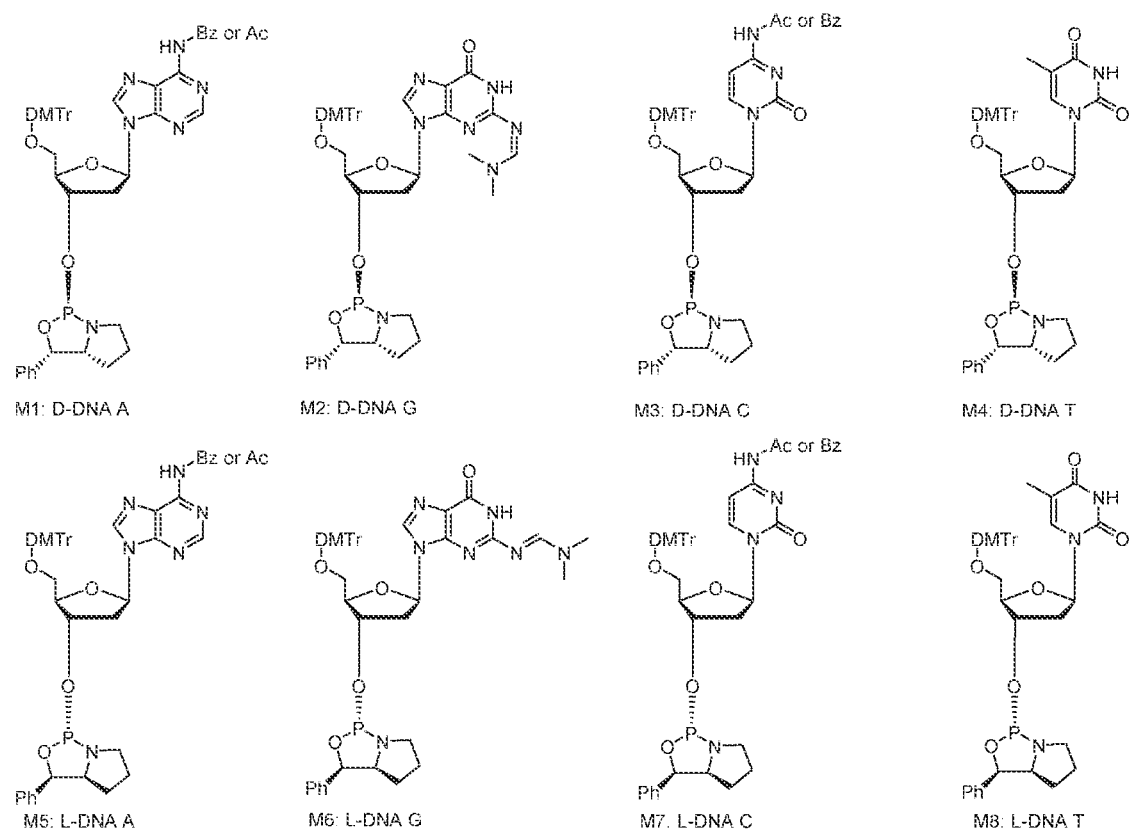

FIG. 12: Exemplary oxazaphospholidine phosphoramidite DNA monomers M1-M8. Ac=acetyl protection group, Bz=benzoyl protection group.

Figure 13:
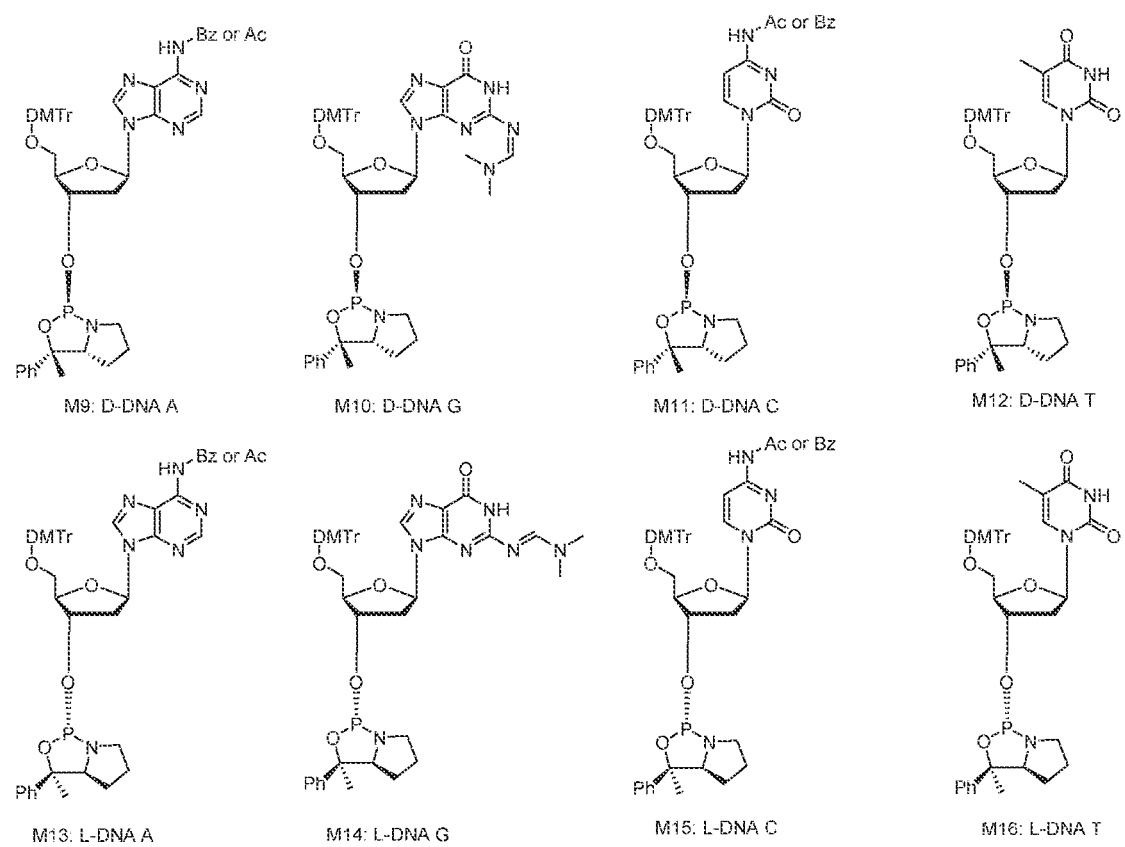

FIG. 13: Exemplary oxazaphospholidine phosphoramidite DNA monomers M9-M16, wherein $R^1$=methyl; Ac=acetyl protection group, Bz=benzoyl protection group.

Figure 14:
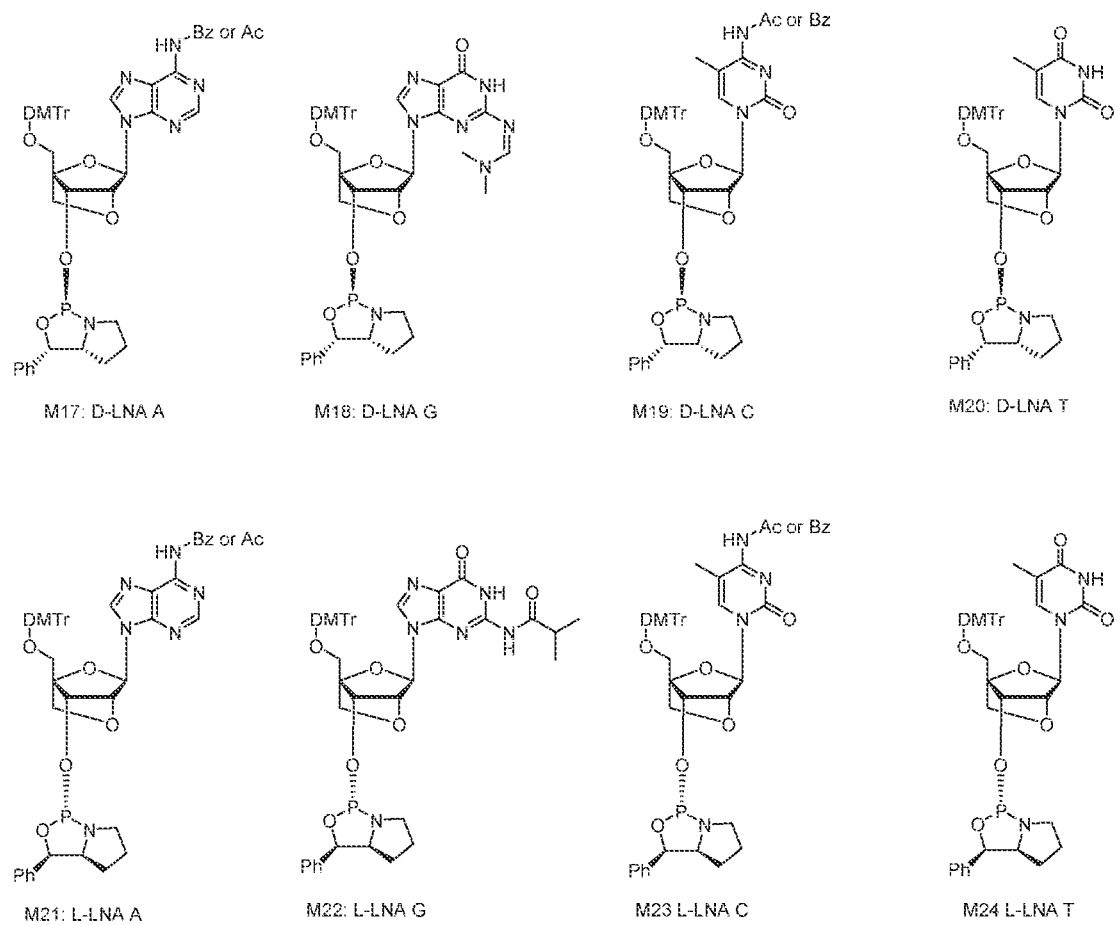

FIG. 14: Exemplary oxazaphospholidine phosphoramidite LNA monomers M17-M24. Ac=acetyl protection group, Bz=benzoyl protection group.

Figure 15:
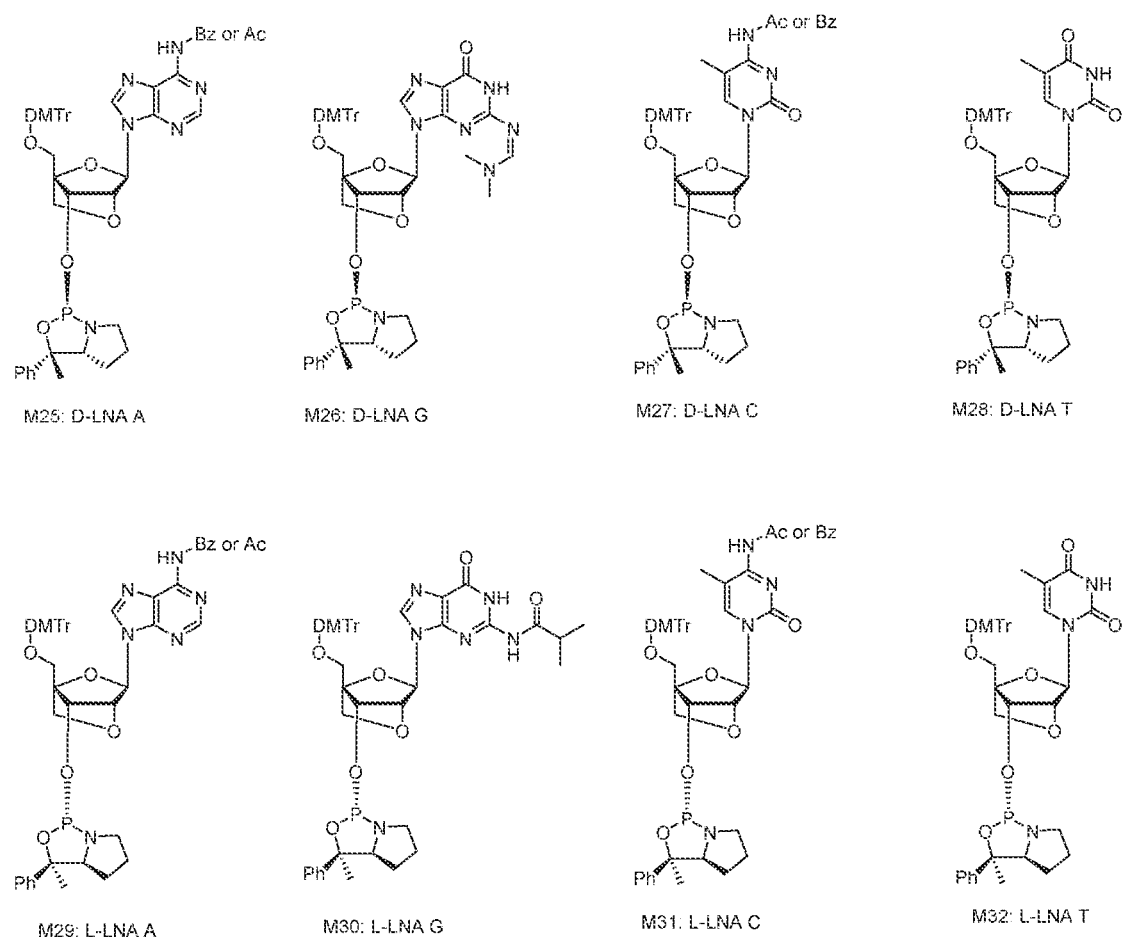

FIG. 15: Exemplary oxazaphospholidine phosphoramidite LNA monomers M25-M32; wherein $R^1$=methyl; Ac=acetyl protection group, Bz=benzoyl protection group.

Figure 16:
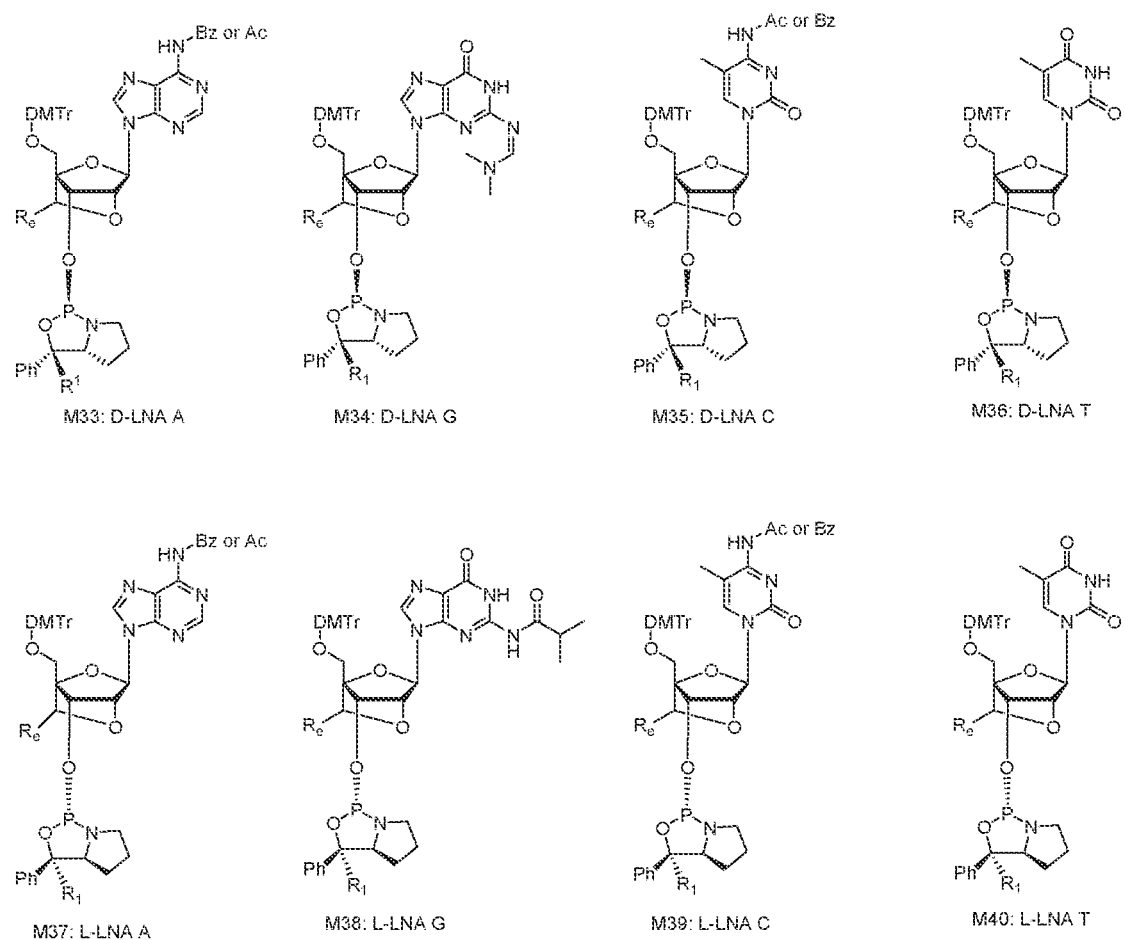

FIG. 16: Exemplary oxazaphospholidine phosphoramidite LNA monomers M32-M40, wherein $R^1$=is selected from hydrogen and methyl; $R_e$ is methyl which may be in either the S or R configuration, preferably in the S configuration ((S)Cet), Ac=acetyl protection group, Bz=benzoyl protection group.

FIG. 17: Exemplary oxazaphospholidine phosphoramidite DNA monomers (Formulas 33-40). A=adenine, which may optionally be protected, e.g. with acetyl or benzoyl; T=thymine; C=cytosine which may optionally be 5-methyl cytosine, cytosine or 5-methyl cytosine may optionally be protected e.g. with benzoyl or acetyl; G=guanine which may optionally protected e.g. with acyl, such as iBu or DMF; $R^3$=is selected from the group consisting of $CH_2ODMTr$, $CH_2$-Alkyl-O-DMTr, CH-Me-O-DMTr, $CH_2OMMTr$, $CH_2$-Alkyl-O-MMTr, CH(Me)-O-MMTr, CH—$R^a$—O-DMTrR$^b$, and CH—$R^a$—O-MMTrR$^b$, preferably —$CH_2$—O-DMTr; R is aryl, preferably phenyl; $R^1$ is hydrogen or methyl; $R^9$ is hydrogen.

FIG. 18: Exemplary oxazaphospholidine phosphoramidite LNA monomers (Formulas 41-48). A=adenine, which may optionally be protected, e.g. with acetyl or benzoyl; T=thymine; C=cytosine which may optionally be 5-methyl cytosine, cytosine or 5-methyl cytosine may optionally be protected e.g. with benzoyl or acetyl; G=guanine which may optionally protected e.g. with acyl, such as iBu for L-LNA-G monomers or either acyl (such as iBu) or DMF for D-LNA-G monomer; $R^3$=is selected from the group consisting of $CH_2ODMTr$, $CH_2$-Alkyl-O-DMTr, CH-Me-O-DMTr, $CH_2OMMTr$, $CH_2$-Alkyl-O-MMTr, CH(Me)-O-MMTr, CH—$R^a$—O-DMTrR$^b$, and CH—$R^a$—O-MMTrR$^b$, preferably —$CH_2$—O-DMTr; R is aryl, preferably phenyl; $R^1$ is hydrogen or methyl; $R^9$ is hydrogen.

Figure 19:
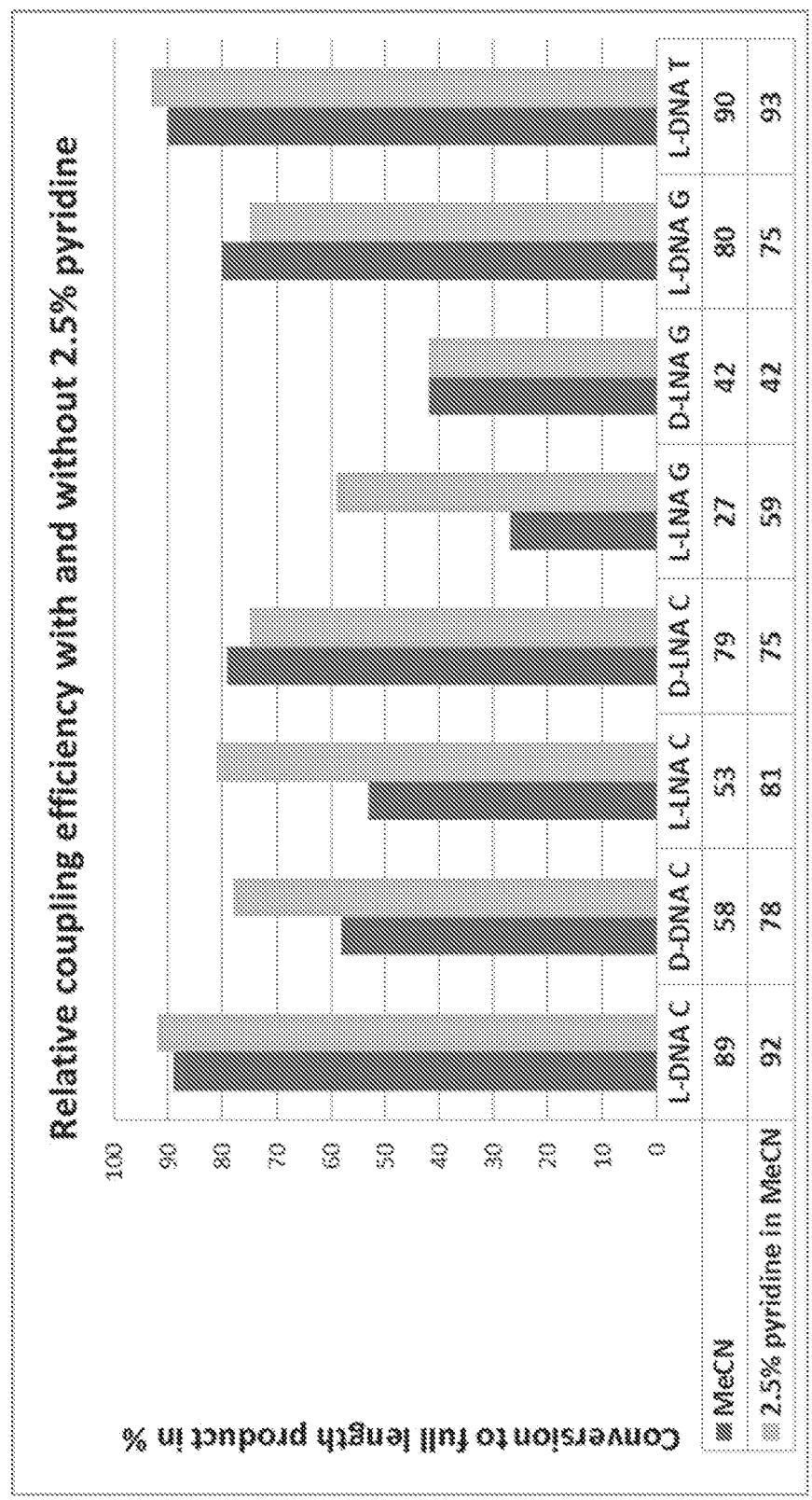

FIG. 19: Relative coupling efficiency in the model system using various oxazaphospholidine phosphoramidite monomers in acetonitrile with or without 2.5% pyridine. The figure illustrates that the coupling efficacy of L-LNA-G, L-LNA-C, D-DNA-C are markedly improved by the presence of 2.5% pyridine in the coupling solvent, for the remaining monomers tested, the addition of pyridine either improve coupling efficacy (e.g. L-DNA-T or L-DNA-C) did not adversely effects the coupling efficacy, and considering the solubility and stability benefits of pyridine on the monomers, the results illustrate the benefit of using coupling solvents comprising heterocyclic base solvents, such as pyridine, are seen for all the monomers.

DETAILED DESCRIPTION

As used herein, the term "aryl" refers to an aromatic ring wherein each of the atoms forming the ring is a carbon atom. Aryl rings are formed by five, six, seven, eight, nine, or more than nine carbon atoms. Aryl groups are a substituted or unsubstituted. In one aspect, an aryl is a phenyl or a naphthalenyl. Depending on the structure, an aryl group can be a monoradical or a diradical (i.e., an arylene group). In one aspect, an aryl is a $C_{6-10}$ aryl. In some embodiments aryl is phenyl. When substituted aryl may be substituted with a group selected from the group consisting of: $C_{1-4}$ alkyl group, $C_{6-14}$ aryl group $C_{1-4}$, alkoxy group, $C_{7-14}$ aralkyl group, $C_{1-4}$ alkyl, $C_{6-14}$ aryl group, $C_{1-4}$ alkoxy, $C_{6-14}$ aryl group, or $C_{6-14}$ aryl $C_{1-4}$ alkyl group. Multiple substitutions may be dependently or independently selected from the group consisting of: $C_{1-4}$ alkyl group, $C_{6-14}$ aryl group $C_{1-4}$, alkoxy group, $C_{7-14}$ aralkyl group, $C_{1-4}$ alkyl, $C_{6-14}$ aryl group, $C_{1-4}$ alkoxy, $C_{6-14}$ aryl group, or $C_{6-14}$ aryl $C_{1-4}$ alkyl group; or a group selected from the group consisting of halide, such as iodide, fluoride, bromide or chloride, such as phenyl substituted with halide, such as iodide, fluoride, bromide or chloride.

An "alkyl" group refers to an aliphatic hydrocarbon group. The alkyl moiety may be a saturated alkyl group (which means that it does not contain any units of unsaturation, e.g. carbon-carbon double bonds or carbon-carbon triple bonds) or the alkyl moiety may be an unsaturated alkyl group (which means that it contains at least one unit of unsaturation). The alkyl moiety, whether saturated or unsaturated, may be branched, straight chain, or include a cyclic portion. The point of attachment of an alkyl is at a carbon atom that is not part of a ring. The "alkyl" moiety may have 1 to 10 carbon atoms (whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms, although the present definition also covers the occurrence of the term "alkyl" where no numerical range is designated). Alkyl includes both branched and straight chain alkyl groups. The alkyl group of the compounds described herein may be designated as "$C_{1-6}$ alkyl" or similar designations. By way of example only, "$C_{1-6}$ alkyl" indicates that there are one, two, three, four, five, or six carbon atoms in the alkyl chain, i.e., the alkyl chain is selected from the group consisting of methyl, ethyl, propyl, iso-propyl, n-butyl, isobutyl, sec-butyl, and tert-butyl. Typical alkyl groups include, but are in no way limited to, methyl, ethyl, propyl, isopropyl, butyl, isobutyl, tertiary butyl, pentyl, hexyl, allyl, cyclopropylmethyl, cyclobutylmethyl, cyclopentylmethyl, cyclohexylmethyl, and the like. In one aspect, an alkyl is a $C_{1-6}$ or $C_{1-4}$ alkyl or $C_{1-3}$ alkyl. $C_{1-3}$ alkyl group means straight or branched alkyl group that has 1 to 3 carbon atoms. Examples of $C_{1-4}$ alkyl group are methyl, ethyl, propyl and isopropyl. $C_{1-3}$ alkyl group means straight or branched alkyl group that has 1 to 4 carbon atoms. Examples of $C_{1-3}$ alkyl groups are methyl, ethyl, propyl, isopropyl, butyl, isobutyl, and tert-butyl.

"Alkenyl" groups are straight chain, branch chain, and cyclic hydrocarbon groups containing at least one carbon-carbon double bond. Alkenyl groups can be substituted.

"Alkynyl" groups are straight chain, branch chain, and cyclic hydrocarbon groups containing at least one carbon-carbon triple bond. Alkynyl groups can be substituted.

An "alkoxy" group refers to an alklyl group linked to oxygen i.e. (alkyl)-O— group, where alkyl is as defined herein. Examples include methoxy (—OOH$_3$) or ethoxy (—OCH$_2$CH$_3$) groups.

An "alkenyloxy" group refers to an alkenyl group linked to oxygen i.e. (alkenyl)-O— group, where alkenyl is as defined herein.

An "alkynyloxy" group refers to an alkynyl group linked to oxygen i.e. (alkynyl)-O— group, where alkynyl is as defined herein.

An "aryloxy" group refers to an aryl group linked to oxygen i.e. (aryl)-O— group, where the aryl is as defined herein. An example includes phenoxy (—OC$_6$H$_5$) group.

"Silyl" refers to H$_3$Si—. "Substituted silyl" as used herein, refers to a moiety which has one or more the the hydrogen of silyl substituted. Examples include, but are not limited to, TBDMS (tert-butyldimethylsilyl), TBDPS (tert-butyldiphenylsilyl) or TMS (trimethylsilyl) group.

The term "halogen" is intended to include fluorine, chlorine, bromine and iodine. The term "halide" includes fluoride, bromide, iodide and chloride.

An "acyl protection group" comprises an acyl group —C(=O)—R$^7$, wherein R$^7$ is a terminal group, for example a group selected from, alkyl-, alkyl-, alkenyl-, alkynyl-, cycloalkyl- and aryl-group; or a group selected from, unsubstituted alkyl-, unsubstituted alkenyl-, unsubstituted alkynyl-, unsubstituted cycloalkyl- or unsubstituted aryl-group; or a group selected from substituted alkyl-, substituted alkenyl-, substituted alkynyl-, substituted cycloalkyl- or substituted aryl-group. In some embodiments R$^7$ may be selected from the group consisting of unsubstituted $C_{1-6}$-alkyl-, unsubstituted $C_{2-6}$-alkenyl-, unsubstituted $C_{2-6}$-alkinyl-, unsubstituted $C_{3-7}$-cycloalkyl- or unsubstituted phenyl-group or substituted $C_{1-6}$-alkyl-, substituted $C_{2-6}$-alkenyl-, substituted $C_{2-6}$-alkinyl-, substituted $C_{3-7}$-cycloalkyl- or substituted phenyl-group; wherein when substituted, the substituent group may be mono or poly substituted, e.g. with one or more substituents selected from the group consisting of halogen, $C_{1-6}$-alkyl, $C_{2-6}$-alkenyl, $C_{2-6}$-alkynyl, $C_{1-6}$-alkoxy, optionally substituted aryloxy or optionally substituted aryl. In some embodiments the acyl protection group is isobutuyryl (—C(O=)CH(CH$_3$)$_2$) (also referred to herein as iBu). The term isobuturyl may also be spelt isobutyryl.

Oxazaphospholidine Phosphoramidite

The invention provides an acetonitrile solution of a an oxazaphospholidine phosphoramidite, (also referred to as a nucleoside monomer, monomer or amidite herein), such as a nucleoside monomer of formula 1, comprising acetonitrile, the nucleoside monomer, and an aromatic heterocyclic solvent.

In some embodiments, the nucleoside monomer is of formula 1:

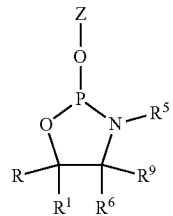

Formula 1 wherein Z is a nucleoside,

R$^5$ and R$^6$ are independently selected from the group consisting of hydrogen, alkyl, cyclo-alkyl, aryl, heteroaryl, substituted alkyl, substituted cyclo-alkyl, substituted aryl, and substituted heteroaryl, or R$^5$ and R$^6$ together form a heterocyclic ring comprising 3-16 carbon atoms, together with the N atom of formula 1;

R$^9$ is hydrogen;

R$^1$ is selected from the groups consisting of hydrogen and $C_{1-3}$ alkyl; and, R is selected from the groups consisting of aryl, heteroaryl, substituted aryl, substituted heteroaryl, nitro, halogen, cyano, silyl, substituted silyl, sulfone, substituted sulfone (aryl substituted sulfone), fluorene, and substituted fluorine;

wherein, when substituted, R may be substituted with a group selected from the group consisting of: $C_{1-4}$ alkyl group, $C_{6-14}$ aryl group $C_{1-4}$, alkoxy group, $C_{7-14}$ aralkyl group, $C_{1-4}$ alkyl, $C_{6-14}$ aryl group, $C_{1-4}$ alkoxy, $C_{6-14}$ aryl group, or $C_{6-14}$ aryl $C_{1-4}$ alkyl group. Multiple substitutions may be dependently or independently selected from the group consisting of: $C_{1-4}$ alkyl group, $C_{6-14}$ aryl group $C_{1-4}$, alkoxy group, $C_{7-14}$ aralkyl group, $C_{1-4}$ alkyl, $C_{6-14}$ aryl group, $C_{1-4}$ alkoxy, $C_{6-14}$ aryl group, or $C_{6-14}$ aryl $C_{1-4}$ alkyl group.

The R and $R^1$ (R/$R^1$) groups of the nucleoside of formula 1 provide a stereocenter which results in the formation of a Sp stereodefined phosphorothioate group 3' to the nucleoside when incorporated into an oligonucleotide.

In some embodiments, the stereocenter is in the L position, as illustrated in formula 1a. In some embodiments, the stereocenter is in the D position, as illustrated in formula 1b.

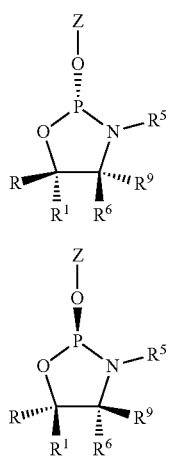

Formula 1a

Formula 1b

The monomer comprising the stereocenter created by the R and $R^1$ groups as shown in formula 1a is referred to as an L monomer herein which results in the formation of a Sp stereocenter.

The monomer comprising the stereocenter created by the R and $R^1$ groups as shown in formula 1b is referred to as a D monomer herein which results in the formation of a Rp stereocenter.

When substituted, R may be substituted with a group selected from the group consisting of: $C_{1-4}$ alkyl group, $C_{6-14}$ aryl group $C_{1-4}$, alkoxy group, $C_{7-14}$ aralkyl group, $C_{1-4}$ alkyl, $C_{6-14}$ aryl group, $C_{1-4}$ alkoxy, $C_{6-14}$ aryl group, or $C_{6-14}$ aryl $C_{1-4}$ alkyl group. Multiple substitutions may be dependently or independently selected from the group consisting of: $C_{1-4}$ alkyl group, $C_{6-14}$ aryl group $C_{1-4}$, alkoxy group, $C_{7-14}$ aralkyl group, $C_{1-4}$ alkyl, $C_{6-14}$ aryl group, $C_{1-4}$ alkoxy, $C_{6-14}$ aryl group, or $C_{6-14}$ aryl $C_{1-4}$ alkyl group.

In some embodiments R is selected from the groups consisting of aryl, heteroaryl, substituted aryl, substituted heteroaryl, nitro, halogen, cyano, silyl, substituted silyl, sulfone, substituted sulfone (aryl substituted sulfone), fluorene, and substituted fluorene.

In some embodiments R is selected from the group consisting of aryl, heteroaryl, substituted aryl and substituted heteroaryl.

In some embodiments R is aryl, such as phenyl.

In some embodiments, when R is substituted aryl, R may be substituted with halide, such as iodide, fluoride, bromide or chloride, such as phenyl substituted with halide, such as iodide, fluoride, bromide or chloride.

In some embodiments $R^1$ is hydrogen. In some embodiments $R^1$ is $C_{1-3}$ alkyl, such as methyl, ethyl or propyl. In some embodiments $R^1$ is methyl.

In some embodiments, R is aryl, such as phenyl and $R^1$ is hydrogen.

In some embodiments, R is aryl, such as phenyl, and $R^1$ is $C_{1-3}$ alkyl, such as methyl, ethyl or propyl.

In some embodiments R is

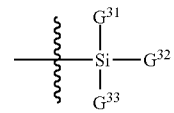

wherein $G^{31}$, $G^{32}$ and $G^{33}$ are independently selected from the groups consisting of $C_{1-4}$ alkyl, $C_{6-14}$ aryl$C_{1-4}$ alkoxy, $C_{7-14}$ aralkyl, $C_{1-4}$ alkyl$C_{6-14}$ aryl, $C_{1-4}$ alkoxy$C_{6-14}$ aryl, and $C_{6-14}$ aryl$C_{1-4}$ alkyl.

In some embodiments R is

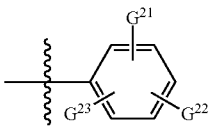

wherein $G^{21}$, $G^{22}$ and $G^{23}$ are independently hydrogen, nitro, halogen, cyano or $C_{1-3}$ alkyl.

In some embodiments R is

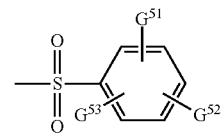

wherein $G^{51}$, $G^{52}$ and $G^{53}$ are independently hydrogen, nitro, halogen, cyano or $C_{1-3}$ alkyl or $C_{1-3}$ alkyloxy group.

In some embodiments $R^5$ and $R^6$ together form a heterocylic ring (with the cyclic nitrogen shown in Formula 1)—nucleoside monomers referred to as bicyclic oxazaphospholidine phosphoramidites. The heterocyclic ring may comprise, for example 3-16 carbon atoms, such as 4 carbons atoms.

Bicyclic Oxazaphospholidine Phosphoramidite Monomers

In some embodiments the monomer is a bicyclic oxazaphospholidine phosphoramidite monomer, e.g. in some embodiments $R^5$ and $R^6$ together form a heterocylic ring. In some embodiments $R^5$ and $R^6$ together form a heterocylic ring (with the cyclic nitrogen shown in Formula 1) which comprises 4 carbon atoms, making a total of five atoms in the heterocyclic ring (4 carbon and the nitrogen shown in Formula 1). For example, the compound of the invention may be of formula 2a or 2b:

Formula 2a

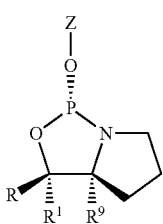

Formula 2b

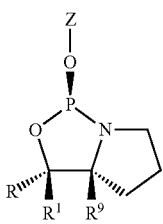

Wherein R, $R^1$, $R^9$ and Z are as according to formula 1.

In some embodiments $R^5$ and $R^6$ together form a heterocylic ring (with the cyclic nitrogen shown in Formula I) which comprises 4 carbon atoms, making a total of five atoms in the heterocyclic ring (4 carbon and the nitrogen shown in Formula 1), and R is aryl, such as phenyl, $R^1$ is hydrogen or methyl. $R^9$ is hydrogen.

The Z group above is a nucleoside where the 3' oxygen of the nucleoside is the exocyclic oxygen shown in formula 1, 1a, 1b, 2a or 2b. In some embodiments the Z group is a LNA nucleoside moiety. In some embodiments the Z group is a DNA nucleoside moiety. In some embodiment the compound of the invention may therefore be represented as the compound of formula 3a or 3b:

Formula 3a

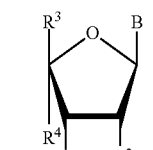

Formula 3b

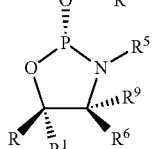

wherein, R, $R^1$, $R^5$, $R^6$ and $R^9$ are as per the compound of the invention;

B is a nucleobase,

In some embodiments B is a nucleobase selected from the group consisting of adenine, guanine, cytosine, thymidine, uracil, xanthine, hypoxanthine, 5-methylcytosine, isocytosine, pseudoisocytosine, 5-bromouracil, 5-propynyluracil, 6-aminopurine, 2-aminopurine, inosine, diaminopurine, and 2-chloro-6-aminopurine.

In some embodiments B is a purine nucleobase. In some embodiments B is a pyrimidine nucleobase. In some embodiments, B is a B is adenine. In some embodiments, B is thymidine. In some embodiments, B is guanine. In some embodiments, B is cytosine. In some embodiments, when B is cytosine, B is 5-methyl-cytosine.

In some embodiments, B is other than cytosine, for example, when the monomer is a D-DNA monomer, e.g. of formula 20 or 22. In some embodiments, e.g. when the monomer is a D-DNA-C, B is other than acetyl (Ac) protected cytosine.

It should be understood that for use in oligonucleotide synthesis the nucleobase group B may be protected in the amidite monomers (thymidine is often used without a protection group). Suitable protection groups include dimethyformamide (DMF), dimethoxytrityl (DMT) or an acyl protection group, such as isobutyryl (iBu), or an acetyl protection group (Ac) or a benzoyl protection group (Bz).

In some embodiments, e.g. when the monomer is a L-LNA-G, B is other than DMF protected guanine (G). $R^3$=is selected from the group consisting of $CH_2ODMTr$, $CH_2$-Alkyl-O-DMTr, CH-Me-O-DMTr, $CH_2OMMTr$, $CH_2$-Alkyl-O-MMTr, CH(Me)-O-MMTr, CH—$R^a$—O-DMTr$R^b$, and CH—$R^a$—O-MMTr$R^b$;

$R^2$ is selected from the groups consisting of halo, such as —F, amino, azido, —SH, —CN, —OCN, —$CF_3$, —$OCF_3$, —O($R^m$)-alkyl, —S($R^m$)-alkyl, —N($R^m$)-alkyl, —O($R^m$)-alkenyl, —S($R^m$)-alkenyl, —N($R^m$)-alkenyl; —O($R^m$)-alkynyl, —S($R^m$)-alkynyl or —N($R^m$)-alkynyl; O-alkylenyl-O-alkyl, alkynyl, alkaryl, aralkyl, O-alkaryl, O-aralkyl, $O(CH_2)_2SCH_3$, O—$(CH_2)_2$—O—N($R^m$)($R^n$) or O—$CH_2C$(=O)—N($R^m$)($R^n$), —O—$(CH_2)_2OCH_3$, and —O—$CH_3$, where each $R^m$ and $R^n$ are independently, H, an amino protecting group or substituted or unsubstituted $C_{1-10}$ alkyl;

$R^4$=is selected from the group consisting of alkyl, cycloalkyl, cyclo-heteroalkyl, O-alkyl, S-alkyl, NH-alkyl, and hydrogen; In some embodiments, $R^4$ is hydrogen. In some embodiments, $R^4$ is hydrogen, and $R^2$ is selected from the group consisting of —O—$CH_3$, and —O—$(CH_2)_2OCH_3$.

Or in some embodiments, $R^2$ and $R^4$ together designate a bivalent bridge, such as consisting of 1, 2, 3 groups/atoms selected from the group consisting of —C($R^aR^b$)—, —C($R^a$)=C($R^b$), —C($R^a$)=N, O, —Si($R^a$)$_2$—, S—, —$SO_2$—, —N($R^a$)—, and >C=Z;

wherein $R^a$ and, when present $R^b$, each is independently selected from hydrogen, optionally substituted $C_{1-6}$-alkyl, optionally substituted $C_{2-6}$-alkenyl, optionally substituted $C_{2-6}$-alkynyl, hydroxy, optionally substituted $C_{1-6}$-alkoxy, $C_{2-6}$-alkoxyalkyl, $C_{2-6}$-alkenyloxy, carboxy, $C_{1-6}$-alkoxycarbonyl, $C_{1-6}$-alkylcarbonyl, formyl, aryl, aryl-ioxy-carbonyl, aryloxy, arylcarbonyl, heteroaryl, hetero-aryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, where aryl and heteroaryl may be optionally substituted and where two geminal substituents $R^a$ and $R^b$ together may designate optionally substituted methylene (=$CH_2$), wherein for all chiral centers, asymmetric groups may be found in either R or S orientation.

In some embodiments, when incorporated into an oligonucleotide, the nucleoside (Z) confers a higher binding affinity to a complementary RNA target than an equivalent DNA nucleoside. Such nucleosides are referred to as high affinity nucleosides. Examples of high affinity nucleosides include 2'-O-MOE, 2'-fluoro, 2'-O-methyl, and LNA nucleosides. In the embodiments, where the nucleoside is a high affinity nucleoside $R^3$ may, for example, be $CH_2$—O-DMTr or $CH_2$—O-MMTr.

In some embodiments, $R^2$ is selected from the group consisting of fluoro (—F), —O—$(CH_2)_2OCH_3$, and —O—$C_{1-3}$ alkyl, such as —O—$CH_3$. In such embodiments, optionally $R^4$ is hydrogen.

In some embodiments, the nucleoside is a LNA nucleoside (also known as a bicyclic nucleoside) comprising a 2'-4' bridge (biradicle).

In some embodiments, $R^2$ and $R^4$ together designate a bivalent bridge selected from the group consisting of bridge —C($R^aR^b$)—O—, —C($R^aR^b$)C($R^aR^b$)—O—, —$CH_2$—O—, —$CH_2CH_2$—O—, —CH($CH_3$)—O—. In some embodiments, $R^2$ and $R^4$ designate the bivalent bridge —$CH_2$—O— (methylene-oxy also known as oxy-LNA) or —CH($CH_3$)—O— (methyl-methylene-oxy). The —CH($CH_3$)—O— bridge introduces a chiral center at the carbon atom within the bridge, in some embodiments this is in the S position (for example a nucleoside known in the art as (S)cET—see EP1984381)). In some embodiments, $R^2$ and $R^4$ designate the bivalent bridge —$CH_2$—O— wherein the bridge is in the beta-D position (beta-D-oxy LNA). In some embodiments, $R^2$ and $R^4$ designate the bivalent bridge —$CH_2$—O— wherein the bridge is in the alpha-L position (alpha-L-D-oxy LNA). In some embodiments, $R^2$ and $R^4$ designate the bivalent bridge —$CH_2$—S— (thio LNA), or —$CH_2$—$NH_2$— (amino LNA). In the embodiments where $R^2$ and $R^4$ together designate a bivalent bridge, $R^3$ may, for example be $CH_2$—O-DMTr or $CH_2$—O-MMTr.

In some embodiments where the nucleoside (Z) is a bicyclic nucleotides (LNA) such as beta-D-oxy LNA, R is aryl, such as phenyl, and $R^1$ is hydrogen or $C_{1-3}$ alkyl. In such am embodiment, $R^5$ and $R^6$ may together form a heterocylic ring, such as a five membered heterocyclic ring, as described herein (e.g. see formula 2a and 2b).

In some embodiments, the oxazaphospholidine phosphoramidite monomer is selected from the group consisting of formula 4a, 4b, 5a, 5b, 6a, 6b, 7a and 7b.

Formula 4a

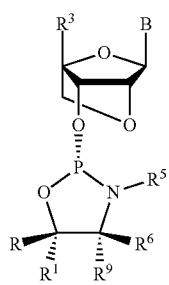

Formula 4b

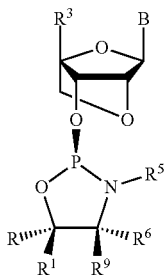

Formula 5a

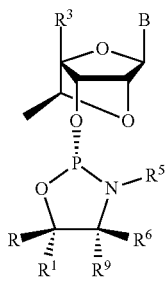

Formula 5b

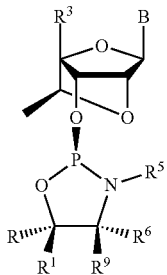

Formula 6a

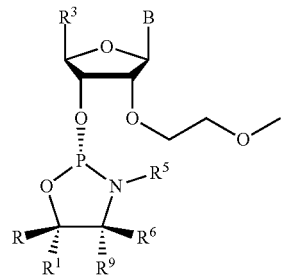

Formula 6b

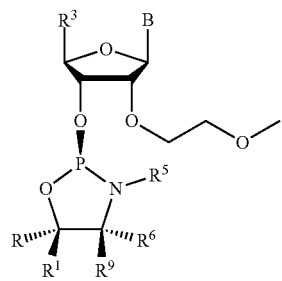

Formula 7a
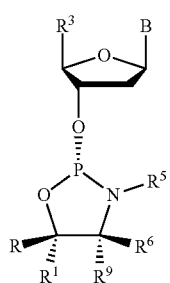

Formula 7b
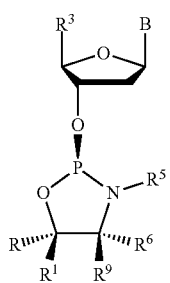

In some embodiments, the oxazaphospholidine phosphoramidite monomer is selected from the group consisting of formula 8a, 8b, 8c or 8d; or 9a, 9b, 9c or 9d:

formula 8a
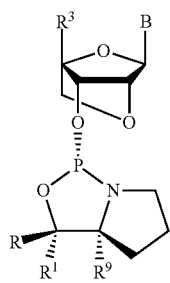

formula 8b
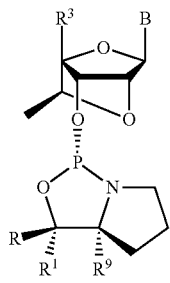

formula 8c
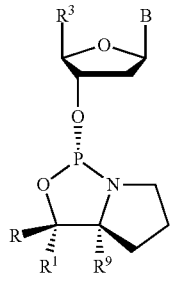

formula 8d
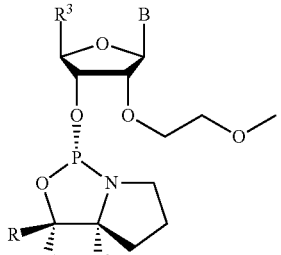

formula 9a
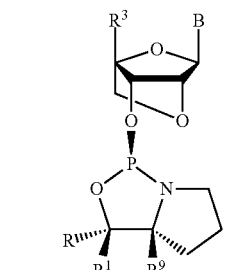

formula 9b
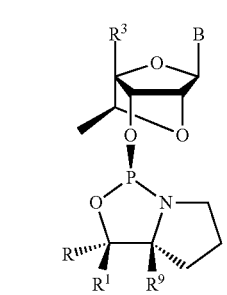

formula 9c
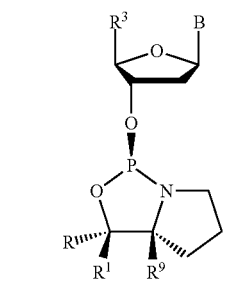

formula 9d
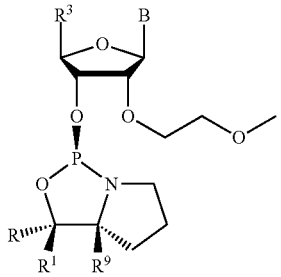

In some embodiments, the nucleobase B is adenine, such as Bz protected adenine. In some embodiments, the nucleobase B is thymine. In some embodiments, the monomer is a D-DNA-A monomer (e.g. the monomer is of formula 9c and the nucleobase B is adenine, such as Bz protected adenine). The examples illustrate that D-DNA-A monomers (e.g. of formula 9c), L-LNA-A monomers and L-LNA-T monomers (e.g. of formula 8a or 8b) show improved coupling when used in acetonitrile/aromatic heterocyclic solvents, as according to the invention.

DMF Protected L-LNA-G

As illustrated in the examples, DMF protected L-LNA-G monomers are poorly soluble in acetonitrile solvents.

In some embodiments, the oxazaphospholidine phosphoramidite monomer is not an L-LNA monomer comprising a DMF protected guanine nucleobase.

In some embodiments the DMF protected guanine group (B) has the following structure:

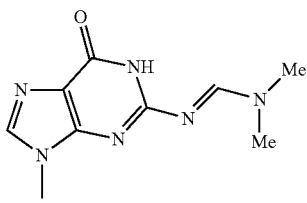 [SMILES: CN(C)/C=N/c1nc2c(ncn2C)c(=O)[nH]1]

In some embodiments, the oxazaphospholidine phosphoramidite monomer is not a monomer of formula 11 or 12:

Formula 11

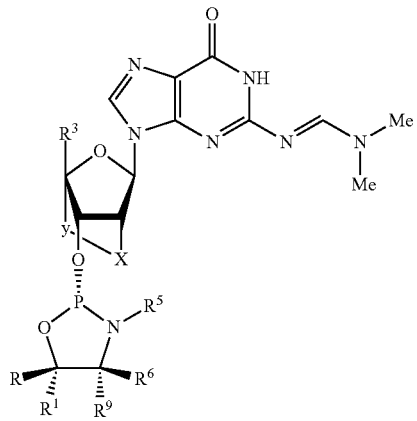

Formula 12

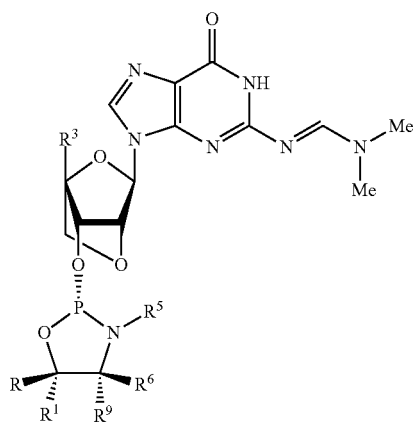

wherein R, $R^1$, $R^3$, $R^5$, $R^6$ & $R^9$ are as according to the monomer of formula 1, and wherein for the monomer of formula 11, X and Y together designate a bivalent bridge (e.g. as per $R^2$ and $R^4$ herein, such as a bridge selected from the group consisting of bridge —C($R^aR^b$)—O—, —C($R^aR^b$) C($R^aR^b$)—O—, —CH$_2$—O—, —CH$_2$CH$_2$—O—, —CH(CH$_3$)—O—. In some embodiments, X and Y designate the bivalent bridge —CH$_2$—O— (methylene-oxy also known as oxy-LNA) or —CH(CH$_3$)—O— (methyl-methylene-oxy). The —CH(CH$_3$)—O— bridge introduces a chiral center at the carbon atom within the bridge, in some embodiments this is in the S position (for example a nucleoside known in the art as (S)cET—see EP1984381)). In some embodiments, X and Y designate the bivalent bridge —CH$_2$—O— wherein the bridge is in the beta-D position (beta-D-oxy LNA). In some embodiments, X and Y designate the bivalent bridge —CH$_2$—O— wherein the bridge is in the alpha-L position (alpha-L-D-oxy LNA). In some embodiments, X and Y designate the bivalent bridge —CH$_2$—S— (thio LNA), or —CH$_2$—NH$_2$— (amino LNA). In the embodiments where X and Y together designate a bivalent bridge, $R^3$ may, for example be CH$_2$—O-DMTr or CH$_2$O-MMTr.

In some embodiments, the oxazaphospholidine phosphoramidite monomer is not a monomer of formula 13 or 14:

formula 13

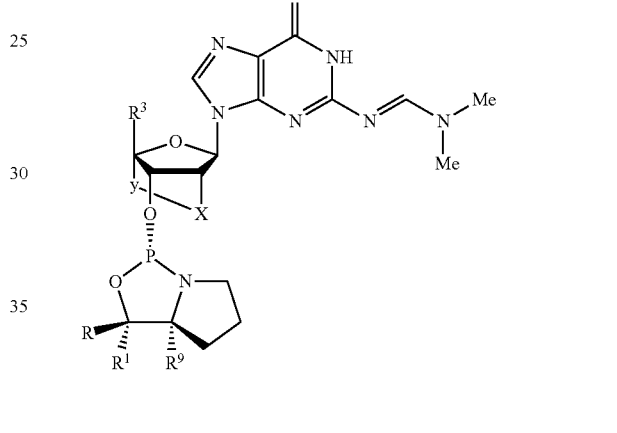

formula 14

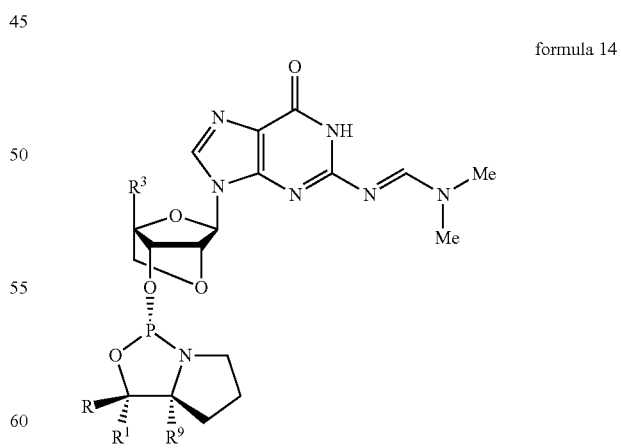

Wherein X, Y, R, $R^1$, $R^9$ and $R^3$ are as per formula 11 and 12. The exocyclic oxygen of the guanine base may optionally be protected, e.g. with a cyano group.

In some embodiments, the oxazaphospholidine phosphoramidite monomer is not a monomer of formula 15 or 16:

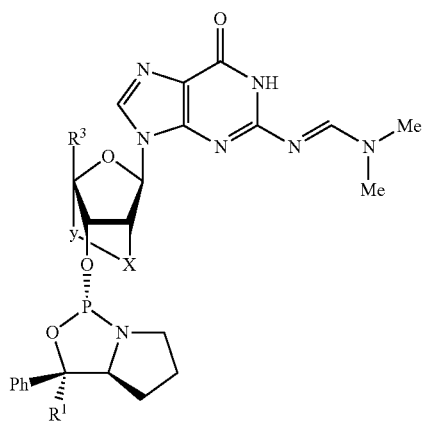

formula 15

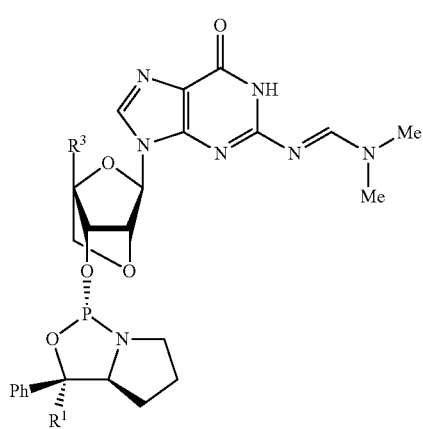

formula 16

Wherein X, Y, $R^1$ and $R^3$ are as per formula 11 and 12. The exocyclic oxygen of the guanine base may optionally be protected, e.g. with a cyano group. In some embodiments of formula 15 or 16, $R^1$ is hydrogen. In some embodiments of formula 15 or 16, $R^3$ is $CH_2$—O-DMTr or $CH_2$—O-MMTr. In some embodiments, the oxazaphospholidine phosphoramidite monomer of the invention comprises an acyl protected nucleoside (Z).

Acyl Protected L-LNA-G

As illustrated in the examples, DMF protected L-LNA-G monomers are poorly soluble in acetonitrile solvents. However, the inventors have identified that the use of acyl protection groups on the guanine nucleoside of L-LNA-G monomers overcomes the solubility problem. In some embodiments, the oxazaphospholidine phosphoramidite monomer is an L-LNA monomer comprising an acyl protected guanine nucleobase, such as an isobutyryl protected guanine. In some embodiments, the oxazaphospholidine phosphoramidite monomer is an L-LNA-G monomer of formula 23, 24, 25, 26, 27, 28, 29 or 30:

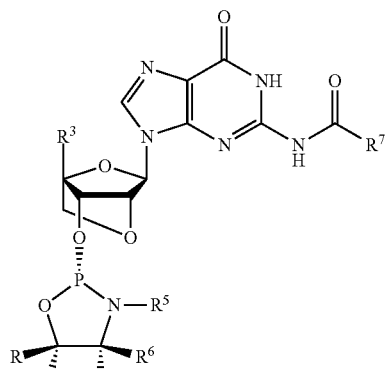

Formula 23

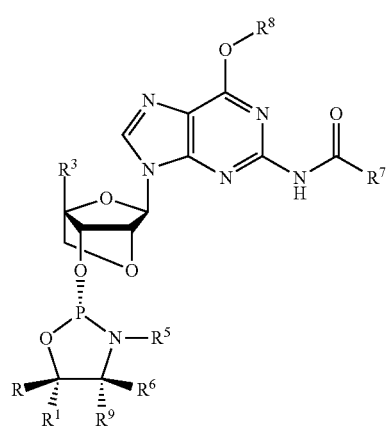

formula 24

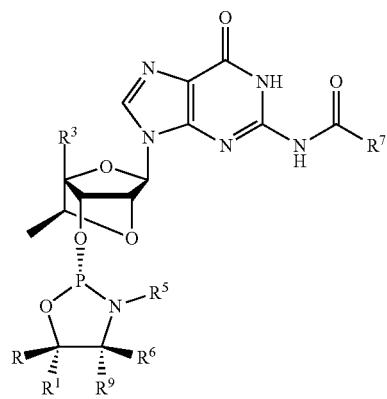

formula 25

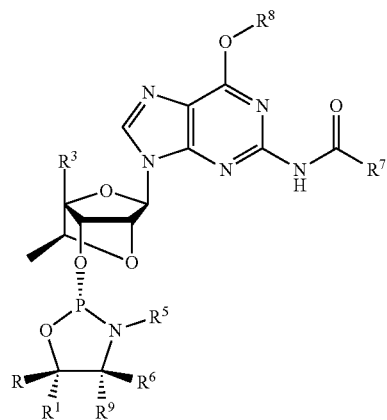

formula 26

-continued

Formula 27
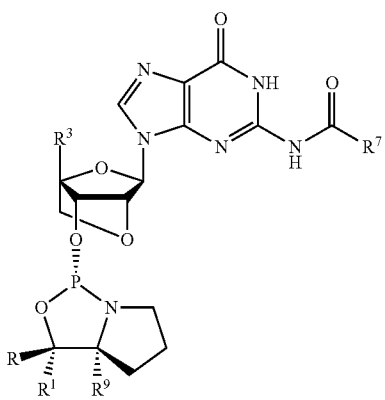

formula 28
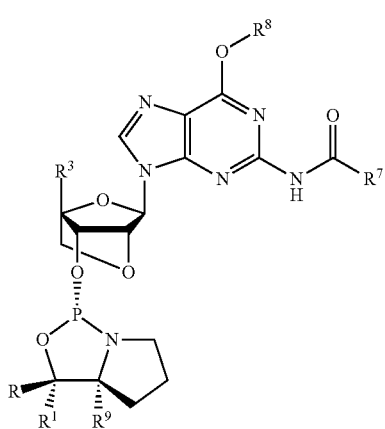

formula 29
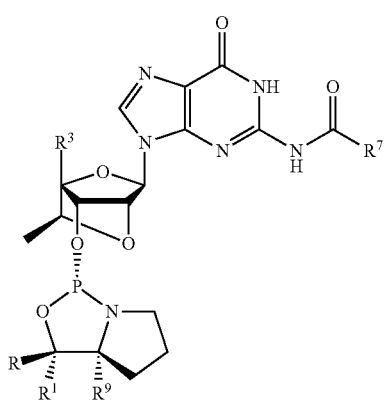

formula 30
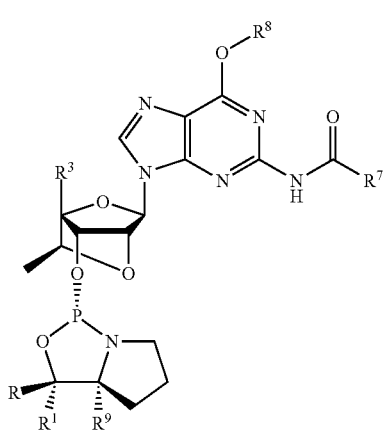

-continued formula 31
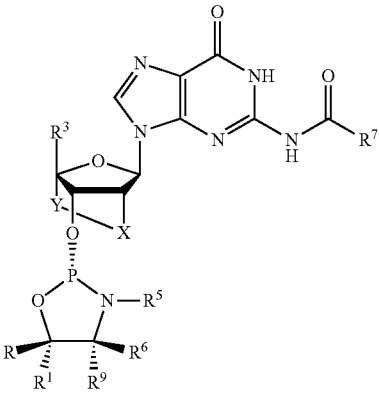

formula 32
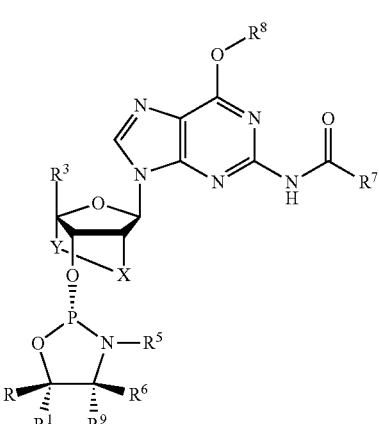

wherein, R, $R^1$, $R^2$, $R^3$, $R^4$, $R^5$, $R^9$ and $R^6$ are as per the compound of the invention, and —C(=O)—$R^7$ is the acyl protecting group on the exocyclic nitrogen of the guanine base, and $R^8$ when present is a protecting group on the guanine exocyclic oxygen. In some embodiments $R^8$ is cyanoethyl. In some embodiments, R is phenyl, $R^1$ is hydrogen or methyl, and $R^3$ is optionally $CH_2$—O-DMTr or $CH_2$—O-MMTr. In some embodiments, $R^7$ is isobutyryl. In formula's 31 and 32, Y and X are as per formula 11.

In some embodiments, the oxazaphospholidine phosphoramidite monomer is selected from the group consisting of an L-LNA-T, D-DNA-A, D-DNA-C, L-LNA-C, and L-LNA-G (other than DMF protected L-LNA-G) or a L-DNA-C and L-DNA-T oxazaphospholidine phosphoramidite monomer. As illustrated in the examples, these monomers show an improved coupling efficacy when used in the coupling solvent compositions of the invention, in addition to the solubility and stability benefits seen with in general for oxazaphospholidine phosphoramidite monomers.

Solvent Compositions (Solutions)

The invention provides for an acetonitrile solution comprising an oxazaphospholidine phosphoramidite monomer, acetonitrile and an aromatic heterocyclic solvent.

In some embodiments the acetonitrile solution further comprises an activator. Numerous activators for use in phosphoramidite oligonucleotide synthesis are known—they typically comprise acidic azole catalysts, such as 1H-tetrazole, 5-ethylthio-1H-tetrazole, 2-benzylthiotetrazole, and 4,5-dicyanoimidazole.

In some embodiments, the aromatic heterocyclic solvent has a pKa of about 4-about 7. In some embodiments, the aromatic heterocyclic solvent has a pKa of about 7-about 17 in water at 20° C.

In some embodiments, the aromatic heterocyclic solvent is an aromatic heterocyclic base.

In some embodiments, the aromatic heterocyclic solvent is an aromatic heterocyclic acid.

In some embodiments, the aromatic heterocyclic solvent is selected from the group consisting of pyridine, 2-picoline, 4-picoline, 3-picoline, lutidine, and pyrrole.

In some embodiments, the aromatic heterocyclic solvent is pyridine.

In some embodiments, the aromatic heterocyclic solvent is pyrrole.

In some embodiments, the aromatic heterocyclic solvent is 3-picoline.

In some embodiments, the concentration (v/v), of aromatic heterocyclic solvent in acetonitrile is between about 0.1% and about 50% (v/v). In some embodiments, the concentration (v/v), of aromatic heterocyclic solvent in acetonitrile is between about 0.5% and about 40% (v/v). In some embodiments, the concentration (v/v), of aromatic heterocyclic solvent in acetonitrile is between about 0.5% and about 30% (v/v). In some embodiments, the concentration (v/v), of aromatic heterocyclic solvent in acetonitrile is between about 0.5% and about 25% (v/v). In some embodiments, the concentration (v/v), of aromatic heterocyclic solvent in acetonitrile is between about 0.5% and about 10% (v/v). In some embodiments, the concentration (v/v), of aromatic heterocyclic solvent in acetonitrile is between about 0.5% and about 5% (v/v). In some embodiments, the concentration (v/v), of aromatic heterocyclic solvent in acetonitrile is between about 1% and about 5% (v/v). In some embodiments, the concentration (v/v), of aromatic heterocyclic solvent in acetonitrile is between about 1% and about 4% (v/v). In some embodiments, the concentration (v/v), of aromatic heterocyclic solvent in acetonitrile is between about 0.5% (v/v) and about 10% (v/v), such as between about 1% (v/v) and about 5% (v/v), such as between about 2-3% (v/v), such as about 2.5% (v/v). In these embodiments, optionally the aromatic heterocyclic base solvent is pyridine.

In some embodiments, wherein the aromatic heterocyclic solvent is pyridine, the concentration (v/v), of aromatic heterocyclic solvent in acetonitrile is between about 0.5% and about 10%, such as between about 1% and about 5%, such as between about 2-3%, such as about 2.5% or about 3.5%, or between about 2-4%.

In some embodiments, wherein the aromatic heterocyclic solvent is pyrrole, the concentration (v/v), of aromatic heterocyclic solvent in acetonitrile is between about 0.5% and about 10%, such as between about 1% and about 5%, such as between 2-4% or about 2-3%, such as about 2.5%.

In some embodiments, wherein the aromatic heterocyclic solvent is 3-picoline, the concentration (v/v), of aromatic heterocyclic solvent in acetonitrile is between about 0.5% and about 10%, such as between about 1% and about 5%, such as between 2-4%, or about 2-3%, such as about Activators Activators are reagents used prior to or during the coupling step of oligonucleotide synthesis which activate the phosphoramidiate monomer to allow coupling of the monomer to the 5' terminal group attached to the solid support or oligonucleotide chain.

In some embodiments, the acetonitrile solvent composition further comprises an activator.

In some embodiments, the activator is selected from the group consisting of CMPT (N-(Cyanomethyl)pyrrolidinium triflate (CMPT), N-(phenyl)imidazolium triflate (Ph IMT), benzimidazolium triflate (BIT), 4,5-dicyanoimidazole (DCI), tetrazole, and 5-(Benzylthio)-1H-tetrazole.

In some embodiments, the activator is 4,5-dicyanoimidazole (DCI).

In some embodiments, the solvent composition comprises about 0.5-about 2M DCI (or the other activators of claim 13, such 0.01 s about 1M DCI or the other activators of claim 13).

In some embodiments, the solvent composition further comprises N-methylimidazole, such as N-methylimidazole in a concentration of 0.01 about 1M N-methylimidazole, such as about 0.1M N-methylimidazole.

In some embodiments, the activator comprises N-methylimidazole. In some embodiments, the activator comprises 4,5-dicyanoimidazole (DCI), tetrazole, or 5-(Benzylthio)-1H-tetrazole. In some embodiments, the activator comprises 4,5-dicyanoimidazole (DCI), tetrazole, or 5-(Benzylthio)-1H-tetrazole and N-methylimidazole.

In some embodiments, the concentration of N-methylimidazole used is 0.01M-about 1M N-methylimidazole, such as about 0.1M N-methylimidazole. In some embodiments, the acetonitrile solution comprises N-methylimidazole in a concentration of 0.01M-about 1M N-methylimidazole, such as about 0.1M N-methylimidazole.

In some embodiments, the activator is DCI or tetrazole, or 5-(Benzylthio)-1H-tetrazole, which may be used at a concentration (e.g. in the acetonitrile solution of the invention) of about 0.5-about 2M, such as about 1M.

In some embodiments the activator is 4,5-dicyanoimidazole (DCI). In some embodiments, the solvent composition comprises about 0.5-about 2M DCI, such as about 1M DCI. It will be recognised that in order to optimise coupling efficacy, it may be necessary to optimize the amount of activator used, as is illustrated in the examples. In some embodiments the concentration of DCI activator uses is between 0.5M and 1M DCI. In some embodiments when the activator is DCI, the solvent composition further comprises N-methylimidazole (NMI), such as N-methylimidiazole in a concentration of 0.01-about 1M N-methylimidazole, such as about 0.1M N-methylimidazole. NMI is an agent which can enhance the solubility of other activators such as DCI.

Oligonucleotide Synthesis Method

The invention provides for a method for the synthesis of an oligonucleotide, said method comprising the method for coupling an oxazaphospholidine phosphoramidite monomer to a 5'-terminus of a solid support, a nucleoside or an oligonucleotide according to the invention.

The invention provides for a method for the synthesis of a stereodefined phosphorothioate oligonucleotide, comprising the step of:

a) deprotect a protected 5'-hydroxy terminus of a nucleoside, or oligonucleotide, attached to a solid support, b) coupling an oxazaphospholidine phosphoramidite monomer to the deprotected 5'-hydroxy terminus of a nucleoside or oligonucleotide, wherein said coupling reaction takes place in an acetonitrile solvent composition comprising acetonitrile and an aromatic heterocyclic solvent, to form a phosphite triester intermediate and c) oxidizing the phosphite triester intermediate with a sulfurizing reagent.

d) optionally repeating steps a)-c) for one or more further elongation cycles, e) deprotection and cleavage of the oligonucleotide from the solid support.

The method of the invention may comprise multiple further elongation cycles d), such as 2, 3, 4, 5, 6, 7, 8, 9, 10, 11, 12, 13, 14, 15, 16, 17, 18, 19, 20 or more further elongation cycles.

In some embodiments, after step c) or after step d), an optional amine wash step is performed. The amine wash step refers to an optional procedure used in oligonucleotide synthesis wherein prior to exposure of the oligonucleotide to the strong basic conditions used in the cleavage step the oligonucleotide is treated with a solution of a weak base in an organic solvent, such as treatment with 20% diethylamine in acetontrile, or 1:1 triethylamine/acetonitrile. The amine wash results in the removal of cyanoethyl phosphate protection groups without cleavage of the oligonucleotide from the solid support. The benefit of including an amine wash results in the avoidance of unwanted cyanothyl adducts, such as acrylonitrile, which form due to a side reaction of the cyanoethyl phosphate protection group, and heterocyclic bases, particularly thymine. Typically, the chiral auxiliary is cleaved from the oligonucleotide during the deprotection and cleavage from the solid support. Suitable deprotection/cleavage may performed at a temperature of about 55° C. in concentrated ammonium hydroxide, for example.

In some embodiments, after step e) the oligonucleotide may be purified. The purification step may use any suitable method for oligonucleotide purification such as ion exchange purification or reversed phase chromatography, or both ion exchange purification and reversed phase chromatography. In some embodiments purification comprises the sequential steps: a) ion exchange purification, b) desalting, e.g. via diafiltration, followed by c) lyophilisation and d) reversed phase chromatography. Prior to purification it is typical that the ammonium hydroxide is either removed or at least diluted. Alternatively, DMT-ON reversed phase purification followed by detritylation is also an option for purifying oligonucleotides (see Capaldi and Scozzari, Chapter 14, Antisense Drug Technology: Principles, Strategies, and Applications, CRC Press 2008.

In some embodiments, after step e) or after the optional purification step, the oligonucleotide may be conjugated. Alternatively conjugation may be performed during oligonucleotide synthesis.

In some embodiments the oligonucleotide produced by the method of the invention, stereodefined phosphorothioate oligonucleotide, is an antisense oligonucleotide or a mixed sequence oligonucleotide. In some embodiments the stereodefined phosphorothioate oligonucleotide comprises both stereodefined phosphorothioate internucleoside linkages and stereorandom phosphorothioate internucleoside linkages.

As the oxazaphospholidine phosphoramidite monomer introduce either a Sp or Rp phosphorothioate internucleoside linkage the method of the invention may be used to synthesize a stereodefined oligonucleotide. The invention therefore provides for improved methods of synthesising stereodefined phosphorothioate oligonucleotides.

The improvements includes the provision of solutions of oxazaphospholidine phosphoramidite monomers, such as those described herein, with enhanced solubility of the monomers, as compared to acetonitrile solutions of the monomers without the aromatic heterocyclic solvent; or the provision of more stable solutions of oxazaphospholidine phosphoramidite monomers, such as those described herein, with enhanced stability of the solutions of the monomers, as compared to acetonitrile solutions of the monomers without the aromatic heterocyclic solvent; or the provision of more reactive solutions of oxazaphospholidine phosphoramidite monomers, such as those described herein, with enhanced reactivity of the monomers, as compared to acetonitrile solutions of the monomers without the aromatic heterocyclic solvent. The skilled person will appreciate that the single of combined benefits of having higher solubility, more stable solutions, and higher reactivity, will result in a more effective synthesis and a more reliable and enhanced yield of oligonucleotide product. The benefits may also include the avoidance or reduction of unwanted side-reactions, resulting in a higher product purity.

In some embodiments, the 5' terminus is a —OH group attached to a solid support. The —OH group may be directly attached to the solid support e.g. via a linker, such as unilinker, or may be part of a nucleoside or oligonucleotide which is attached to the linker or solid support.

In some embodiments the oligonucleotide synthesis method is a solid phase phosphoramidite synthesis, wherein at least one of the coupling steps is as according to the coupling method of the invention.

The oligonucleotide synthesis method of the invention may comprise the steps of:

a) providing a solid support with a free 5'-OH group, b) activation of an oxazaphospholidine phosphoramidite monomer, c) coupling the activated oxazaphospholidine phosphoramidite monomer to the free '5-OH as according to the method of the invention, to form a phosphotriester intermediate, d) oxidizing the phosphotriester intermediate with a sulfurizing reagent, such as xanthan hydride, e) capping any free —OH groups, for example using acetic anhydride, f) deprotect the $R^3$ group on the oxazaphospholidine phosphoramidite monomer, g) optionally repeating steps b)-f), h) deprotecting any remaining protection groups (global deprotection) and cleaving the oligonucleotide from the solid support, for example by treatment with ammonium hydroxide at 60° C., wherein the free —OH group of the solid support may optionally be attached to a nucleoside or oligonucleotide chain attached to said solid support.

The solid support may be provided in a protected from, with the 5'OH group protected e.g. by a DMT group. Prior to step a), the solid support (or the terminal nucleoside attached thereto) may be be-blocked (de-tritylated) to provide the free 5'-OH group.

In some embodiments, steps b) to f) are repeated 7-25 times in the oligonucleotide synthesis, such as 7-16 times. In some embodiments the reiteration of steps b)-f) are consecutive cycles in the oligonucleotide synthesis.

Exemplary scheme for phosphoramidite oligonucleotide synthesis using oxazaphospholidine phosphoramidite monomers:

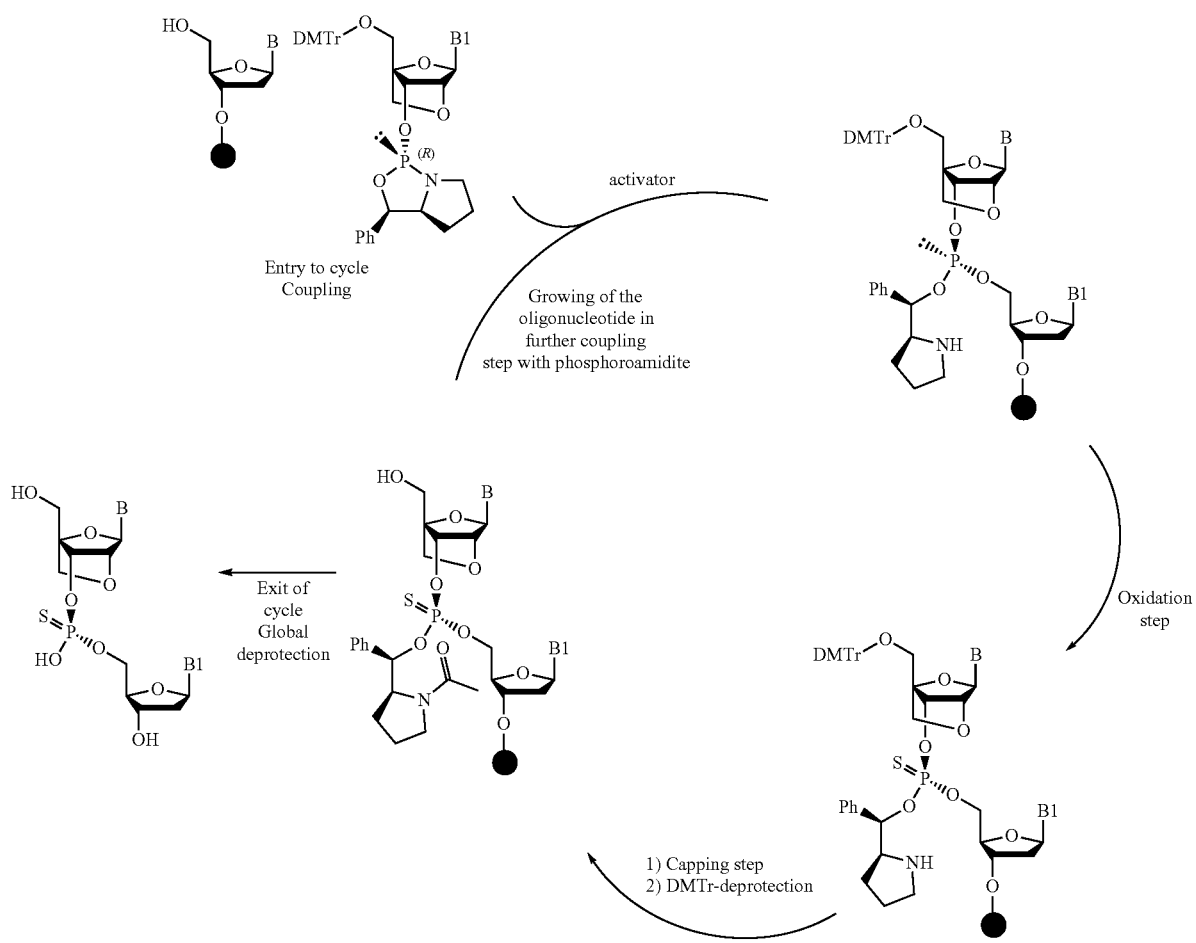

In some embodiments, in addition to incorporation of stereodefined phosphorothioate internucleoside linkages, the method of synthesis may, through use of standard phosphoramidite monomers, incorporate stereorandom internucleoside linkages.

Stereodefined Phosphorothioate Oligonucleotides

Typically, oligonucleotide phosphorothioates are synthesised as a random mixture of Rp and Sp phosphorothioate linkages (also referred to as a diastereomeric mixture). In the method of the present invention, phosphorothioate oligonucleotides are provided where at least one of the phosphorothioate linkages of the oligonucleotide is stereodefined, i.e. is either Rp or Sp in at least 75%, such as at least 80%, or at least 85%, or at least 90% or at least 95%, or at least 97%, such as at least 98%, such as at least 99%, or (essentially) all of the oligonucleotide molecules present in the oligonucleotide sample. Stereodefined oligonucleotides comprise at least one phosphorothioate linkage which is stereodefined. The term stereodefined, may be used to describe a defined chirality of one or more phosphorothioate internucleoside linkages as either Rp or Sp, or may be used to described a oligonucleotide which comprises such a (or more) phosphorothioate internucleoside linkage. It is recognised that a stereodefined oligonucleotide may comprise a small amount of the alternative stereoisomer at any one position, for example Wan et al reports a 98% stereoselectivity for the gapmers reported in NAR, November 2014.

LNA Oligonucleotide

An LNA oligonucleotide is an oligonucleotide which comprises at least one LNA nucleoside. The LNA oligonucleotide may be an antisense oligonucleotide.

The term oligonucleotide as used herein is defined as it is generally understood by the skilled person as a molecule comprising two or more covalently linked nucleosides. For use as an antisense oligonucleotide, oligonucleotides are typically synthesised as 7-30 nucleotides in length.

The term "antisense oligonucleotide" as used herein is refers to oligonucleotides capable of modulating expression of a target gene by hybridizing to a target nucleic acid, in particular to a contiguous sequence on a target nucleic acid. An antisense oligonucleotide can also be defined by it's complementary to a target nucleic acid. Antisense oligonucleotides are single stranded. Antisense oligonucleotides are not essentially double stranded and are not therefore siRNAs. An antisense oligonucleotide comprises a contiguous nucleotide which is complementary to a target nucleic acid. Antisense oligonucleotides typically comprise one or more modified internucleoside linkages, and may by way of a non-limiting example be in the form of a LNA gapmer or a mixed wing gapmer. In other embodiments the oligonucleotide may be an LNA mixmers (LNA and non-LNA nucleotides, e.g. LNA and DNA (see e.g. WO2007/112754 hereby incorporated by reference), or LNA and 2'-O-MOE nucleotides, or LNA, DNA and 2'O-MOE nucleotides), or a LNA totalmers (only LNA nucleotides—see. E.g. WO2009/043353 hereby incorporated by reference).

The term "modified internucleoside linkage" is defined as generally understood by the skilled person as linkages other than phosphodiester (PO) linkages, that covalently couples two nucleosides together. Modified internucleoside linkages are particularly useful in stabilizing oligonucleotides for in vivo use, and may serve to protect against nuclease cleavage. A phosphorothioate internucleoside linkage is particularly useful due to nuclease resistance, beneficial pharmakokinetics and ease of manufacture. In some embodiments at least 70%, such as at least 80 or such as at least 90% of the internucleoside linkages in the oligonucleotide, or contiguous nucleotide sequence thereof, are phosphorothioate. In some embodiments all of the internucleoside linkages of the oligonucleotide, or contiguous nucleotide sequence thereof, are phosphorothioate, wherein at least one of the phosphorothioate internucleoside linkages is a stereodefined phosphorothioate internucleoside linkage (originating from the incorporation of the oxazaphospholidine phosphoramidite monomer into the oligonucleotide during oligonucleotide synthesis). Further internucleoside linkers are disclosed in WO2009/124238 (incorporated herein by reference).

The term nucleobase includes the purine (e.g. adenine and guanine) and pyrimidine (e.g. uracil, thymine and cytosine) moiety present in nucleosides and nucleotides which form hydrogen bonds in nucleic acid hybridization. In the context of the present invention the term nucleobase also encompasses modified nucleobases which may differ from naturally occurring nucleobases, but are functional during nucleic acid hybridization. In some embodiments the nucleobase moiety is modified by modifying or replacing the nucleobase. In this context "nucleobase" refers to both naturally occurring nucleobases such as adenine, guanine, cytosine, thymidine, uracil, xanthine and hypoxanthine, as well as non-naturally occurring variants. Such variants are for example described in Hirao et al (2012) Accounts of Chemical Research vol 45 page 2055 and Bergstrom (2009) Current Protocols in Nucleic Acid Chemistry Suppl. 37 1.4.1.

Nucleotides are the building blocks of oligonucleotides and polynucleotides, and for the purposes of the present invention include both naturally occurring and non-naturally occurring nucleotides. In nature, nucleotides, such as DNA and RNA nucleotides comprise a ribose sugar moiety, a nucleobase moiety and one or more phosphate groups (which is absent in nucleosides). Modified nucleosides and nucleotides are modified as compared to the equivalent DNA or RNA nucleoside/tide by the introduction of a modification to the ribose sugar moiety, the nucleobase moiety, or in the case of modified nucleotides, the internucleoside linkage. Nucleosides and nucleotides may also interchangeably be referred to as "units" or "monomers".

The term "modified nucleoside" or "nucleoside modification" as used herein refers to nucleosides modified as compared to the equivalent DNA or RNA nucleoside by the introduction of one or more modifications of the sugar moiety or the (nucleo)base moiety. The term modified nucleoside may also be used herein interchangeably with the term "nucleoside analogue" or modified "units" or modified "monomers". Examples of modified nucleosides are described in the separate section "Oligomer modifications" and its sub-sections.

Acyl Protected Exocyclic Nitrogen

The exocyclic nitrogen group of guanine is illustrated below (encircled). This group is protected by an acyl group in the monomer used in the invention. The oxygen group may optionally also be protected, e.g. with a cyano group.

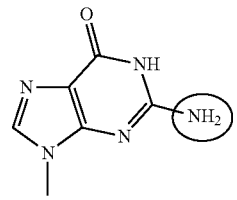

Locked Nucleic Acid Nucleosides (LNA).

LNA nucleosides are modified nucleosides which comprise a linker group (referred to as a biradicle or a bridge) between C2' and C4' of the ribose sugar ring of a nucleotide (i.e. the embodiment where $R^2$ and $R^4$ together designate a bivalent bridge).

These nucleosides are also termed bridged nucleic acid or bicyclic nucleic acid (BNA) in the literature.

In some embodiments, the oxazaphospholidine phosphoramidite monomer is or comprises a LNA nucleoside, for example the monomer may be of formula 17 or formula 18

Formula 17

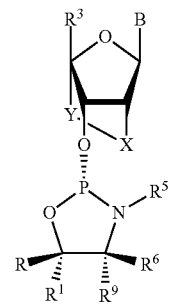

Formula 18

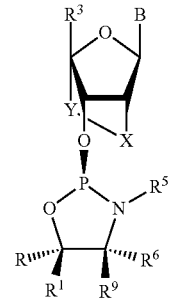

Wherein B designates the nucleobase; R, $R^1$, $R^6$, $R^3$, $R^9$, $R^5$ are as according to formula 1.

In some embodiments of formula 17, B is other than DMF protected guanine. In some embodiments B is either adenine or thymine. In some embodiments B is DMF protected adenine.

X designates a group selected from the list consisting of —C($R^aR^b$)—, —C($R^a$)=C($R^b$)—, —C($R^a$)=N—, —O—, —Si($R^a$)$_2$—, —S—, —SO$_2$—, —N($R^a$)—, and >C=Z In some embodiments, X is selected from the group consisting of: —O—, —S—, NH—, NR$^a$R$^b$, —CH$_2$—, CR$^a$R$^b$, —C(=CH$_2$)—, and —C(=CR$^a$R$^b$)—

In some embodiments, X is —O—

Y designates a group selected from the group consisting of —C($R^aR^b$)—, —C($R^a$)=C($R^b$)—, —C($R^a$)=N—, —O—, —Si($R^a$)$_2$—, —S—, —SO$_2$—, —N($R^a$)—, and >C=Z In some embodiments, Y is selected from the group consisting of: —CH$_2$—, —C(R$^a$R$^b$)—, —CH$_2$CH$_2$—, —C(R$^a$R$^b$)—C(R$^a$R$^b$), —CH$_2$CH$_2$CH$_2$, —C(R$^a$R$^b$)C(R$^a$R$^b$)C(R$^a$R$^b$)—, —C(R$^a$)=C(R$^b$)—, and —C(R$^a$)=N—

In some embodiments, Y is selected from the group consisting of: —CH$_2$—, —CHR$^a$—, —CHCH$_3$—, CR$^a$R$^b$— or —X—Y— together designate a bivalent linker group (also referred to as a radicle) together designate a bivalent linker group consisting of 1, 2, or 3 groups/atoms selected from the group consisting of —C(R$^a$R$^b$)—, —C(R$^a$)=C(R$^b$)—, —C(R$^a$)=N—, —O—, —Si(R$^a$)$_2$—, —S—, —SO$_2$—, —N(R$^a$)—, and >C=Z, In some embodiments, —X—Y— designates a biradicle selected from the groups consisting of: —X—CH$_2$—, —X—CR$^a$R$^b$—, —X—CHR$^a$—, —X—C(HCH$_3$)—, —O—Y—, —O—CH$_2$—, —S—CH$_2$—, —NH—CH$_2$—, —O—CHCH$_3$—, —CH$_2$—O—CH$_2$, —O—CH(CH$_3$CH$_3$)—, —O—CH$_2$—CH$_2$—, OCH$_2$—CH$_2$—CH$_2$—, —O—CH$_2$OCH$_2$—, —O—NCH$_2$—, —C(=CH$_2$)—CH$_2$—, —NR$^a$—CH$_2$—, N—O—CH$_2$, —S—CR$^a$R$^b$— and —S—CHR$^a$—.

In some embodiments —X—Y— designates —O—CH$_2$— or —O—CH(CH$_3$)—.

and R$^a$ and, when present R$^b$, each is independently selected from hydrogen, optionally substituted C$_{1-6}$-alkyl, optionally substituted C$_{2-6}$-alkenyl, optionally substituted C$_{2-6}$-alkynyl, hydroxy, optionally substituted C$_{1-6}$-alkoxy, C$_{2-6}$-alkoxyalkyl, C$_{2-6}$-alkenyloxy, carboxy, C$_{1-6}$-alkoxycarbonyl, C$_{1-6}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di(C$_{1-6}$-alkyl)amino, carbamoyl, mono- and di(C$_{1-6}$-alkyl)-aminocarbonyl, amino-C$_{1-6}$-alkyl-aminocarbonyl, mono- and di(C$_{1-6}$-alkyl)amino-C$_{1-6}$-alkyl-aminocarbonyl, C$_{1-6}$-alkyl-carbonylamino, carbamido, C$_{1-6}$-alkanoyloxy, sulphono, C$_{1-6}$-alkylsulphonyloxy, nitro, azido, sulphanyl, C$_{1-6}$-alkyl-thio, halogen, where aryl and heteroaryl may be optionally substituted and where two geminal substituents R$^a$ and R$^b$ together may designate optionally substituted methylene (=CH$_2$), wherein for all chiral centers, asymmetric groups may be found in either R or S orientation.

R$^{10}$ may be hydrogen or in some embodiments may be selected from the group consisting of: optionally substituted C$_{1-6}$-alkyl, optionally substituted C$_{2-6}$-alkenyl, optionally substituted: alkynyl, hydroxy, C$_{1-6}$-alkoxy, C$_{2-6}$-alkoxyalkyl, C$_{2-6}$-alkenyloxy, carboxy, C$_{1-6}$-alkoxycarbonyl, C$_{1-6}$"alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di(C$_{1-6}$-alkyl)amino, carbamoyl, mono- and di(C$_{1-6}$-alkyl)-aminocarbonyl, amino-C$_{1-6}$-alkyl-aminocarbonyl, mono- and di(C$_{1-6}$-alkyl)amino-C$_{1-6}$-alkyl-aminocarbonyl, C$_{1-6}$-alkyl-carbonylamino, carbamido, C$_{1-6}$-alkanoyloxy, sulphono, C$_{1-6}$-alkylsulphonyloxy, nitro, azido, sulphanyl, C$_{1-6}$-alkyl-thio, halogen, where aryl and heteroaryl may be optionally substituted, and where two geminal substituents together may designate oxo, thioxo, imino, or optionally substituted methylene.

In some embodiments R$^{10}$ is selected from C$_{1-6}$ alkyl, such as methyl, and hydrogen.

In some embodiments R$^{10}$ is hydrogen.

In some embodiments, R$^a$ is either hydrogen or methyl. In some embodiments, when present, R$^b$ is either hydrogen or methyl.

In some embodiments, one or both of R$^a$ and R$^b$ is hydrogen

In some embodiments, one of R$^a$ and R$^b$ is hydrogen and the other is other than hydrogen In some embodiments, one of R$^a$ and R$^b$ is methyl and the other is hydrogen In some embodiments, both of R$^a$ and R$^b$ are methyl.

In some embodiments, the biradicle —X—Y— is —O—CH$_2$—, and R$^{10}$ is hydrogen. In some embodiments, the biradicle —X—Y— is —S—CH$_2$—, and R$^{10}$ is hydrogen.

In some embodiments, the biradicle —X—Y— is —NH—CH$_2$—, and R$^{10}$ is hydrogen.

In some embodiments, the biradicle —X—Y— is —O—CH$_2$—CH$_2$— or —O—CH$_2$—CH$_2$—CH$_2$—, and R$^{10}$ is hydrogen.

In some embodiments, the biradicle —X—Y— is —O—CH$_2$—, and R$^{10}$ is C$_{1-6}$ alkyl, such as methyl.

In some embodiments, the biradicle —X—Y— is —O—CR$^a$R$^b$—, wherein one or both of R$^a$ and R$^b$ are other than hydrogen, such as methyl, and R$^{10}$ is C$_{1-6}$ alkyl, such as methyl.

In some embodiments, the biradicle —X—Y— designate the bivalent linker group —O—CH(CH$_2$OCH$_3$)— (2'O-methoxyethyl bicyclic nucleic acid—Seth at al., 2010, J. Org. Chem., 2010, 75 (5), pp 1569-1581). In some embodiments, the biradicle —X—Y— designate the bivalent linker group —O—CH(CH$_2$CH$_3$)—(2'O-ethyl bicyclic nucleic acid—Seth at al., 2010, J. Org. Chem). In some embodiments, the biradicle —X—Y— is —O—CHR$^a$—, and R$^{10}$ is hydrogen.

In some embodiments, the biradicle —X—Y— is —O—CH(CH$_2$OCH$_3$)—, and R$^{10}$ is hydrogen. Such LNA nucleosides are also known as cyclic MOEs in the art (cMOE) and are disclosed in WO07090071.

In some embodiments, the biradicle —X—Y— designate the bivalent linker group —O—CH(CH$_3$)— in either the R— or S— configuration. In some embodiments, the biradicle —X—Y— together designate the bivalent linker group —O—CH$_2$—O—CH$_2$— (Seth at al., 2010, J. Org. Chem). In some embodiments, the biradicle —X—Y— is —O—CH(CH$_3$)—, and R$^{10}$ is hydrogen. Such 6' methyl LNA nucleosides are also known as cET nucleosides in the art, and may be either (S)cET or (R)cET stereoisomers, as disclosed in WO07090071 (beta-D) and WO2010/036698 (alpha-L).

In some embodiments, the biradicle —X—Y— is —O—CR$^a$R$^b$—, wherein in neither R$^a$ or R$^b$ is hydrogen, and R$^{10}$ is hydrogen. In some embodiments, R$^a$ and R$^b$ are both methyl.

In some embodiments, the biradicle —X—Y— is —S—CHR$^a$—, and R$^{10}$ is hydrogen.

In some embodiments, the biradicle —X—Y— is —C(=CH$_2$)—C(R$^a$R$^b$)—, such as —C(=CH$_2$)—CH$_2$—, or —C(=CH$_2$)—CH(CH$_3$)—, and R$^{10}$ is hydrogen.

In some embodiments the biradicle —X—Y— is —N(—OR$^a$)—, and R$^{10}$ is hydrogen. In some embodiments R$^a$, a is C$_{1-6}$ alkyl such as methyl. In some embodiments, the biradicle —X—Y— together designate the bivalent linker group —O—NR$^a$—CH$_3$—(Seth at al., 2010, J. Org. Chem). In some In some embodiments the biradicle —X—Y— is —N(R$^a$)$^a$, and R" is hydrogen. In some embodiments R$^a$ is C$_{1-6}$-alkyl such as methyl. In some embodiments, and R$^{10}$ is C$_{1-6}$ alkyl such as methyl. In such an embodiment, the biradicle —X—Y— may be selected from —O—CH$_2$— or —O—C(HCR$^a$)—, such as —O—C(HCH$_3$)—.

In some embodiments, the biradicle is —CR$^a$R$^b$—O—CR$^a$R$^b$—, such as CH$_2$—O—CH$_2$—, and R$^{10}$ is hydrogen. In some embodiments R$^a$ is C$_{1-6}$ alkyl such as methyl.

In some embodiments, the biradicle is —O—CR$^a$R$^b$—O—CR$^a$R$^b$—, such as O—CH$_2$—O—CH$_2$—, and R$^{10}$ is hydrogen. In some embodiments R$^a$ is C$_{1-6}$ alkyl such as methyl.

It will be recognized than, unless specified, the LNA nucleosides may be in the beta-D or alpha-L stereoisoform.

As illustrated in the examples, in some embodiments of the invention the LNA nucleosides are or comprise beta-D-oxy-LNA nucleosides, such as where the 2'-4' bridge is as per formula I, and where X is oxygen, Y is CH$_2$, and R$^{10}$ is hydrogen.

DNA Nucleosides

In some embodiments, the oxazaphospholidine phosphoramidite monomer is or comprises a DNA nucleoside, for example the monomer may be of formula 19 or formula 20:

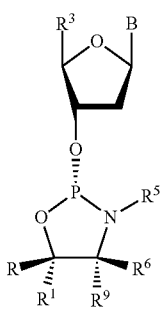

Formula 19

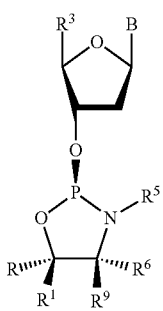

Formula 20

Wherein B designates the nucleobase; R, R$^1$, R$^6$, R$^3$, R$^9$, R$^5$ are as according to formula 1. In some embodiments of formula 20, B is adenine, such as protected adenine, such as Bz protected adenine.

In some embodiments, the oxazaphospholidine phosphoramidite monomer is as according to formula 21 and 22:

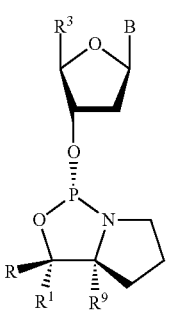

formula 21

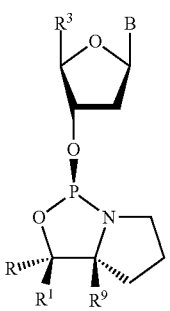

formula 22

Wherein B designates the nucleobase; R, R$^1$, R$^3$, R$^9$, are as according to formula 1. In some embodiments of formula 20 or 22, B is adenine, such as protected adenine, such as Bz protected adenine. In some embodiments of the monomer of formula 19, 20, 21, or 22, R is phenyl, and R$^1$ is either hydrogen or methyl. In some embodiments of the monomer of formula 19, 20, 21 or 22, R$^3$ is CH$_2$—O-DMTr or CH$_2$—O-MMTr.

Oligonucleotides Comprising DNA and/or Affinity Enhancing Nucleosides

In some embodiments, the oligonucleotide is a DNA phosphorothioate oligonucleotide. DNA phosphorothioate oligonucleotides comprise only DNA nucleosides, and in some embodiments may comprise only stereodefined phosphorothioate internucleoside linkages. DNA phosphorothioates may for example be 18-25 nucleotides in length.

In some embodiments, the oligonucleotide comprises one or more affinity enhancing nucleosides, such as LNA or 2' substituted nucleosides described herein. Affinity enhancing nucleosides, such as 2'-O-MOE or 2'-Omethyl are often used in antisense oligonucleotides, either in combination with other nucleosides, such as DNA nucleosides, in the form of, e.g. mixmers or gapmers, or may be used in fully sugar modified oligonucleotides, where all of the nucleosides are other than DNA or RNA.

In some embodiments the oligonucleotide synthesised by the method of the invention may be a gapmer, and LNA gapmer, or a mixed wing gapmer.

In some embodiments of the method of the invention, the oxazaphospholidine phosphoramidite monomer is of formula 33 (FIG. 17).

In some embodiments of the method of the invention, the oxazaphospholidine phosphoramidite monomer is of formula 34 (FIG. 17).

In some embodiments of the method of the invention, the oxazaphospholidine phosphoramidite monomer is of formula 35 (FIG. 17).

In some embodiments of the method of the invention, the oxazaphospholidine phosphoramidite monomer is of formula 36 (FIG. 17).

In some embodiments of the method of the invention, the oxazaphospholidine phosphoramidite monomer is of formula 37 (FIG. 17).

In some embodiments of the method of the invention, the oxazaphospholidine phosphoramidite monomer is of formula 38 (FIG. 17).

In some embodiments of the method of the invention, the oxazaphospholidine phosphoramidite monomer is of formula 39 (FIG. 17).

In some embodiments of the method of the invention, the oxazaphospholidine phosphoramidite monomer is of formula 40 (FIG. 17).

In some embodiments of the method of the invention, the oxazapholidine phosphoramidite monomer is of formula 41 (FIG. 18).

In some embodiments of the method of the invention, the oxazapholidine phosphoramidite monomer is of formula 42 (FIG. 18).

In some embodiments of the method of the invention, the oxazapholidine phosphoramidite monomer is of formula 43 (FIG. 18).

In some embodiments of the method of the invention, the oxazapholidine phosphoramidite monomer is of formula 44 (FIG. 18).

In some embodiments of the method of the invention, the oxazapholidine phosphoramidite monomer is of formula 45 (FIG. 18).

In some embodiments of the method of the invention, the oxazapholidine phosphoramidite monomer is of formula 46 (FIG. 18).

In some embodiments of the method of the invention, the oxazapholidine phosphoramidite monomer is of formula 47 (FIG. 18).

In some embodiments of the method of the invention, the oxazapholidine phosphoramidite monomer is of formula 48 (FIG. 18).

In some embodiments the oxazapholidine phosphoramidite monomer is a DNA monomer.

In some embodiments the oxazapholidine phosphoramidite monomer is a LNA monomer. In some embodiments, the oxazapholidine phosphoramidite monomer is a LNA-A (either a D-LNA-A or an L-LNA-A) monomer.

In some embodiments, the oxazapholidine phosphoramidite monomer is a LNA-C (either a D-LNA-A or an L-LNA-A) monomer.

In some embodiments, the oxazapholidine phosphoramidite monomer is an L-LNA-G (either a D-LNA-A or an L-LNA-A) monomer, such as a L-LNA-G wherein the exocyclic nitrogen of the guanine residue is protected with an acyl protection group such as isobuturyl.

In some embodiments, oxazapholidine phosphoramidite monomer is other than an L-LNA-G monomer wherein the exocyclic nitrogen on the guanine residue is protected with a DMF protection group. In some embodiments, oxazapholidine phosphoramidite monomer is other than an D-LNA-G monomer.

In some embodiments, the oxazapholidine phosphoramidite monomer is other than a LNA-T monomer, such as D-LNA-T or L-LNA-T.

In some embodiments, the oxazapholidine phosphoramidite monomer is other than a LNA-T monomer, such as D-LNA-T or L-LNA-T or a D-LNA-G monomer.

In some embodiments, the oxazapholidine phosphoramidite monomer is a DNA monomer, or is a LNA monomer selected from the group consisting of a LNA-A monomer, a LNA-C monomer and an acyl protected L-LNA-G monomer.

In some embodiments, the oxazapholidine phosphoramidite monomer is other than a LNA-T monomer, a D-LNA-G monomer, or a DMF protected L-LNA-G monomer.

Gapmer

The term gapmer as used herein refers to an antisense oligonucleotide which comprises a region of RNase H recruiting oligonucleotides (gap) which is flanked 5' and 3' by one or more affinity enhancing modified nucleosides (flanks). Various gapmer designs are described herein. Headmers and tailmers are oligonucleotides capable of recruiting RNase H where one of the flanks are missing, i.e. only one of the ends of the oligonucleotide comprises affinity enhancing modified nucleosides. For headmers the 3' flank is missing (i.e. the 5' flank comprise affinity enhancing modified nucleosides) and for tailmers the 5' flank is missing (i.e. the 3' flank comprises affinity enhancing modified nucleosides). In some embodiments the stereo-defined phosphorothioate oligonucleotide is a gapmer oligonucleotide such as an LNA gapmer oligonucleotide.

LNA Gapmer

The term LNA gapmer is a gapmer oligonucleotide wherein at least one of the affinity enhancing modified nucleosides is an LNA nucleoside.

Mixed Wing Gapmer

The term mixed wing gapmer refers to a LNA gapmer wherein the flank regions comprise at least one LNA nucleoside and at least one non-LNA modified nucleoside, such as at least one 2' substituted modified nucleoside, such as, for example, 2'-O-alkyl-RNA, 2'-O-methyl-RNA, 2'-alkoxy-RNA, 2'-O-methoxyethyl-RNA (MOE), 2'-amino-DNA, 2'-Fluoro-DNA, arabino nucleic acid (ANA), 2'-fluoro-ANA and 2'-F-ANA nucleoside(s). In some embodiments the mixed wing gapmer has one flank which comprises LNA nucleosides (e.g. 5' or 3') and the other flank (3' or 5' respectfully) comprises 2' substituted modified nucleoside(s).

Length

When referring to the length of a nucleotide molecule as referred to herein, the length corresponds to the number of monomer units, i.e. nucleotides, irrespective as to whether those monomer units are nucleotides or nucleotide analogues. With respect to nucleotides, the terms monomer and unit are used interchangeably herein.

The method of the present invention is particularly suitable for the purification of short oligonucleotides, for example, consisting of 7 to 30 nucleotides, such as 7-10, such as 7, 8, 9, 10 or 10 to 20 nucleotides, such as 12 to 18 nucleotides, for example, 12, 13, 14, 15, 16, 17 or 18 nucleotides.

Mixed Sequence Oligonucleotides

The oligonucleotide synthesised using the method of the invention may be a mixed sequence oligonucleotide. The invention provides for a method for the synthesis of manufacture of a mixed sequence oligonucleotide. A mixed sequence oligonucleotide comprises at least two such as at least three of at least four different base moieties (e.g. selected from the group consisting of A, T, C, or G, wherein C is optionally 5-methyl-cytosine). Antisense oligonucleotides are typically mixed sequence oligonucleotides.

FURTHER EMBODIMENTS OF THE INVENTION

A Embodiments

1. A process for coupling an oxazapholidine phosphoramidite monomer to a 5'-terminus of a nucleoside or oligonucleotide, or a hydroxyl group attached to a solid support, comprising the step of reacting the nucleoside, oligonucleotide, or solid support, with the oxazapholidine phosphoramidite monomer, wherein said reaction takes place in an acetonitrile solvent composition comprising acetonitrile and an aromatic heterocyclic solvent, and optionally an activator.

2. The process according to A embodiment 1, wherein the oxazapholidine phosphoramidite monomer is a compound of formula I

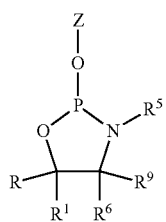

formula I wherein Z is a nucleoside,

R⁵ and R⁶ are independently selected from the group consisting of hydrogen, alkyl, cyclo-alkyl, aryl, heteroaryl, substituted alkyl, substituted cyclo-alkyl, substituted aryl, and substituted heteroaryl, or R⁵ and R⁶ together form a heterocyclic ring comprising 3-16 carbon atoms, together with the N atom of formula 1;

R⁹ is hydrogen;

R¹ is selected from the groups consisting of hydrogen and $C_{1-3}$ alkyl; and,

R is selected from the groups consisting of aryl, heteroaryl, substituted aryl, substituted heteroaryl, nitro, halogen, cyano, silyl, substituted silyl, sulfone, substituted sulfone (aryl substituted sulfone), fluorene, and substituted fluorine;

wherein, when substituted, R may be substituted with a group selected from the group consisting of: $C_{1-4}$ alkyl group, $C_{6-14}$ aryl group $C_{1-4}$, alkoxy group, $C_{7-14}$ aralkyl group, $C_{1-4}$ alkyl, $C_{6-14}$ aryl group, $C_{1-4}$ alkoxy, $C_{6-14}$ aryl group, or $C_{6-14}$ aryl $C_{1-4}$ alkyl group. Multiple substitutions may be dependently or independently selected from the group consisting of: $C_{1-4}$ alkyl group, $C_{6-14}$ aryl group $C_{1-4}$, alkoxy group, $C_{7-14}$ aralkyl group, $C_{1-4}$ alkyl, $C_{6-14}$ aryl group, $C_{1-4}$ alkoxy, $C_{6-14}$ aryl group, or $C_{6-14}$ aryl $C_{1-4}$ alkyl group.

3. The process according to A embodiment 1 or 2, wherein the aromatic heterocyclic solvent has a pKa of 4-7 or from 7-17 in water at 20° C.

4. The process according to any one of A embodiments 1-3, wherein the aromatic heterocyclic solvent is an aromatic heterocyclic base.

5. The process according to any one of A embodiments 1-3, wherein the aromatic heterocyclic solvent is an aromatic heterocyclic acid.

6. The process according to any one of A embodiments 1-3, wherein the aromatic heterocyclic solvent is selected from the group consisting of pyridine, 2-picoline, 4-picoline, 3-picoline, lutidine, and pyrrole.

7. The process according to any one of A embodiments 1-6, wherein the concentration (v/v), of aromatic heterocyclic solvent in acetonitrile is between about 0.1% and about 50% (v/v).

8. The process according to any one of A embodiments 1-6, wherein the concentration (v/v), of aromatic heterocyclic solvent in acetonitrile is between about 0.5% and about 10%, such as between about 1% and about 5%, such as between about 2-3%, such as about 2.5%.

9. The process according to any one of A embodiments 1-8, wherein the activator comprises N-methylimidazole.

10. The process according to any one of A embodiments 1-9, wherein the solvent composition comprises N-methylimidazole in a concentration of 0.01-about 1M N-methylimidazole, such as about 0.1M N-methylimidazole.

11. The process according to any one of A embodiments 1-10, wherein the activator comprises 4,5-dicyanoimidazole (DCI), tetrazole, or 5-(Benzylthio)-1H-tetrazole.

12. The process according to any one of A embodiments 1-11, wherein the solvent composition comprises about 0.5-about 2M DCI (or the other activators of A embodiment 11), such as about 1M DCI (or the other activators of A embodiment 11).

13. The process according to any one of A embodiments 1-12, wherein the oxazaphospholidine phosphoramidite monomer is a compound of

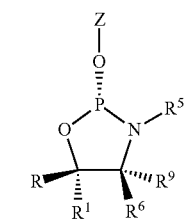

Formula 1a

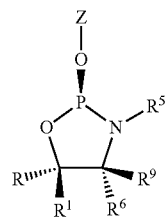

Formula 1b wherein Z, R, R¹, R⁶, R⁹ and R⁵ are all as according to A embodiment 2.

14. The process according to any one of A embodiments 1-11, A embodiment 1, wherein R is selected from the group consisting of aryl, heteroaryl, substituted aryl and substituted heteroaryl.

15. The process according to any one of A embodiments 1-11, wherein R is aryl, such as phenyl.

16. The process according to any one of A embodiments 1-13, wherein R¹ is hydrogen.

17. The process according to any one of A embodiments 1-13, wherein R¹ is $C_{1-3}$ alkyl, such as methyl.

18. The process according to any one of A embodiments 1-15, wherein R⁵ and R⁶ together form a heterocyclic ring comprising 3-16 (e.g. 4) carbon atoms, together with the N atom of formula (I), (Ia) or (1b).

19. The process according to any one of A embodiments 1-15, wherein R⁵ and R⁶ together form a heterocyclic ring comprising 4 carbon atoms, together with the N atom of formula (I), (Ia) or (1b).

20. The process according to any one of A embodiments 1-19 wherein, the phosphoramidite monomer compound is of formula 2a or 2b

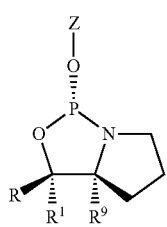

Formula 2a

Formula 2b

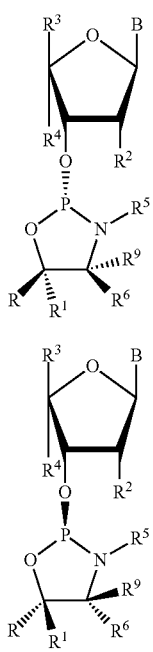

wherein Z, R, and $R^1$ are as according to any one of A embodiments 2-17.

21. The process according to any one of A embodiments 1-20, wherein the oxazaphospholidine phosphoramidite monomer compound is of formula 3a or 3b Formula 3a

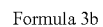

Formula 3b wherein,

R, $R^1$, $R^5$, $R^6$ and $R^9$ are as according to any one of A embodiments 2-18;

B is the a nucleobase group;

$R^3$=is selected from the group consisting of $CH_2ODMTr$, $CH_2$-Alkyl-O-DMTr, CH-Me-O-DMTr, $CH_2OMMTr$, $CH_2$-Alkyl-O-MMTr, CH(Me)-O-MMTr, CH—$R^a$—O-DMTr$R^b$, and CH—$R^a$—O-MMTr$R^b$; $R^2$ is selected from the groups consisting of halo, such as —F, amino, azido, —SH, —CN, —OCN, —$CF_3$, —$OCF_3$, —O($R_m$)-alkyl, —S($R_m$)-alkyl, —N($R_m$)-alkyl, —O($R_m$)-alkenyl, —S($R_m$)-alkenyl, —N($R_m$)—alkenyl; —O($R_m$)-alkynyl, —S($R_m$)-alkynyl or —N($R_m$)-alkynyl; O-alkylenyl-O-alkyl, alkynyl, alkaryl, aralkyl, O-alkaryl, O-aralkyl, O($CH_2$)$_2SCH_3$, O—($CH_2$)$_2$—O—N($R_m$)($R_n$) or O—$CH_2$C(=O)—N($R_m$)($R_n$), —O—($CH_2$)$_2OCH_3$, and —O—$CH_3$, where each $R_m$ and $R_n$ are independently, H, an amino protecting group or substituted or unsubstituted $C_{1-10}$ alkyl;

$R^4$=is selected from the group consisting of alkyl, cycloalkyl, cyclo-heteroalkyl, O-alkyl, S-alkyl, NH-alkyl, and hydrogen;

or $R^2$ and $R^4$ together designate a bivalent bridge consisting of 1, 2, 3 groups/atoms selected from the group consisting of —C($R^aR^b$)—, —C($R^a$)=C($R^b$), —C($R^a$)=N, O, —Si($R^a$)$_2$—, S—, —$SO_2$—, —N($R^a$)—, and >C=Z;

wherein $R^a$ and, when present $R^b$, each is independently selected from hydrogen, optionally substituted $C_{1-6}$-alkyl, optionally substituted $C_{2-6}$-alkenyl, optionally substituted $C_{2-6}$-alkynyl, hydroxy, optionally substituted $C_{1-6}$-alkoxy, $C_{2-6}$-alkoxyalkyl, $C_{2-6}$-alkenyloxy, carboxy, $C_{1-6}$-alkoxycarbonyl, $C_{1-6}$-alkylcarbonyl, formyl, aryl, aryl-ioxy-carbonyl, aryloxy, arylcarbonyl, heteroaryl, hetero-aryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, where aryl and heteroaryl may be optionally substituted and where two geminal substituents Ra and Rb together may designate optionally substituted methylene (=$CH_2$), wherein for all chiral centers, asymmetric groups may be found in either R or S orientation.

22. The process according to any one of A embodiments 1-21, wherein the oxazaphospholidine phosphoramidite monomer is selected from the group consisting of formula 4a, 4b, 5a, 5b, 6a, 6b, 7a and 7b.

Formula 4a

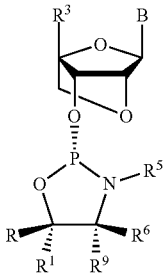

Formula 4b

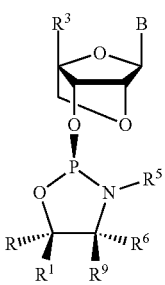

Formula 5a

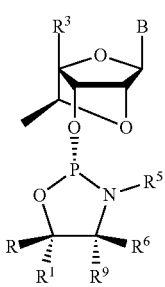

-continued

Formula 5b
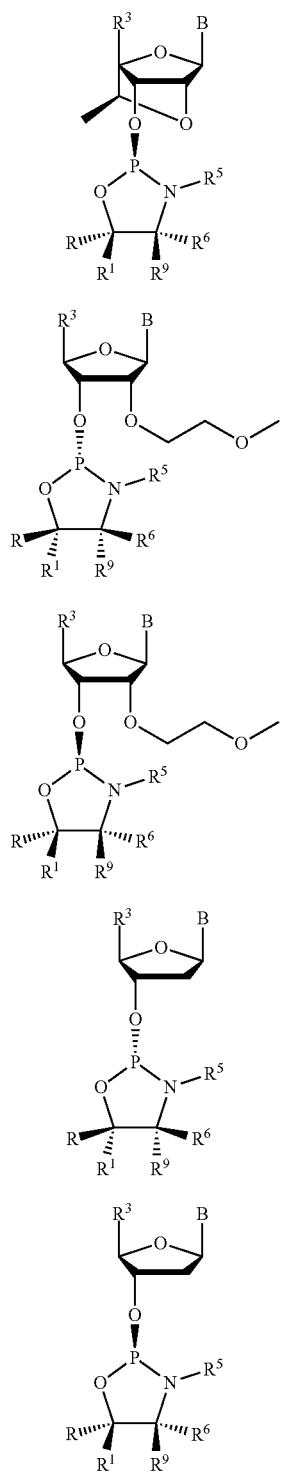

Formula 6a

Formula 6b

Formula 7a

Formula 7b

23. The process according to any one of A embodiments 1-23, wherein the oxazaphospholidine phosphoramidite monomer comprises a nucleobase moiety is a purine or a pyrimidine, such as a nucleobase selected from the group consisting of adenine, guanine, uracil, thymine and cytosine, isocytosine, pseudoisocytosine, 5-methyl cytosine, 5-thiozolo-cytosine, 5-propynyl-cytosine, 5-propynyl-uracil, 5-bromouracil 5-thiazolo-uracil, 2-thio-uracil, 2'thio-thy- mine, inosine, diaminopurine, 6-aminopurine, 2-aminopurine, 2,6-diaminopurine and 2-chloro-6-aminopurine.

24. The process according to any one of A embodiments 1-23, wherein B in the oxazaphospholidine phosphoramidite monomer is either adenine or thymine.

25. The process according to any one of A embodiments 1-24, wherein the oxazaphospholidine phosphoramidite monomer is selected from the group consisting of formula 8a or formula 8b Formula 8a
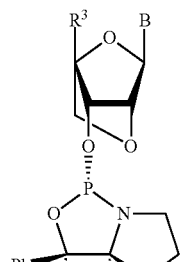

Formula 8b
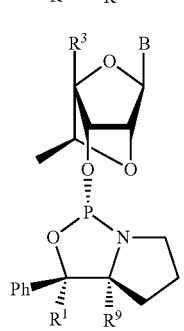

wherein B is either adenine or thymine, and wherein R, $R^1$, $R^3$ and $R^9$ are as according to any one of A embodiments 1-24, wherein when B is adenine it may be protected, e.g. with benzoyl).

26. The process according to any one of A embodiments 1-24, wherein the oxazaphospholidine phosphoramidite monomer is as according to formula 9c Formula 9c
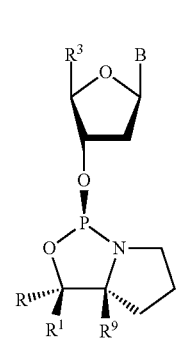

wherein B is adenine, and wherein R, $R^1$, $R^3$ and $R^9$ are as according to any one of A embodiments 1-24, wherein when B is adenine it may be protected, e.g. with benzoyl.

27. The process according to any one of A embodiments 1-26, wherein R is phenyl, $R^1$ is hydrogen or methyl, $R^9$ is hydrogen, and $R^3$ is selected from the group consisting of $CH_2ODMTr$, $CH_2$-Alkyl-O-DMTr, CH-Me-O-DMTr, CH$_2$OMMTr, CH$_2$-Alkyl-O-MMTr, CH(Me)-O-MMTr, CH—R$^a$—O-DMTrR$^b$, and CH—R$^a$—OMMTrR$^b$, such as CH$_2$—O-DMTr or CH$_2$—O-MMTr.

28. An acetonitrile solution comprising the oxazaphospholidine phosphoramidite monomer according to any one of A embodiments 1-27, acetonitrile and an aromatic heterocyclic solvent.

29. The acetonitrile solution according to A embodiment 28, wherein the concentration of the oxazaphospholidine phosphoramidite monomer is between about 0.05 M and about 2 M, such as about 0.1 M to about 1M, such as about 0.1M-about 0.2M, such as about 0.15 M, or about 0.175 M, or about 0.2 M.

30. The acetonitrile solution according to A embodiment 28 or 29, wherein the aromatic heterocyclic solvent is as according to any one of A embodiments 1-28.

31. The acetonitrile solution according to any one of A embodiments 28-30, wherein the oxazaphospholidine phosphoramidite monomer is as according to any one of A embodiments 1-28.

32. The acetonitrile solution according to any one of A embodiments 28-31, wherein the concentration of aromatic heterocyclic solvent in acetonitrile is between about 0.1% and about 50% (v/v).

33. The acetonitrile solution according to any one of A embodiments 28-32, wherein the concentration of aromatic heterocyclic solvent in acetonitrile is between about 0.5% and about 10%, such as between about 1% and about 5% (v/v), such as between about 2-3%, such as about 2.5%.

34. The acetonitrile solution according to any one of A embodiments 28-33, wherein the acetonitrile solution further comprises an activator, such as an activator according to any one of A embodiments 9-12.

35. The acetonitrile solution according to A embodiment 34 wherein the acetonitrile solution comprises about 0.5-about 2M DCI, such as about 1M DCI.

36. The acetonitrile solution according to any one of A embodiments 34 and 35, wherein the acetonitrile solution comprises about 0.01-about 1M N-methylimidazole, such as about 0.1M N-methylimidazole.

37. A method for the synthesis of an oligonucleotide, said method comprising the process according to any one of A embodiments 1-27.

38. The method for synthesis of an oligonucleotide according to A embodiment 37, said method comprising the steps of:
  a) providing a solid support with a free 5'-OH group,
  b) activation of an oxazaphospholidine phosphoramidite monomer according to any one of A embodiments 21-27, for example in the solution according to any one of A embodiments 1-36,
  c) coupling the activated oxazaphospholidine phosphoramidite monomer to the free '5-OH as according to the process of any one of A embodiments 1-27, to form a phosphotriester intermediate,
  d) oxidizing the phosphotriester intermediate with a sulfurizing reagent, such as xanthan hydride,
  e) capping any free —OH groups, for example using acetic anhydride,
  f) deprotect the R$^3$ group on the oxazaphospholidine phosphoramidite monomer,
  g) optionally repeating steps b)-f),
  h) deprotecting any remaining protection groups (global deprotection) and cleaving the oligonucleotide from the solid support, for example by treatment with ammonium hydroxide at 60° C., wherein the free —OH group of the solid support may optionally be attached to a nucleoside or oligonucleotide chain attached to said solid support.

39. A method for dissolving oxazaphospholidine phosphoramidite monomer, such as a monomer according to any one of A embodiments 1-27, said method comprising adding the monomer to a solvent composition comprising acetonitrile and an aromatic heterocyclic solvent, and optionally an activator.

40. The use of an aromatic heterocyclic solvent to enhance the stability and/or solubility and/or reactivity of an oxazaphospholidine phosphoramidite monomer, such as the monomer according to any one of A embodiments 1-27, in acetonitrile.

41. The process, method, acetonitrile solution, or use according to any one of the preceding A embodiments, wherein the oxazaphospholidine phosphoramidite monomer is other than an L-LNA-guanine monomer, wherein guanine is DMF protected.

Embodiments

1. A method for the synthesis of a stereodefined phosphorothioate oligonucleotide, comprising the step of:
  a) deprotect a protected 5'-hydroxy terminus of a nucleoside, or oligonucleotide, attached to a solid support,
  b) coupling an oxazaphospholidine phosphoramidite monomer to the deprotected 5'-hydroxy terminus of a nucleoside or oligonucleotide, wherein said coupling reaction takes place in an acetonitrile solvent composition comprising acetonitrile and an aromatic heterocyclic solvent, to form a phosphite triester intermediate and
  c) oxidizing the phosphite triester intermediate with a sulfurizing reagent.
  d) optionally repeating steps a)-c) for one or more further elongation cycles,
  e) deprotection and cleavage of the oligonucleotide from the solid support.

2. A method according to B embodiment 2, wherein said method comprises multiple further elongation cycles (d).

3. The method according to B embodiment 3, wherein the stereodefined phosphorothioate oligonucleotide is an antisense oligonucleotide.

4. A method for coupling an oxazaphospholidine phosphoramidite monomer to a 5'-terminus of a nucleoside or oligonucleotide, comprising the step of reacting the nucleosideor oligonucleotide, with an oxazaphospholidine phosphoramidite monomer, wherein said reaction takes place in an acetonitrile solvent composition comprising acetonitrile and an aromatic heterocyclic solvent.

5. The method according to any one of B embodiments 1-4, wherein the aromatic heterocyclic solvent has a pKa of 4-7 or from 7-17 in water at 20° C.

6. The method according to any one of B embodiments 1-5, wherein the aromatic heterocyclic solvent is an aromatic heterocyclic base.

7. The method according to any one of B embodiments 1-5, wherein the aromatic heterocyclic solvent is an aromatic heterocyclic acid.

8. The method according to any one of B embodiments 1-5, wherein the aromatic heterocyclic solvent is selected from the group consisting of pyridine, 2-picoline, 4-picoline, 3-picoline, lutidine, and pyrrole.

9. The method according to any one of B embodiments 1-8, wherein the aromatic heterocyclic solvent is pyridine.

10. The method according to any one of B embodiments 1-9, wherein the concentration (v/v), of aromatic heterocyclic solvent in acetonitrile is between about 0.1% and about 50% (v/v), such as between about 0.5% and about 25%.

11. The method according to any one of B embodiments 1-9, wherein the concentration (v/v), of aromatic heterocyclic solvent in acetonitrile is between about 0.5% and about 10%, such as between about 1% and about 5%, such as between about 2-4%, such as about 2.5%, or about 3.5%.

12. The method according to any one of B embodiments 1-11, wherein the acetonitrile solvent composition further comprises an activator.

13. The method according to B embodiment 12, wherein the activator is selected from the group consisting of CMPT (N-(Cyanomethyl)pyrrolidinium triflate (CMPT), N-(phenyl)imidazolium triflate (PhIMT), benzimidazolium triflate (BIT), 4,5-dicyanoimidazole (DCI), tetrazole, and 5-(Benzylthio)-1H-tetrazole.

14. The method according to B embodiment 13, wherein the activator is 4,5-dicyanoimidazole (DCI).

15. The method according to any one of B embodiments 1-14, wherein the solvent composition comprises about 0.5-about 2M DCI (or the other activators of B embodiment 13), such as about 1M DCI (or the other activators of B embodiment 13).

16. The method according to any one of B embodiments 12-15, wherein the solvent composition further comprises N-methylimidazole, such as N-methylimidazole in a concentration of 0.01-about 1M N-methylimidazole, such as about 0.1M N-methylimidazole.

17. The method according to any one of B embodiments 1-16, wherein the oxazaphospholidine phosphoramidite monomer is a compound of formula I

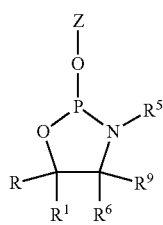

formula I wherein Z is a nucleoside, $R^5$ and $R^6$ are independently selected from the group consisting of hydrogen, alkyl, cyclo-alkyl, aryl, heteroaryl, substituted alkyl, substituted cyclo-alkyl, substituted aryl, and substituted heteroaryl, or $R^5$ and $R^6$ together form a heterocyclic ring comprising 3-16 carbon atoms, together with the N atom of formula 1;

$R^9$ is hydrogen;

$R^1$ is selected from the groups consisting of hydrogen and $C_{1-3}$ alkyl; and, R is selected from the groups consisting of aryl, heteroaryl, substituted aryl, substituted heteroaryl, nitro, halogen, cyano, silyl, substituted silyl, sulfone, substituted sulfone (aryl substituted sulfone), fluorene, and substituted fluorine;

wherein, when substituted, R may be substituted with a group selected from the group consisting of: $C_{1-4}$ alkyl group, $C_{6-14}$ aryl group $C_{1-4}$, alkoxy group, $C_{7-14}$ aralkyl group, $C_{1-4}$ alkyl, $C_{6-14}$ aryl group, $C_{1-4}$ alkoxy, $C_{6-14}$ aryl group, or $C_{6-14}$ aryl $C_{1-4}$ alkyl group. Multiple substitutions may be dependently or independently selected from the group consisting of: $C_{1-4}$ alkyl group, $C_{6-14}$ aryl group $C_{1-4}$, alkoxy group, $C_{7-14}$ aralkyl group, $C_{1-4}$ alkyl, $C_{6-14}$ aryl group, $C_{1-4}$ alkoxy, $C_{6-14}$ aryl group, or $C_{6-14}$ aryl $C_{1-4}$ alkyl group.

18. The method according to any one of B embodiments 1-17, wherein the oxazaphospholidine phosphoramidite monomer is a compound of

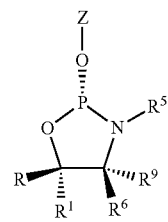

Formula 1a

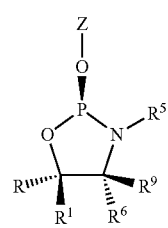

Formula 1b wherein Z, R, $R^1$, $R^6$, $R^9$ and $R^5$ are all as according to B embodiment 17.

19. The method according to B embodiment 17 or 18, wherein R is selected from the group consisting of aryl, heteroaryl, substituted aryl and substituted heteroaryl.

20. The method according to any one of B embodiments 17-19, wherein R is aryl, such as phenyl.

21. The method according to any one of B embodiments 17-20, wherein $R^1$ is hydrogen.

22. The method according to any one of B embodiments 17-21, wherein $R^1$ is $C_{1-3}$ alkyl, such as methyl.

23. The method according to any one of B embodiments 17-22, wherein $R^5$ and $R^6$ together form a heterocyclic ring comprising 3-16 (e.g. 4) carbon atoms, together with the N atom of formula (I), (Ia) or (1b).

24. The method according to any one of B embodiments 17-22, wherein $R^5$ and $R^6$ together form a heterocyclic ring comprising 4 carbon atoms, together with the N atom of formula (I), (Ia) or (1b).

25. The method according to any one of B embodiments 1-24 wherein, the phosphoramidite monomer compound is of formula 2a or 2b

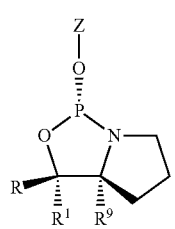

Formula 2a

-continued

Formula 2b

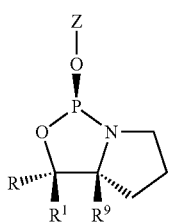

wherein Z, R, and $R^1$ are as according to any one of B embodiments 17-24.

26. The method according to any one of B embodiments 1-25, wherein the oxazaphospholidine phosphoramidite monomer compound is of formula 3a or 3b Formula 3a

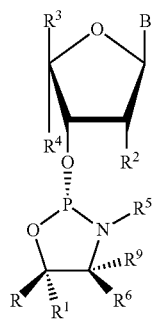

Formula 3b

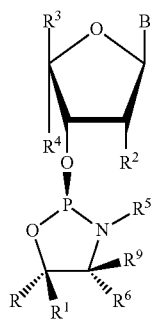

wherein,

R, $R^1$, $R^5$, $R^6$ and $R^9$ are as according to any one of B embodiments 2-18;

B is the a nucleobase group;

$R^3$= is selected from the group consisting of CH$_2$ODMTr, CH$_2$-Alkyl-O-DMTr, CH-Me-O-DMTr, CH$_2$OMMTr, CH$_2$-Alkyl-O-MMTr, CH(Me)-O-MMTr, CH—$R^a$—O-DMTrR$^b$, and CH—$R^a$—O-MMTrR$^b$; $R^2$ is selected from the groups consisting of halo, such as —F, amino, azido, —SH, —CN, —OCN, —CF$_3$, —OCF$_3$, —O($R_m$)-alkyl, —S($R_m$)-alkyl, —N($R_m$)-alkyl, —O($R_m$)-alkenyl, —S($R_m$)-alkenyl, —N($R_m$)-alkenyl; —O($R_m$)-alkynyl, —S($R_m$)-alkynyl or —N($R_m$)-alkynyl; O-alkylenyl-O-alkyl, alkynyl, alkaryl, aralkyl, O-alkaryl, O-aralkyl, O(CH$_2$)$_2$SCH$_3$, O—(CH$_2$)$_2$—O—N($R_m$)($R_n$) or O—CH$_2$C(=O)—N($R_m$)($R_n$), —O—(CH$_2$)$_2$OCH$_3$, and —O—CH$_3$, where each $R_m$ and $R_n$ are independently, H, an amino protecting group or substituted or unsubstituted C$_{1-10}$ alkyl;

$R^4$= is selected from the group consisting of alkyl, cyclo-alkyl, cyclo-heteroalkyl, O-alkyl, S-alkyl, NH-alkyl, and hydrogen;

or $R^2$ and $R^4$ together designate a bivalent bridge consisting of 1, 2, 3 groups/atoms selected from the group consisting of —C($R^aR^b$)—, —C($R^a$)=C($R^b$), —C($R^a$)=N, O, —Si($R^a$)$_2$—, S—, —SO$_2$—, —N($R^a$)—, and >C=Z;

wherein $R^a$ and, when present $R^b$, each is independently selected from hydrogen, optionally substituted C$_{1-6}$-alkyl, optionally substituted C$_{2-6}$-alkenyl, optionally substituted C$_{2-6}$-alkynyl, hydroxy, optionally substituted C$_{1-6}$-alkoxy, C$_{2-6}$-alkoxyalkyl, C$_{2-6}$-alkenyloxy, carboxy, C$_{1-6}$-alkoxycarbonyl, C$_{1-6}$-alkylcarbonyl, formyl, aryl, aryl-ioxy-carbonyl, aryloxy, arylcarbonyl, heteroaryl, hetero-aryloxy-carbonyl, heteroaryloxy, heteroarylcarbonyl, amino, mono- and di(C$_{1-6}$-alkyl)amino, carbamoyl, mono- and di(C$_{1-6}$-alkyl)-amino-carbonyl, amino-C$_{1-6}$-alkyl-aminocarbonyl, mono- and di(C$_{1-6}$-alkyl)amino-O$_{1-6}$-alkyl-aminocarbonyl, C$_{1-6}$-alkyl-carbonylamino, carbamido, C$_{1-6}$-alkanoyloxy, sulphono, C$_{1-6}$-alkylsulphonyloxy, nitro, azido, sulphanyl, C$_{1-6}$-alkylthio, halogen, where aryl and heteroaryl may be optionally substituted and where two geminal substituents Ra and Rb together may designate optionally substituted methylene (=CH$_2$), wherein for all chiral centers, asymmetric groups may be found in either R or S orientation.

27. The method according to any one of B embodiments 1-26, wherein the oxazaphospholidine phosphoramidite monomer is selected from the group consisting of formula 4a, 4b, 5a, 5b, 6a, 6b, 7a and 7b.

Formula 4a

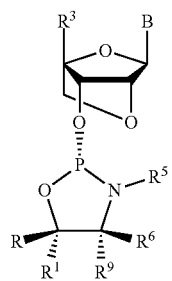

Formula 4b

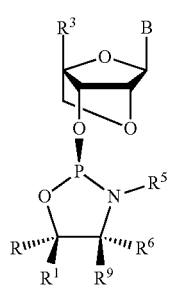

Formula 5a

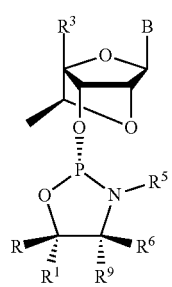

-continued

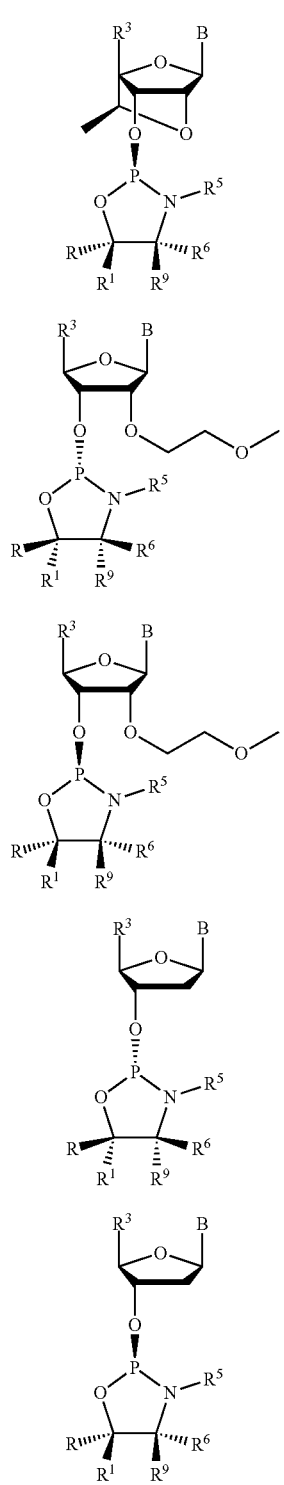

Formula 5b

Formula 6a

Formula 6b

Formula 7a

Formula 7b wherein R, $R^1$, $R^3$, $R^9$, $R^5$, $R^6$ and B are as according to B embodiment 26.

28. The method according to any one of B embodiments 1-27, wherein the oxazaphospholidine phosphoramidite monomer comprises a nucleobase moiety is a purine or a pyrimidine, such as a nucleobase selected from the group consisting of adenine, guanine, uracil, thymine and cytosine, isocytosine, pseudoisocytosine, 5-methyl cytosine, 5-thiozolo-cytosine, 5-propynyl-cytosine, 5-propynyl-uracil, 5-bromouracil 5-thiazolo-uracil, 2-thio-uracil, 2'thio-thymine, inosine, diaminopurine, 6-aminopurine, 2-aminopurine, 2,6-diaminopurine and 2-chloro-6-aminopurine.

29. The method according to any one of B embodiments 1-28, wherein the oxazaphospholidine phosphoramidite monomer is selected from the group consisting of M1-M40.

30. The method according to any one of B embodiments 1-29, wherein the base moiety (B) in the oxazaphospholidine phosphoramidite monomer comprises an adenine base.

31. The method according to any one of B embodiments 1-30, wherein the base moiety (B) in the oxazaphospholidine phosphoramidite monomer comprises a thymine base.

32. The method according to any one of B embodiments 1-30, wherein the base moiety (B) in the oxazaphospholidine phosphoramidite monomer comprises a guanine base.

33. The method according to any one of B embodiments 1-30, wherein the base moiety (B) in the oxazaphospholidine phosphoramidite monomer comprises a cytosine base.

34. The method according to any one B embodiments 1-28, wherein the oxazaphospholidine phosphoramidite monomer is a L monomer.

35. The method according to any one B embodiments 1-33, wherein the oxazaphospholidine phosphoramidite monomer is a D monomer.

36. The method according to any one of B embodiments 1-35, wherein the oxazaphospholidine phosphoramidite monomer is an LNA monomer, such as a beta-D-oxy LNA monomer.

37. The method according to any one of B embodiments 1-36, wherein the oxazaphospholidine phosphoramidite monomer is a DNA monomer.

38. The method according to any one of B embodiments 1-28, wherein the oxazaphospholidine phosphoramidite monomer is selected from the group consisting of formula 8a or formula 8b Formula 8a

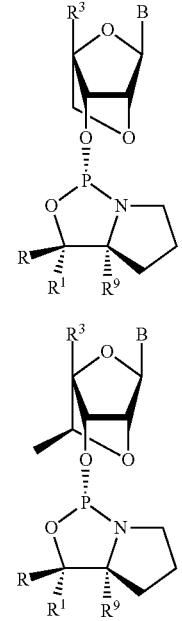

Formula 8b wherein B is thymine, and wherein R, $R^1$, $R^3$ and $R^9$ are as according to any one of B embodiments 17-24.

39. The method according to any one of B embodiments 1-28, wherein the oxazaphospholidine phosphoramidite monomer is selected from the group consisting of formula 8a or formula 8b

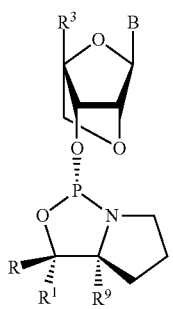

Formula 8a

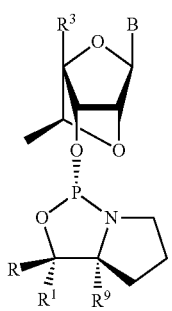

Formula 8b wherein B is adenine, and wherein R, $R^1$, $R^3$ and $R^9$ are as according to any one of B embodiments 17-24, wherein the adenine it may optionally be protected, e.g. with benzoyl).

40. The method according to any one of B embodiments 1-28, wherein the oxazaphospholidine phosphoramidite monomer is selected from the group consisting of a D-DNA-A or a L-DNA-A monomer, such as a oxazaphospholidine phosphoramidite monomer of formula

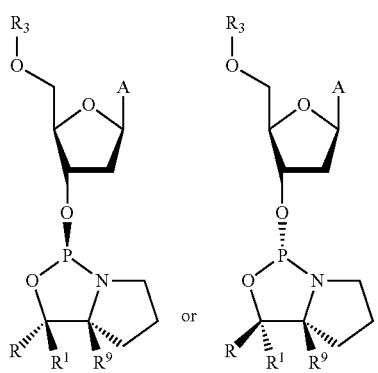

wherein A is adenine, and wherein R, $R^1$, $R^3$ and $R^9$ are as according to any one of B embodiments 1-24, wherein the base adenine may be protected, e.g. with benzoyl.

41. The method according to any one of B embodiments 1-28, wherein the oxazaphospholidine phosphoramidite monomer is selected from the group consisting of a D-DNA-T or a L-DNA-T monomer, such as a oxazaphospholidine phosphoramidite monomer of formula

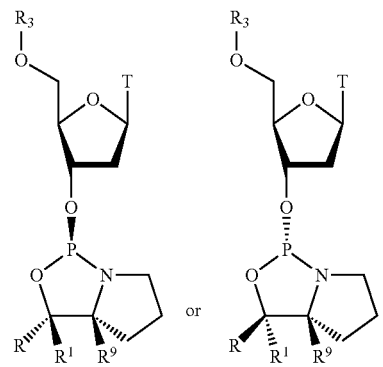

wherein T is thymine, and wherein R, $R^1$, $R^3$ and $R^9$ are as according to any one of B embodiments 1-24.

42. The method according to any one of B embodiments 1-28, wherein the oxazaphospholidine phosphoramidite monomer is selected from the group consisting of a D-DNA-C or a L-DNA-C monomer, such as a oxazaphospholidine phosphoramidite monomer of formula

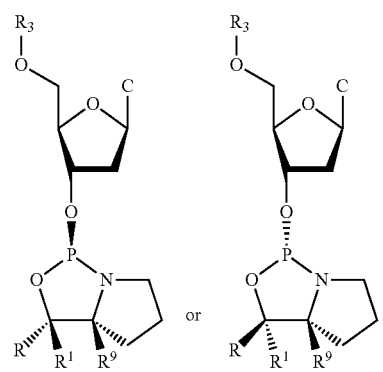

wherein C is cytosine, and wherein R, $R^1$, $R^3$ and $R^9$ are as according to any one of B embodiments 1-24, and wherein the base cytosine may be protected, e.g. with acetyl or benzoyl, and wherein optionally cytosine is 5-methyl cytosine.

43. The method according to any one of B embodiments 1-28, wherein the oxazaphospholidine phosphoramidite monomer is selected from the group consisting of a D-DNA-G or a L-DNA-G monomer, such as a oxazaphospholidine phosphoramidite monomer of formula

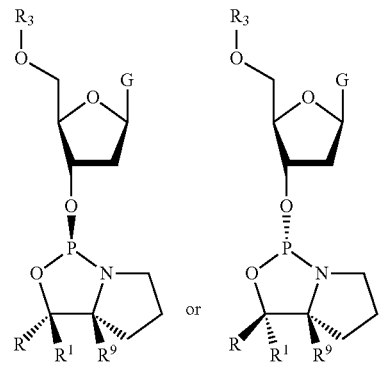

wherein G is guanine, and wherein R, $R^1$, $R^3$ and $R^9$ are as according to any one of B embodiments 1-24, and wherein the base guanine may be protected, e.g. with DMF or acyl such as iBu.

44. The method according to any one of B embodiments 1-28, wherein the oxazaphospholidine phosphoramidite monomer is selected from the group consisting of a D-LNA-A or a L-LNA-A monomer, such as a oxazaphospholidine phosphoramidite monomer of formula

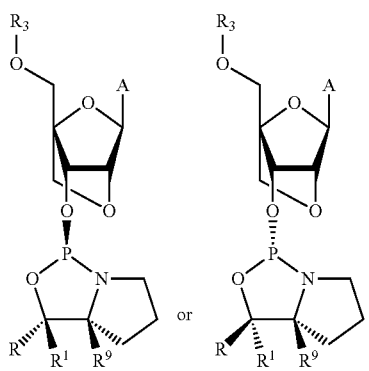

wherein A is adenine, and wherein R, $R^1$, $R^3$ and $R^9$ are as according to any one of B embodiments 1-24, wherein the base adenine may be protected, e.g. with benzoyl.

45. The method according to any one of B embodiments 1-28, wherein the oxazaphospholidine phosphoramidite monomer is selected from the group consisting of a D-LNA-T or a L-LNA-T monomer, such as a oxazaphospholidine phosphoramidite monomer of formula

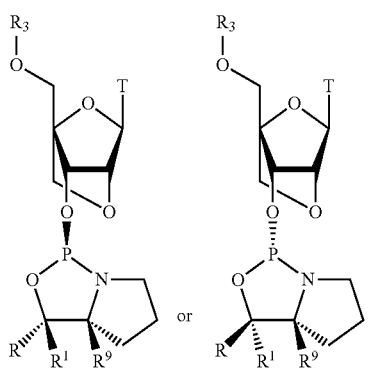

wherein T is thymine, and wherein R, $R^1$, $R^3$ and $R^9$ are as according to any one of B embodiments 1-24.

46. The method according to any one of B embodiments 1-28, wherein the oxazaphospholidine phosphoramidite monomer is selected from the group consisting of a D-LNA-C or a L-LNA-C monomer, such as a oxazaphospholidine phosphoramidite monomer of formula

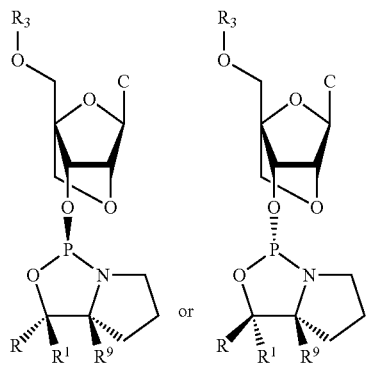

wherein C is cytosine, and wherein R, $R^1$, $R^3$ and $R^9$ are as according to any one of B embodiments 1-24, and wherein the base cytosine may be protected, e.g. with benzoyl or acetyl, and wherein optionally cytosine is 5-methyl cytosine.

47. The method according to any one of B embodiments 1-28, wherein the oxazaphospholidine phosphoramidite monomer is selected from the group consisting of a D-LNA-G or a L-LNA-G monomer, such as a oxazaphospholidine phosphoramidite monomer of formula

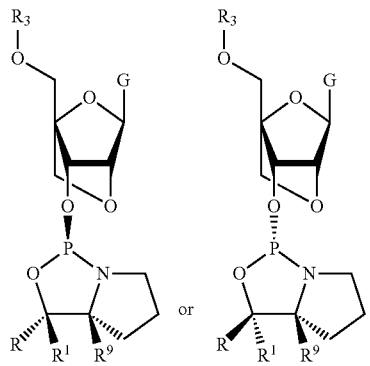

wherein G is guanine, and wherein R, $R^1$, $R^3$ and $R^9$ are as according to any one of B embodiments 1-24, and wherein the base guanine is protected with acyl such as iBu for the L-LNA-G monomer, or either acyl (such as iBu) or DMF for the D-LNA-G monomer.

48. The method according to any one of B embodiments 1-47 wherein the oxazaphospholidine phosphoramidite monomer is a DNA monomer, or is a LNA monomer selected from the group consisting of a LNA-A monomer, a LNA-C monomer and an acyl protected L-LNA-G monomer.

49. The method according to any one of B embodiments 1-47 wherein the oxazaphospholidine phosphoramidite monomer is other than a LNA-T monomer, a D-LNA-G monomer, or a DMF protected L-LNA-G monomer.

50. The method according to any one of B embodiments 17-49, wherein R is phenyl, $R^1$ is hydrogen or methyl, $R^9$ is hydrogen, and $R^3$ is selected from the group consisting of $CH_2ODMTr$, $CH_2$-Alkyl-O-DMTr, CH-Me-O-DMTr, $CH_2OMMTr$, $CH_2$-Alkyl-O-MMTr, CH(Me)-O-MMTr, CH—$R^a$—O-DMTr$R^b$, and CH—$R^a$—O-MMTr$R^b$, such as $CH_2$—O-DMTr or $CH_2$—O-MMTr.

51. The method according to any one of B embodiments 17-49, wherein R is phenyl, $R^1$ is hydrogen or methyl, $R^9$ is hydrogen, and $R^3$ is —$CH_2$—O-DMTr.

52. An acetonitrile solution comprising the oxazaphospholidine phosphoramidite monomer according to any one of B embodiments 17-51, acetonitrile and an aromatic heterocyclic solvent.

53. The acetonitrile solution according to B embodiment 52, wherein the concentration of the oxazaphospholidine phosphoramidite monomer is between about 0.05 M and about 2 M, such as about 0.1 M to about 1M, such as about 0.1M-about 0.2M, such as about 0.15 M, or about 0.175 M, or about 0.2 M.

54. The acetonitrile solution according to B embodiment 52 or 53, wherein the aromatic heterocyclic solvent is as according to any one of B embodiments 1-16.

55. The acetonitrile solution according to any one of B embodiments 52-54, wherein the concentration of aromatic heterocyclic solvent in acetonitrile is between about 0.1% and about 50% (v/v), such as between about 0.5% and about 25% (v/v).

56. The acetonitrile solution according to any one of B embodiments 52-55, wherein the concentration of aromatic heterocyclic solvent in acetonitrile is between about 0.5% and about 10%, such as between about 1% and about 5% (v/v), such as between about 2-4%, such as about 2.5%, such as about 3.5%.

EXAMPLES

Example 1

General Synthesis Method

To a solution of N-methylmorpholine in toluene (50 mL) $PCl_3$ (2.93 mL 33.4 mmol) was added at −70° C. over a time course of 10 min. Hereafter, proline (P5-D or P5-L) auxillary (6.24 g 35.2 mmol) in toluene (50 mL) was added over 30 min (see *J. Am. Chem. Soc.*, 2008, 130, 16031-16037 for synthesis of P5-D and P5-L). The resulting mixture was stirred at room temperature for 1.5 h after which solvent and volatiles were removed in vacuo (40° C. and 15 mbar). Then, the remaining residue was dissolved in THF (50 mL) and hereafter cooled to −70° C. followed by the addition of first NEt3 (17.8 mL 128 mmol) and then, over 30 min, 5'-ODMT-DNA-Nucleoside (16 mmol) as a solution in THF (50 mL). The reaction mixture was stirred at −77° C. for 30 min and then for 2 h at room temperature. Hereafter, cold EtOAc (200 mL) was added and mixture was washed with cold NaHCO3 (150 mL), brine (150 mL), dried (Na2SO4), filtered, and evaporated to dryness. The crude product was purified by flash column chromatography under argon with 7% NEt3 included in the eluent to avoid degradation on silica.

The product was obtained as a solid potentially containing small amounts of residual solvents from e.g. EtOAc, THF, and NEt3.

Using the above procedure, the following monomers were synthesized:

D-DNA A: 31P NMR (160 MHz, DMSO-d6): δ 150.3
L-DNA A: 31P NMR (160 MHz, DMSO-d6): δ 148.5
D-DNA T: 31P NMR (160 MHz, DMSO-d6): δ 151.0
L-DNA T: 31P NMR (160 MHz, DMSO-d6): δ 149.1
D-DNA C: 31P NMR (160 MHz, DMSO-d6): δ 151.7
L-DNA C: 31P NMR (160 MHz, DMSO-d6): δ 149.8
D-DNA G-i-Bu: 31P NMR (160 MHz, DMSO-d6): δ 151.7
L-DNA G-DMF: 31P NMR (160 MHz, DMSO-d6): δ 150.3

Example 2

Synthesis of D-LNA-G-DMF

5'-ODMT-LNA-G (3.51 g 5.00 mmol) was co-evaporated with pyridine and then with toluene to remove any residual water or other solvents. Then the residue was dissolved in pyridine (10 mL) and THF (10 mL). This solution was added to solution of D-oxazapholidine (3.51 g 5.00 mmol), $PCl_3$ (0.88 mL 10.0 mmol), and NEt3 (3.50 mL 25.0 mmol) at −77° C. The resulting reaction mixture was then stirred at −77° C. for 15 min and then at 1.5 h at room temperature. Hereafter, EtOAc (150 mL) was added and mixture was washed with cold NaHCO3 (100 mL) and brine (100 mL), dried using Na2SO4, filtered, and finally evaporated together with toluene.

The resulting residue was purified by column chromatography (eluent THF in EtOAc form 10% to 30%+7% NEt3) giving D-LNA-G-DMF (3.91 g, estimated yield 84%).

1H NMR (400 MHz, DMSO-d6): δ 11.42 (1H, s), 8.56 (1H, s), 7.95 (1H, s), 7.49-7.16 (14H, m), 6.90-6.83 (4H, m), 5.96 (1H, s), 5.58 (1H, d, J=6.7 Hz), 3.87 (1H, d, J=8.1 Hz), 3.72 (6H, s), 3.62-3.54 (1H, m), 3.45 (2H, s), 3.40-3.33 (1H, m), 3.08 (3H, s), 2.99 (3H, s), 2.93-2.84 (1H, m), 1.53-1.39 (2H, m), 1.06-0.97 (1H, m), 0.79-0.63 (1H, m).

31P NMR (160 MHz, DMSO-d6): δ 151.6
LRMS (ESI) m/z [M+H]+ calcd for $C_{46}H_{49}N_7O_8P$: 858.3. Found: 858.7.

Example 3

Synthesis of L-LNA-G-DMF

5'-ODMT-LNA-G-DMF (4.91 g 7.00 mmol) was co-evaporated with pyridine and then with toluene to remove any residual water or other solvents. Then the residue was dissolved in pyridine (10 mL) and THF (15 mL). This solution was added to solution of L-oxazapholidine (2.48 g 14.0 mmol), $PCl_3$ (1.22 mL 14.0 mmol), and NEt3 (4.90 mL 35.0 mmol) at −77° C. The resulting reaction mixture was then stirred at −77° C. for 15 min and then at 1.5 h at room temperature. Hereafter, EtOAc (150 mL) was added and mixture was washed with cold NaHCO3 (100 mL) and brine (100 mL), dried using Na2SO4 filtered, and finally evaporated together with toluene.

The resulting residue was purified by column chromatography (eluent THF in EtOAc/DCM 1:1 using a gradient from 15% to 25%+7% NEt3) giving D-LNA-G-DMF (3.41 g, estimated yield 84%). The product was purified by column chromatography as described above.

1H NMR (400 MHz, DMSO-d6): δ 12.3-11.9 (1H, br s), 11.8-11.5 (1H, br s), 8.05 (1H, s), 7.45-7.40 (2H, m), 7.35-7.21 (10H, m), 7.02-6.97 (2H, m), 6.92-6.86 (4H, m), 5.94 (1H, s), 5.09 (1H, d, J=6.5 Hz), 4.88 (1H, d, J=7.5 Hz), 4.69 (1H, s), 3.89-3.81 (2H, m), 3.74 (3H, s), 3.73 (3H, s), 3.71-3.64 (1H, m), 3.48-3.38 (3H, m), 2.83-2.73 (1H, m), 2.71-2.64 (1H, m), 1.55-1.45 (2H, m), 1.14-1.05 (1H, m), 1.08 (3H, d, J=6.9 Hz), 1.05 (3H, d, J=6.9 Hz), 0.76-0.66 (1H, m).

31P NMR (160 MHz, DMSO-d6): δ 148.7
LRMS (ESI) m/z [M+H]+ calcd for $C_{47}H_{50}N_6O_9P$: 873.3. Found: 873.7.

Example 4

Synthesis of D-DNA G-DMF

To a solution of N-methylmorpholine in toluene (50 mL) was $PCl_3$ (2.93 mL 33.4 mmol) added at −70° C. over a time course of 10 min. Hereafter P5-D (6.24 g 35.2 mmol) in toluene (50 mL) was added over 30 min. The resulting reaction mixture was stirred at room temperature for 1.5 h after which solvent and volatiles were removed in vacuo (40° C. and 15 mbar). Then, the remaining residue was dissolved in THF (50 mL) and hereafter cooled to −70° C. followed by the addition of first NEt₃ (17.8 mL 128 mmol) and then, over 30 min, 5'-ODMT-DNA-G-DMF (9.99 g 16.0 mmol) as a solution in THF (50 mL). The reaction mixture was stirred at −77° C. for 30 min and then for 2 h at room temperature. Hereafter, cold EtOAc (200 mL) was added and mixture was washed with cold NaHCO₃ (150 mL), brine (150 mL), dried (Na₂SO₄), filtered, and evaporated to dryness. The crude product was purified by flash column chromatography under argon (eluent DCM/EtOAc=2/1+7% NEt₃). D-DNA-G-DMF was isolated as a white foam (10.6 g, 72%) with traces of solvent impurities (EtOAc, toluene, and NEt₃).

¹H NMR (400 MHz, DMSO-d₆): δ 11.36 (1H, s), 8.52 (1H, s), 7.96 (1H, s), 7.40-7.16 (14H, m), 6.83-6.77 (4H, m), 6.27 (1H, t, J=6.4 Hz), 5.65 (1H, d, j=6.5 Hz), 5.08-5.01 (1H, m), 4.02-3.98 (1H, m), 3.91-3.83 (1H, m), 3.71 (6H, s), 3.45-3.35 (1H, m), 3.27-3.18 (2H, m), 3.07 (3H, s), 3.00 (3H, s), 2.97-2.88 (2H, m), 2.49-2.40 (1H, m), 1.58-1.48 (1H, m), 1.47-1.38 (1H, m), 1.16-1.09 (1H, m), 0.86-0.76 (1H, m).

³¹P NMR (160 MHz, DMSO-d₆): δ 151.7

LRMS (ESI) m/z [M−H]⁻ calcd for C₄₆H₄₇N₇O₇P: 828.3. Found: 828.6.

Example 5

Synthesis of L-DNA G-DMF

To solution of N-metylmorpholine in toluene (25 mL) was PCl3 (1.33 mL 15.2 mmol) during 5 minutes added at −55° C. followed with the addition of P5-L (2.84 g 16.00 mmol) in toluene (25 mL) during 15 min. The resulting reaction mixture was stirred at −55-45° C. for 10 min and then at 1.5 h at room temperature. Then, the solvent and other volatiles were removed in vacuo (40° C. and 6 mbar). The remaining residue was then dissolved in THF (25 mL) and cooled to −77° C. Hereafter, NEt3 (8.92 mL 64 mmol) was added followed by a solution of 5'-ODMT-DNA-G-DMF (4.5 g, 7.2 mmol) in THF (25 mL) during 15 min. The reaction mixture was stirred at −77° C. for 15 min and then at 3 h at room temperature. Hereafter, EtOAc (150 mL) was added and the mixture was extracted with cold NaHCO3 (100 mL), brine (50 mL), dried (Na2SO4), filtered, and evaporated.

The product was isolated by flash column chromatography under argon (eluent EtOAc/DCM=1/2+7% NEt3) as a white foam (3.77 g, 63%) together with traces of EtOAc.

¹H NMR (400 MHz, DMSO-d₆): δ 11.36 (1H, s), 8.51 (1H, s), 7.96 (1H, s), 7.39-7.11 (14H, m), 6.80-6.73 (4H, m), 6.28 (1H, t, J=6.5 Hz), 5.72 (1H, d, j=6.5 Hz), 5.06-4.96 (1H, m), 4.02-3.95 (1H, m), 3.84-3.76 (1H, m), 3.70 (3H, s), 3.69 (3H, s), 3.50-3.39 (1H, m), 3.27-3.18 (2H, m), 3.08 (3H, s), 3.02 (3H, s), 2.98-2.83 (2H, m), 2.48-2.39 (1H, m), 1.58-1.40 (2H, m), 1.12-1.02 (1H, m), 0.83-0.71 (1H, m).

³¹P NMR (160 MHz, DMSO-d₆): δ 150.3

LRMS (ESI) m/z [M+H]⁺ calcd for C₄₅H₄₉N₇O₇P: 830.3. Found: 830.6.

Example 6

Synthesis of L-LNA-G-Ibu Monomers

Procedure for the Synthesis of 5'-OAP-LNA-G-iBu Derivatives

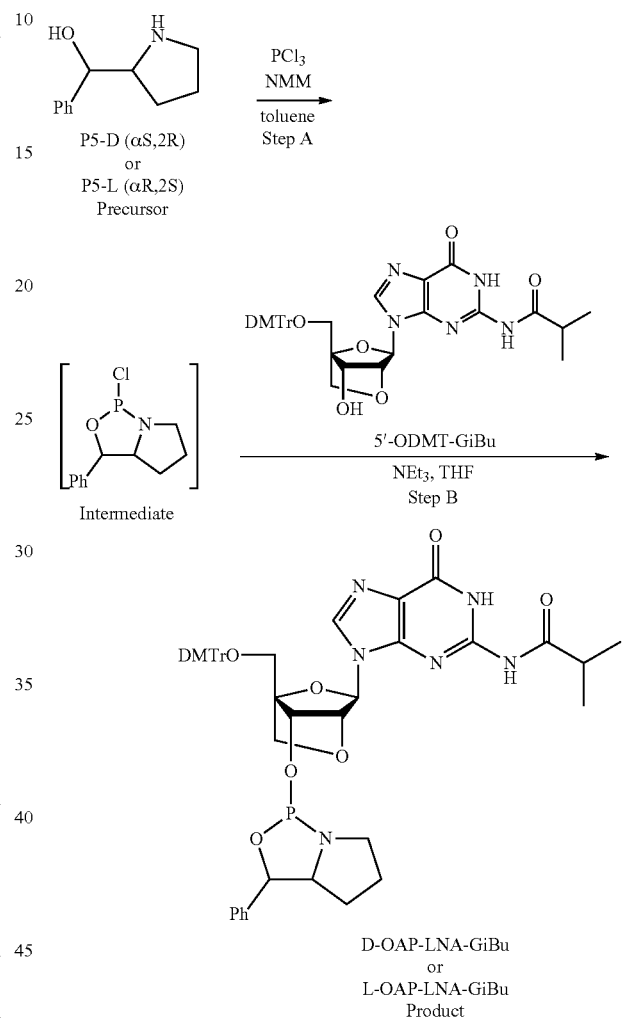

Step A: To a solution of N-methylmorpholine (1.76 mL 16.0 mmol) in toluene (15 mL) was added PCl₃ (0.66 mL 7.6 mmol) over 5 min at −55° C. Hereafter, a solution of (S)-phenyl-(R)-pyrolidin-2yl)methanol (P5-D) (1.42 g 8.00 mmol) in toluene (12 mL) was added during the next 15 min. Then, the reaction mixture was stirred for 10 min between −55 to −45° C. and then at room temperature for 1.5 h.

Solvents and other volatile compounds were removed in vacuo at 40° C. and 6 mbar after which THF (13 mL) was added.

Step B: This was followed by a cooling of the reaction mixture to −77° C. whereafter triethylamine (5.54 mL, 40 mmol) was added followed by a solution of 5'-ODMT-LNA-G-iBu (2.67 g, 4 mmol) in THF (13 mL) over 15 min. The resulting mixture was stirred for 15 min at −77° C. and then at room temperature for 3 h. Hereafter, EtOAc (75 mL) was added and the mixture was washed with cold NaHCO₃ (50 mL) and brine (50 mL), dried using Na₂SO₄, filtered, and evaporated in vacuo. The crude product was purified by flash column chromatography under Ar (EtOAc:hexane, 1:4+7% NEt₃).

The product was obtained as a white foam (1.95 g, estimated yield of 55%).

$^{31}$P-NMR in DMSO 148.8 ppm+1% at 28.8 ppm.

Additional optimization of the synthesis for both D-LNA G-iBu and L-LNA G-iBu

| No. | St. m. | molar ratio P5:PCl₃:5'-ODMT-LNA-G-iBu | 5'-ODMT-LNA-G-iBu, mmol | Estimated yield,$^a$ % |
|---|---|---|---|---|
| 1 | P5-L | 2:2:1 | 8.00 | 48 |
| 2 | P5-L | 2:1.9:1 | 4.00 | 55 |
| 3 | P5-D | 2.2:2.1:1 | 7.20 | 64 |
| 4 | P5-L | 2.4:2.4:1 | 8.00 | 64 |
| 5 | P5-L | 2.2:2.1:1 | 8.00 | 68 |

It was found that a slight excess of PCl₃ over the precursor (e.g. P5) causes formation of side products that significantly reduce the yield of the product (e.g. OAP-LNA-GiBu). It is therefore desirable to use at least molar equivalents of precursor & PCl₃. In some embodiments the molar ratio of precursor to PCl₃ in step 1 is, greater than about 1, such as 1.05 of above. In some embodiments the molar ratio of precursor to PCl₃ in step 1 is no greater than 1.5.

It was found that the use of over two fold molar equivalents of the intermediate in step 2 gave the highest yield of product (see table, entries 3 and 5). In some embodiments the molar ratio of intermediate (e.g. 5'-ODMT-G/iBu) to the precursor and PCl₃ is greater than 2.

The purity of the products was determined from $^{31}$P-NMR spectra.

Example 7

Determination of Stability and Solubility of Products

To investigate the stability and solubility of L-LNA G-DMF and L-LNA G-i-Bu the following experimental procedure was followed:

To a 1.5 mL vial was added 0.013 mmol of amidite after which the solid material was dissolved in 0.13 mL of solvent. Hereafter, the vial was capped, vortexed, and finally left at room temperature for 24 hours. Then, the dissolved material was visually examined regarding the solubility (FIG. 1). If the solution appeared cloudy or otherwise non-homogenous the solubility was set to "no". If the solution appeared completely homogenous the solubility was set to "yes" (examination repeated after 24 hours).

Stability Determination Method: To complete the analysis the stability of the amidite was investigated using an Agilent 1100 series HPLC-MS with a gradient from 80% A (1% NH4OH in H2O) to 100% B (20% A in MeCN) and a Waters Xterra MS C18 2.1×100 mm column. The mass and UV peak of the mother compound was identified at 0 hours and at 24 hours. Hereafter, the relative stability compared to other by-products was reported by integrating the UV chromatogram (254 nm) and normalizing the area to the chromatogram recorded at 0 hours (FIG. 2).

Figure 3B:
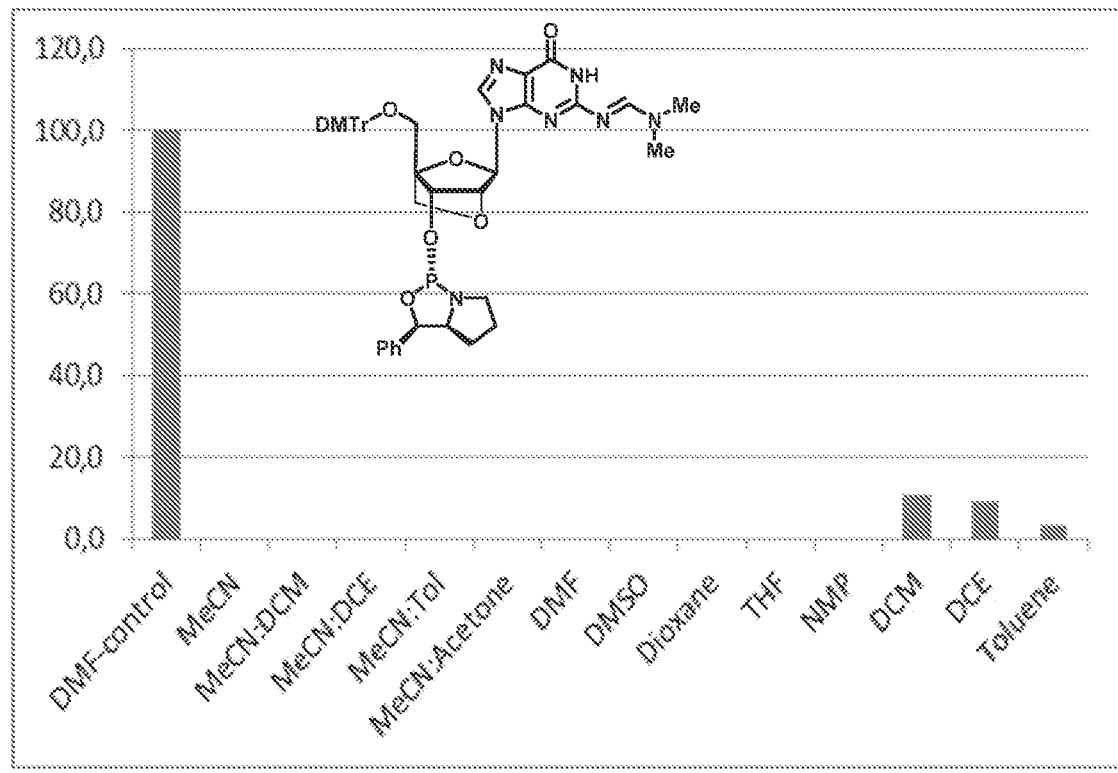

The solubility data at 0 hours and 24 hours after synthesis for the three monomers is illustrated in FIG. 1. The stability data measured after 24 hours in various solvents is shown in FIG. 2 and FIGS. 3a (L-LNA-G-iBu) and 3b (L-LNA-G-DMF).

The monomer L-LNA G-DMF is unsoluble in most solvents (MeCN, MeCN:DCE, MeCN:Tol, MeCN:acetone, Dioxane, and THF). The solvents where the monomer is soluble (MeCN:DCM, DMF, DMSO, NMP, DCM, DCE, and Toluene) shows a tremendous instability. The best solvent being DCM with 10% left of the amidite after 24 hours.

The monomer L-LNA G-i-Bu is soluble in all solvents investigated (12 different) with the best performing being MeCN, MeCN:acetone, DCM, and DCE. All solvents investigated for the L-LNA G-i-Bu monomer shows a significant improvement in solubility and stability.

Example 8

Relative Coupling Efficiency in Model System

Model System: 5'-Gcattggtatt(LNA A)Cattgttgtttt-3'

In order to retard the coupling efficiency of a conventional LNA phosphoroamidite the LNA A was diluted to 0.025 M in MeCN (with and without 5% pyridine). Hereafter the amidite was used in the model system (5'-gcattggtatt(LNA A)cattgttgtttt-3'). Here the 3' flank was identified in the crude mixture after deprotection and compared to the full length product in order to obtain a relative coupling efficiency for the monomer in question, i.e. LNA A 0.025 M and LNA A 0.025 M+5% pyridine.

The results show that the coupling is indeed restarted by reducing the concentration of the monomer in solution. However, it also shows that in the case of LNA A there is a decrease in reactivity with the addition of pyridine (FIG. 4).

Example 9

Triethylamine Stabilisation of Oxazaphospholidine Phosphoramidite Monomer Solutions, but does not Improve Coupling Efficacy Here the stability of L-LNA A in the presence of Et₃N (5-10 eq as compared to amidite) was monitored.

To investigate the stability and solubility of L-LNA A the following experimental procedure was followed.

To a 1.5 mL vial was added 0.013 mmol of amidite after which the solid material was dissolved in 0.13 mL of solvent (with and without Et3N, approximately 5-10 eq). Hereafter, the vial was capped, vortexed, and finally left at room temperature for 24 hours. To investigate the stability of the amidite an Agilent 1100 series HPLC-MS with a gradient from 80% A (1% NH4OH in H2O) to 100% B (20% A in MeCN) and a Waters Xterra MS C18 2.1×100 mm column was used. The mass and UV peak of the mother compound was identified at 0 hours and at 24 hours. Hereafter, the relative stability compared to other by-products was reported. This was again repeated after 48 hours.

The results (FIG. 5) show that the stability of L-LNA A, only in the presence of MeCN, is very unstable over time. After 24 hours most of the L-LNA A was degraded. After 48 hours the L-LNA A monomer was completely degraded. In the case of L-LNA A in MeCN and in the presence of Et3N (approximately 5-10 eq as compared to the monomer) the L-LNA A is completely stable after 24 hours. After 48 hours L-LNA A is partly, however still the majority of the L-LNA A is preserved in the solution.

Thus, the Et3N stabilizes the amidite in solution. However, using these conditions in the oligonucleotide synthesis only results in trace amounts full length product.

Example 10

Relative Coupling Efficiency in the Model System Using L-LNA A Oxazaphospholidine Phosphoramidite Monomers and a Variety of Different Amine Bases In order to find a suitable base which is tolerated in the coupling step several different additives in the concerning nitrogen containing bases were investigated in the model system (5'-gcattggtatt(LNA A)cattgttgtttt-3').

After global deprotection ($NH_4OH$ at 60° C. overnight) of the oligonucleotide the 3' DNA flank was identified and compared to the full length product in the crude mixture in order to obtain a value for the relative coupling efficiency for the conditions (solvent+/−base) investigated. The results are shown in FIG. 6.

Interestingly, it was found that the conventional oligonucleotide synthesis solvent MeCN in itself resulted in a mediocre relative coupling efficiency of 59%. However, in the presence of pyridine the coupling was possible and in some cases resulted in an improved relative coupling efficiency.

By titrating the amount of pyridine needed to obtain a maximum coupling efficiency it was found that an amount between 5 to 1% v/v pyridine in MeCN was optimal.

Furthermore, also pyridine derivatives such as 3-picoline enhanced the coupling efficiency.

Example 11

Relative Coupling Efficiency in the Model System Using a Variety of Oxazaphospholidine Phosphoramidite Monomers and a Variety of Different Solvents In order to investigate the effect of added pyridine to the solvent of the monomer a set of 5 additional monomers were investigated using the model system (5'-gcattggtatt(stereo-defined amidite)cattgttgtttt-3').

After global deprotection ($NH_4OH$ at 60° C. overnight) of the oligonucleotide the 3' DNA flank was identified and compared to the full length product in the crude mixture in order to obtain a value for the relative coupling efficiency for the conditions (solvent+/−base) investigated. The results are shown in FIG. 7.

It is seen that the effect of increased reactivity, the addition of pyridine, is not general among all monomers. Interestingly, specific monomers, like D-DNA A, benefit from the pyridine in terms of increased relative coupling yield.

In other cases the results are comparable with and with out pyridine, as in the case w. L-DNA A. However, looking at the properties of solubility, MeCN by itself is not sufficient to keep the monomer in solution over a time period of 24 hours. With the addition of 2.5% pyridine the monomer is kept in solution over a time period of 24 hours.

Example 12

Solubility of Various Oxazaphospholidine Phosphoramidite Monomers in MeCN+/−2.5% Pyridine, and Stability of the Solutions Solubility of the following monomers was determined as per example 7.

| Soluble after: | 0 h MeCN + 2.5% pyridine | 24 h MeCN + 2.5% pyridine | 0 h MeCN | 24 h MeCN |
|---|---|---|---|---|
| D-DNA A | Yes | Yes | Yes | No |
| L-DNA A | Yes | Yes | Yes | No |
| D-DNA T | Yes | Yes | Yes | No |
| L-DNA T | Yes | Yes | Yes | No |
| D-DNA C | Yes | Yes | Yes | No |
| L-DNA C | Yes | Yes | Yes | No |
| D-DNA G | Yes | Yes | Yes | No |
| L-DNA G | Yes | Yes | Yes | No |
| D-LNA A | Yes | Yes | Yes | No |
| L-LNA A | Yes | Yes | Yes | No |
| D-LNA T | Yes | Yes | Yes | Yes |
| L-LNA T | Yes | Yes | Yes | Yes |
| D-LNA C | Yes | Yes | Yes | No |
| L-LNA C | Yes | Yes | Yes | No |
| D-LNA G | Yes | Yes | Yes | Yes |
| L-LNA G-DMF | No | No | No | No |
| L-LNA-G-iBu | Yes | Yes | Yes | no |

DNA A is Bz protected, DNA C is acetyl (Ac) protected, DNA T no protecting group, DNA G is DMF, LNA A is Bz protected, LNA C is Bz, LNA T no protecting group, LNA G is DMF (D-LNA) and Ibu (L-LNA).
Bz = benzoyl.

Unless indicated all monomers have DMF protected nucleobases, with the exception of L-LNA-G-iBu, which has an isobutyryl protection group.

Further testing additional monomers reveals that the solubility enhancing effect of the addition of pyridine is general across the series of monomers. As in the case of D-LNA A, D-DNA A and, L-DNA A these monomers are not soluble after 24 hours in MeCN. However with the addition of pyridine the solubility of the monomer is preserved. The enhancement in reactivity is also seen for D-DNA A and L-LNA T while L-DNA A and D-LNA A reacts in a comparable manner.

Example 13

Conversion of Full Length Product with and without 2.5% Pyridine and with Various Activation Concentrations The relative coupling conversions as obtained in the model system 5'-Xttttttttttttttt-3'—with X=L-LNA A. The unreacted fragment (5'-ttttttttttttttt-3') and the full length product (i.e. 5'-(L-LNA-A)ttttttttttttttt-3') is integrated and compared relative to each other in order to obtain the relative coupling efficiency in the system. Different concentrations of activator was used in order to determine the optimal concentrations. The addition of pyridine clearly enhances the coupling efficiency as relative to the couplings whereby no pyridine is present. As can be seen by the results (FIG. 8), irrespective of activator concentration, the addition of pyridine has in general, a benefit in terms of an increased conversion ratio. It is also apparent, as is routine in the art, that the concentration of activator should be optimised, and with regards DCI, it is typically used at a concentration of 1M DCI with 0.1M NMI. Using the obtained conversions to full length product a number of theoretical yields were calculated. Here it is evident that the addition of pyridine is crucial in order to obtain useful yields which can be used for drug discovery. Given the coupling efficacy data obtained experimentally, it is possible the theoretic yields for a 13mer oligonucleotide are shown in FIG. 9, and for a 16mer oligonucleotide see FIG. 10. The data is provided in the table below:

Table of Actual Conversions to Full Length Products Together with the Theoretical Yields of 13 and 16Mers

| Molarity of activator | over all yield 13mer no pyridine | over all yield 16mer no pyridine | over all yield 13mer with pyridine | over all yield 16mer eith pyridine |
|---|---|---|---|---|
| 1.6M DCI + 0.16M NMI | 0.020326 | 0.002858 | 4.668229 | 2.301619 |
| 1.5M DCI + 0.15M NMI | 4.21E−08 | 2.88E−10 | 16.35876 | 10.77229 |
| 1.4M DCI + 0.14M NMI | 0.00718 | 0.000794 | 0.012207 | 0.001526 |
| 1.3M DCI + 0.13M NMI | 0.012207 | 0.001526 | 0.000925 | 6.38E−05 |
| 1.2M DCI + 0.12M NMI | 1.59E−05 | 4.30E−07 | 0.012207 | 0.001526 |
| 1.1M DCI + 0.11M NMI | 1.49E−06 | 2.33E−08 | 0.015791 | 0.002095 |
| 1M DCI + 0.1M NMI | 1.67185 | 0.650378 | 21.98215 | 15.49673 |
| 0.9M DCI + 0.09M NMI | 0.084055 | 0.0164 | 14.07602 | 8.953137 |
| 0.8M DCI + 0.08M NMI | 0.246279 | 0.061581 | 4.298387 | 2.079287 |
| 0.7M DCI + 0.07M NMI | 0.161915 | 0.036752 | 6.461082 | 3.433684 |
| 0.6M DCI + 0.06M NMI | 0.005461 | 0.000567 | 1.165087 | 0.416998 |
| 0.5M DCI + 0.05M NMI | 1.59E−05 | 4.30E−07 | 1.397406 | 0.521579 |
| 0.4M DCI + 0.04M NMI | 0.000171 | 7.96E−06 | 4.668229 | 2.301619 |
| 0.3M DCI + 0.03M NMI | 2.822128 | 1.238846 | 0.200029 | 0.047672 |
| 0.2M DCI + 0.02M NMI | 8.11E−05 | 3.19E−06 | 0.000344 | 1.89E−05 |
| 0.1M DCI + 0.01M NMI | 2.83E−07 | 3.01E−09 | 0.001265 | 9.38E−05 |
| 0.05M DCI + 0.01M NMI | 2.54E−12 | 1.85E−15 | 7.94E−10 | 2.18E−12 |

This data show the marked benefit of using the coupling solvents of the present invention for the synthesis of stereodefined oligonucleotides.

Example 14

Stereodefined Oligonucleotide Synthesis Improvements

In this example, synthesis of stereochemical variants of the LNA oligonucleotide shown below was performed, using the standard conditions (acetonitrile coupling solvent), and according to the invention:

(SEQ ID NO 1)
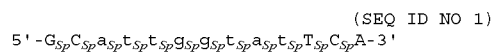
5'-G$_{Sp}$C$_{Sp}$a$_{Sp}$t$_{Sp}$t$_{Sp}$g$_{Sp}$g$_{Sp}$t$_{Sp}$a$_{Sp}$t$_{Sp}$T$_{Sp}$C$_{Sp}$A-3'

X denote LNA nucleotide
Lowercase letter denote DNA nucleotide
Subscript Sp=stereorandom phosphorothioate internucleoside linkage.

Prior art conditions: 49 compounds were synthesized on 1 μmol scale using acetonitrile as the solvent for the stereodefined phosphoramidites, and 0.25M DCI as the activator. By using acetonitrile significant issues in relation to insta-bility and solubility of the phosphoramidites was observed, which caused clogging of the lines on the synthesis instrument and low lifetime of the amidite solutions. All syntheses were carried out DMT-ON, meaning that no final acid treatment is taking place on the synthesis instrument. After the synthesis, the oligonucleotides were cleaved from the solid support using concentrated ammonium hydroxide at room temperature. The oligonucleotides were hereafter deprotected by placing the resultant solutions at 60° C. for 24 h. The oligonucleotides were hereafter purified by using DMTr-based reversed phase cartridge purification. After concentration of the oligonucleotides in vacuo, the oligonucleotides were dissolved in 200 μL PBS, and the concentration was determined by optical absorbance at 260 nm, and backcalculated to a concentration using a theoretically calculated extinction coefficient. The average concentrations of the 49 solutions of oligonucleotides was hereby measured to be 391 μM in 200 μL PBS.

New and improved conditions: 192 compounds were synthesized on 1 μmol scale using 3.5% pyridine in acetonitrile as the solvent for the stereodefined phosphoramidites, and 1M DCI+0.1M NMI as the activator. By using this solvent for the stereodefined amidites, no issues in relation to solubility were observed, and furthermore the lifetime of the amidite solutions was seen to be much longer. All syntheses were carried out DMT-ON, meaning that no final acid treatment is taking place on the synthesis instrument. After the synthesis, the oligonucleotides were cleaved from the solid support using concentrated ammonium hydroxide at room temperature. The oligonucleotides were hereafter deprotected by placing the resultant solutions at 60° C. for 24 h. The oligonucleotides were hereafter purified by using DMTr-based reversed phase cartridge purification. After concentration of the oligonucleotides in vacuo, the oligonucleotides were dissolved in 200 µL PBS, and the concentration was determined by optical absorbance at 260 nm, and backcalculated to a concentration using a theoretically calculated extinction coefficient. The average concentrations of the 192 solutions of oligonucleotides was hereby measured to be 1071 µM in 200 µL PBS Thus comparing the solubility and reactivity enhancements across the series we see a factor of 2.7 enhancement of the yield with pyridine compared to the conditions without pyridine.

Example 15

Relative Coupling Efficiency in the Model System Using a Variety of Oxazaphospholidine Phosphoramidite Monomers in Acetonitrile with and without Pyridine In order to investigate the effect of added pyridine to the solvent of the monomer a set of 7 additional monomers were investigated using the model system (5'-gcattggtatt (stereodefined amidite) cattgttgtttt-3').

After global deprotection (NH$_4$OH at 60° C. overnight) of the oligonucleotide the 3' DNA flank was identified and compared to the full length product in the crude mixture in order to obtain a value for the relative coupling efficiency for the conditions (solvent+/−base) investigated. The results are shown in FIG. 19. The results illustrate that in addition to the benefits of improved solubility and stability for all the monomers, the use of coupling solvents comprising heterocyclic base solvents, such as pyridine, provides a marked improvement in coupling efficacy of D-DNA-C, L-LNA-C and L-LNA-G monomers, in addition to L-LNA-T and D-DNA-A monomers (see FIG. 7). In addition, the results illustrate that the presence of pyridine does not adversely effect the coupling efficacy of other monomers.

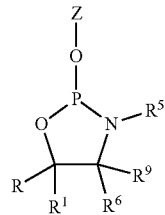

Formula I wherein Z is a nucleoside,
$R^5$ and $R^6$ are independently selected from the group consisting of hydrogen, $C_{1-4}$ alkyl, $C_{3-7}$ cycloalkyl, $C_{6-14}$ aryl, substituted $C_{1-4}$ alkyl, substituted $C_{3-7}$ cycloalkyl, substituted $C_{6-14}$ aryl, or $R^5$ and $R^6$ together form a heterocyclic ring comprising 3-16 carbon atoms, together with the N atom of formula 1;
$R^9$ is hydrogen;
$R^1$ is selected from the groups consisting of hydrogen and $C_{1-3}$ alkyl; and,
R is selected from the groups consisting of $C_{6-14}$ aryl, substituted $C_{6-14}$ aryl, nitro, halogen, cyano, silyl, substituted silyl, sulfone, substituted sulfone, and fluorine, wherein the substituents are independently selected from the group consisting of: $C_{1-4}$ alkyl group, $C_{6-14}$ aryl group $C_{1-4}$, alkoxy group, $C_{7-14}$ aralkyl group, $C_{1-4}$ alkyl, $C_{6-14}$ aryl group, $C_{1-4}$ alkoxy, $C_{6-14}$ aryl group, and $C_{6-14}$ aryl $C_{1-4}$ alkyl group;
to the deprotected 5'-hydroxy terminus of the nucleoside or oligonucleotide, wherein said coupling reaction takes place in an acetonitrile solvent composition comprising acetonitrile and a basic aromatic heterocyclic solvent, to form a phosphite triester intermediate and
c) oxidizing the phosphite triester intermediate with a sulfurizing reagent,
d) optionally repeating steps a)-c) for at least one further elongation cycle, and
e) deprotecting the oligonucleotide and cleaving the oligonucleotide from the solid support.

The invention claimed is:

1. A method for the synthesis of a stereo-defined phosphorothioate oligonucleotide, comprising the step of:
   a) deprotecting a protected 5'-hydroxy terminus of a protected nucleoside, or protected oligonucleotide, attached to a solid support,
   b) coupling an oxazaphospholidine phosphoramidite monomer of Formula 1

2. A method according to claim 1, wherein said method comprises 2, 3, 4, 5, 6, 7, 8, 9, 10, 11, 12, 13, 14, 15, 16, 17, 18, 19 or 20 further elongation cycles (d).

3. The method according to claim 1, wherein the stereodefined phosphorothioate oligonucleotide is an antisense oligonucleotide.

4. A method for coupling an oxazaphospholidine phosphoramidite monomer to a 5'-terminus of a nucleoside or oligonucleotide, comprising the step of reacting the nucleoside or oligonucleotide, with an oxazaphospholidine phosphoramidite monomer of Formula 1 as defined in claim 1, wherein said reaction takes place in an acetonitrile solvent composition comprising acetonitrile and a basic aromatic heterocyclic solvent.

5. The method according to claim 1, wherein the basic aromatic heterocyclic solvent has a pKa of 4-7 or from 7-17 in water at 20° C.

6. The method according to claim 1, wherein the basic aromatic heterocyclic solvent is selected from the group consisting of pyridine, 2-picoline, 4-picoline, 3-picoline, and lutidine.

7. The method according to claim 1, wherein the basic aromatic heterocyclic solvent is pyridine.

8. The method according to claim 1, wherein the concentration (v/v), of the basic aromatic heterocyclic solvent in acetonitrile is between about 0.1% and about 50%.

9. The method according to claim 1, wherein the concentration (v/v), of the basic aromatic heterocyclic solvent in acetonitrile is between about 0.5% and about 10%.

10. An acetonitrile solution comprising an oxazaphospholidine phosphoramidite monomer of Formula 1 as defined in claim 1, acetonitrile and a basic aromatic heterocyclic solvent.

11. The acetonitrile solution according to claim 10, wherein the concentration of the oxazaphospholidine phosphoramidite monomer is between about 0.05 M and about 2 M.

12. The acetonitrile solution according to claim 10, wherein the concentration of aromatic heterocyclic solvent in acetonitrile is between about 0.1% and about 50% (v/v).

* * * * *

SEQUENCE LISTING

<160> NUMBER OF SEQ ID NOS: 1

<210> SEQ ID NO 1
<211> LENGTH: 13
<212> TYPE: DNA
<213> ORGANISM: artificial
<220> FEATURE:
<223> OTHER INFORMATION: LNA oligonucleotide sequence

<400> SEQUENCE: 1
gcattggtat tca                                                      13